US010288537B2

(12) United States Patent
Candon et al.

(10) Patent No.: US 10,288,537 B2
(45) Date of Patent: May 14, 2019

(54) TEST FLUID COLLECTION SYSTEM

(71) Applicant: Epona Biotech Ltd, Ballinode, Sligo (IE)

(72) Inventors: Ruth Candon, Sligo (IE); Heinrich Anhold, Sligo (IE); Di-Sien Chan, Sligo (IE)

(73) Assignee: Epona Biotech Ltd, Ballinode, Sligo (IE)

( * ) Notice: Subject to any disclaimer, the term of this patent is extended or adjusted under 35 U.S.C. 154(b) by 0 days.

(21) Appl. No.: 14/765,247

(22) PCT Filed: Feb. 4, 2014

(86) PCT No.: PCT/IB2014/058785
§ 371 (c)(1),
(2) Date: Jul. 31, 2015

(87) PCT Pub. No.: WO2014/118764
PCT Pub. Date: Aug. 7, 2014

(65) Prior Publication Data
US 2016/0153878 A1 Jun. 2, 2016

(30) Foreign Application Priority Data

Feb. 4, 2013 (GB) .................................. 1301951.8
Aug. 8, 2013 (GB) .................................. 1314232.8

(51) Int. Cl.
*G01N 1/38* (2006.01)
*B01L 3/02* (2006.01)
(Continued)

(52) U.S. Cl.
CPC .............. *G01N 1/38* (2013.01); *B01L 3/0203* (2013.01); *B01L 3/0241* (2013.01);
(Continued)

(58) Field of Classification Search
None
See application file for complete search history.

(56) References Cited

U.S. PATENT DOCUMENTS 5,234,813 A * 8/1993 McGeehan ....... B01L 3/502715
422/404
6,253,967 B1 * 7/2001 Sperna Weiland ... G01F 11/286
222/205

(Continued)

OTHER PUBLICATIONS

"Serum Amyloid A (SAA) Kit for HORSE", Jun. 21, 2011 (Jun. 21, 2011), pp. 1-2, XP055125418, Retrieved from the Internet: URL: http://www.frontier-institute.com/wp/wp-content/uploads/catalog/saa-eng.pdf [retrieved on Jun. 2, 2014] the whole document.

(Continued)

*Primary Examiner* — Jill A Warden
*Assistant Examiner* — Brittany I Fisher
(74) *Attorney, Agent, or Firm* — Hamilton, Brook, Smith & Reynolds, P.C.

(57) ABSTRACT

The present invention relates generally to methods and materials pertaining to assays, for example immunoassays, for biomarkers in body fluids e.g. blood. The invention also relates to diagnostic or screening methods for infections, and methods of differentiating between infectious and non-infectious conditions in mammals, particularly equines, for monitoring response to anti-infective/antibiotic therapy. The invention further relates to a test fluid collection system adapted to permit dilution and analysis of the collected test fluid. The invention further relates to monitoring exertional rhabdomyolysis in equines, and assay devices for all these things.

13 Claims, 21 Drawing Sheets

Figure 1:
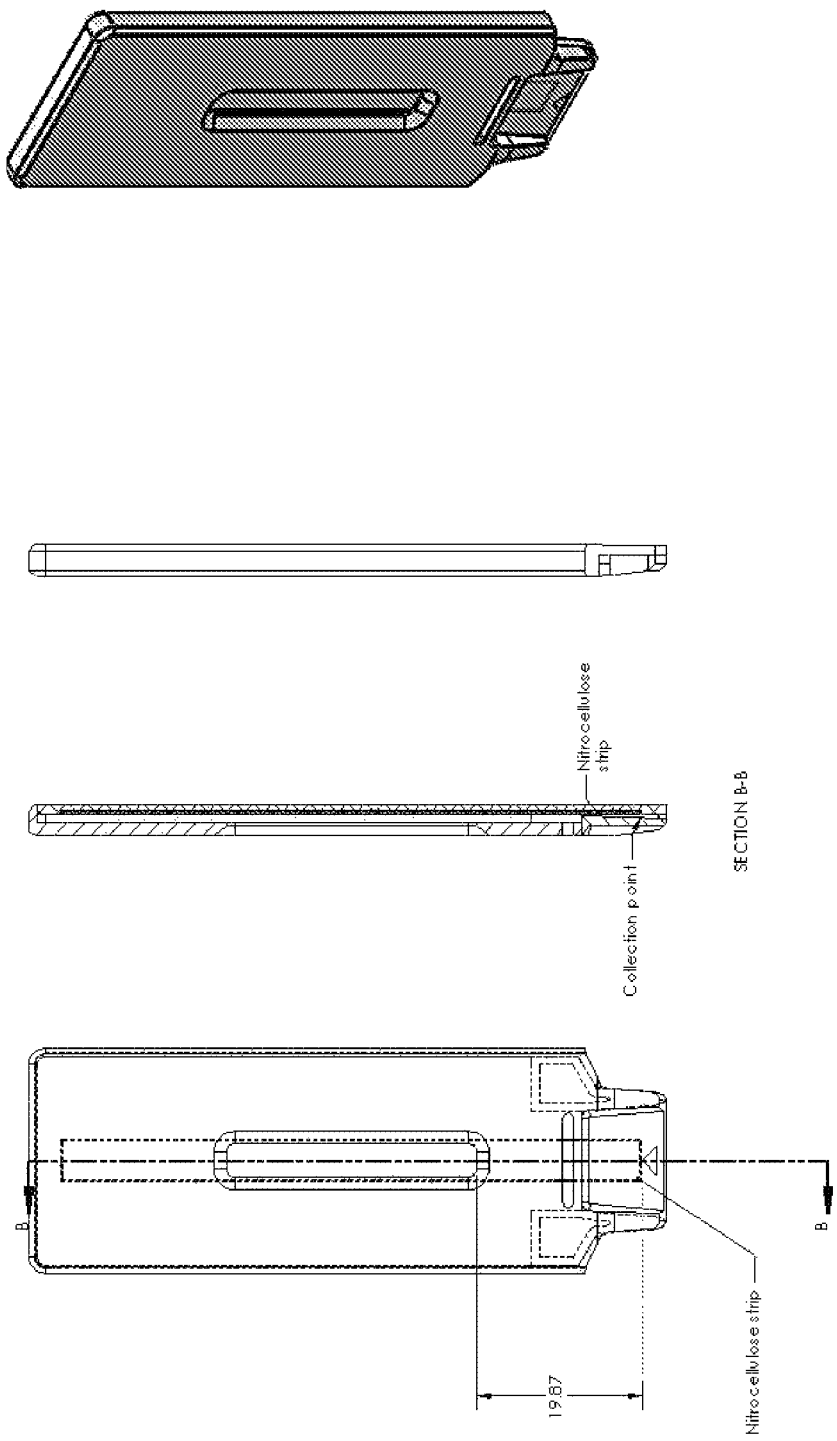

(51) Int. Cl.
G01N 33/543 (2006.01)
G01N 33/558 (2006.01)
G01N 33/68 (2006.01)

(52) U.S. Cl.
CPC ......... G01N 33/543 (2013.01); G01N 33/558 (2013.01); G01N 33/6893 (2013.01); B01L 2200/025 (2013.01); B01L 2200/026 (2013.01); B01L 2200/0689 (2013.01); B01L 2300/0838 (2013.01); B01L 2300/161 (2013.01); G01N 2001/383 (2013.01); G01N 2333/75 (2013.01); G01N 2333/775 (2013.01); G01N 2333/9123 (2013.01); G01N 2333/91188 (2013.01); G01N 2800/40 (2013.01)

(56) References Cited

U.S. PATENT DOCUMENTS

| | | | | |
|---|---|---|---|---|
| 2002/0020713 | A1* | 2/2002 | Kis | B65D 1/0207 222/95 |
| 2006/0228258 | A1* | 10/2006 | Samsoondar | G01N 21/03 422/82.05 |
| 2010/0279274 | A1* | 11/2010 | Lloyd, Jr. | G01N 1/38 435/5 |
| 2013/0021411 | A1* | 1/2013 | Feinn | B41J 2/1433 347/47 |

OTHER PUBLICATIONS

Allen, B.V., et al., "Leucocyte counts in the heathy English Thoroughbred in Training", Equine Veterinary Journal, vol. 16(3), 1984, pp. 207-209.
Christensen, M., et al., "Evaluation of an automated assay based on monoclonal anti-human serum amyloid A (SAA) antibodies for measurement of canine, feline and equine SAA", The Veterinary Journal, vol. 194, No. 3, Dec. 1, 2012, pp. 332-337, DOI: 10.1016/j.tvjl.2012.05.007.
Christofferson, M., et al., "Evaluation of the systemic acute phase response and endometrial gene expression of serum amyloid A and pro- and anti-inflammatory cytokines in mares with experimentally induced endometritis", Veterinary Immunology And Immunopathology, vol. 138, No. 1-2, Nov. 1, 2010, pp. 95-105.
Cywinska, A., et al., "Serum amyloid A level as a potential indicator of the status of endurance horses", Equine Veterinary Journal, vol. 42, Nov. 1, 2010, pp. 23-27, DOI: 10.1111/j.2042-3306.2010.00-280.x.
Hobo, S., et al., "Evaluation of Serum Amyloid A and Surfactant Protein D in Sera for Identification of the Clinical Condition of Horses with Bacterial Pneumonia", J. Vet. Med. Sci., vol. 69(8), Jan. 1, 2007, pp. 827-830.
Hultén, C., et al., "Serum amyloid A (SAA) as an aid in the management of infectious disease in the foal: Comparison with total leucocyte count, neutrophil count and fibrinogen", Equine Veterinary Journal, vol. 34, No. 7, Nov. 1, 2002, pp. 693-698.
Hultén, C., et al., "Interleukin 6, serum amyloid a and haptoglobin as markers of treatment efficacy in pigs experimentally infected with Actinobacillus pleuropneumoniae", Veterinary Microbiology, vol. 95, No. 1/02, Aug. 29, 2003, pp. 75-89.
International Search Report issued in International Application No. PCT/IB2014/058785, entitled "Device and Methods", Date of Search: Jun. 27, 2014.
Jacobsen, S., et al., "Evaluation of a commercially available human serum amyloid A (SAA) turbidometric immunoassay for determination of equine SAA concentrations", The Veterinary Journal, vol. 172, No. 2, Sep. 1, 2006, pp. 315-319, DOI: 10.1016/J. TVJL.2005.04.021.
Jacobsen, S., et al., "Evaluation of a commercially available apparatus for measuring the acute phase protein serum amyloid A in horses", The Veterinary Record, vol. 163, No. 11, Sep. 13, 2008, pp. 327-330.
Patterson, S.D., et al., "Acute phase response in the horse: plasma protein changes associated with adjuvant induced inflammation", Biochemistry International, vol. 17(2), Aug. 1988, pp. 257-264.
Pepys, M.B., et al., "Serum amyloid A protein (SAA) in horses: objective measurement of the acute phase response", Equine Veterinary Journal, vol. 21(2), 1989, pp. 106-109.
Stoneham, S.J., et al., "Measurement of serum amyloid A in the neonatal foal using a latex agglutination immunoturbidimetric assay: determination of the normal range, variation with age and response to disease", Equine Veterinary Journal, vol. 33, No. 6, Nov. 1, 2001, pp. 599-603.
Van Wuijckhuise-Sjouke, L.A., et al., "Plasma fibrinogen concentration as a parameter of the presence and severity of inflammatory disease in horses and cattle", Tijdschr Diergeneeskd, vol. 109(21), Nov. 1, 1984, pp. 869-872.
International Preliminary Report on Patentability issued in International Application No. PCT/IB2014/058785, entitled "Device and Methods," Date of Report: Aug. 4, 2015, 13 pages.

* cited by examiner

Figure 14A:
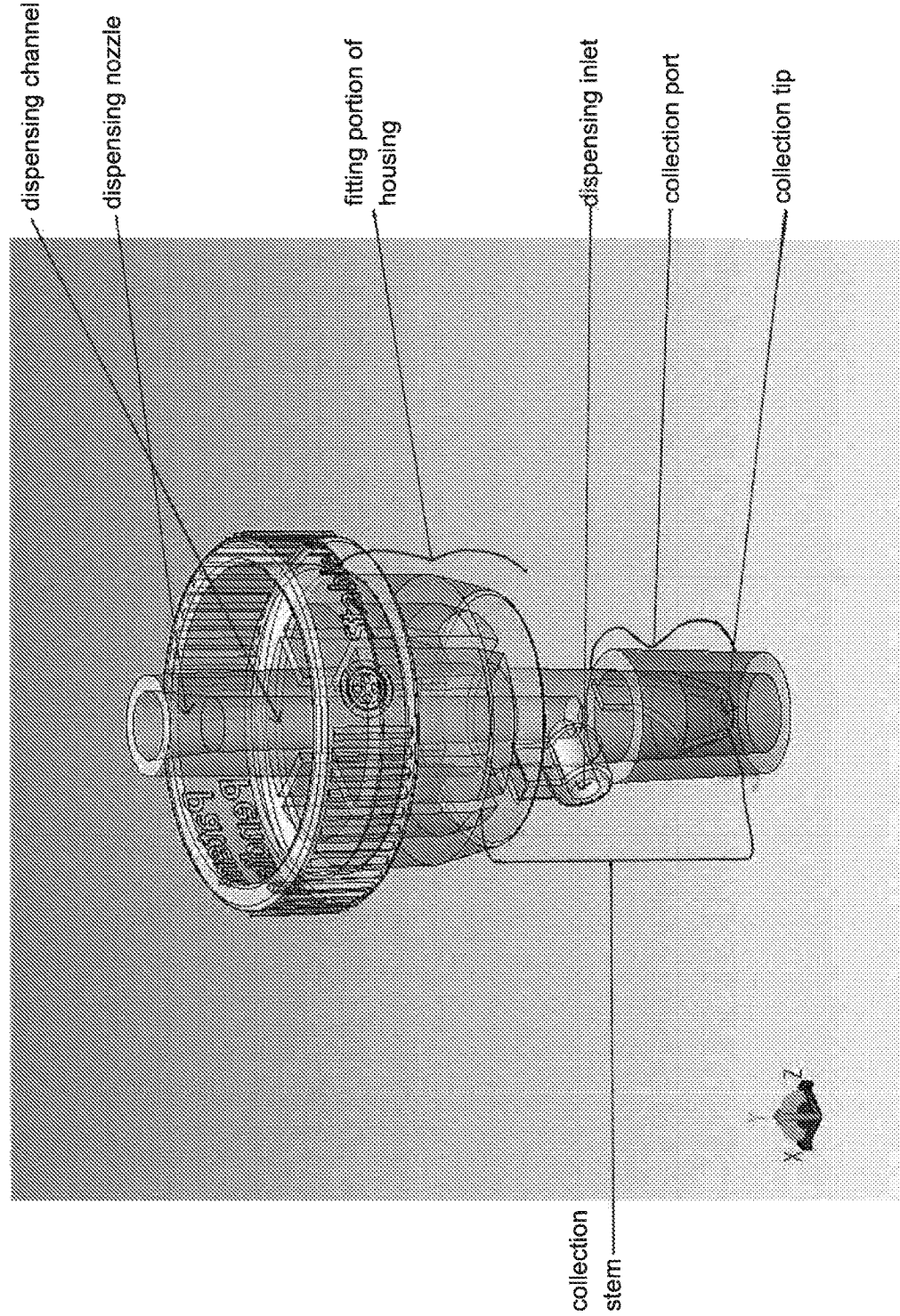

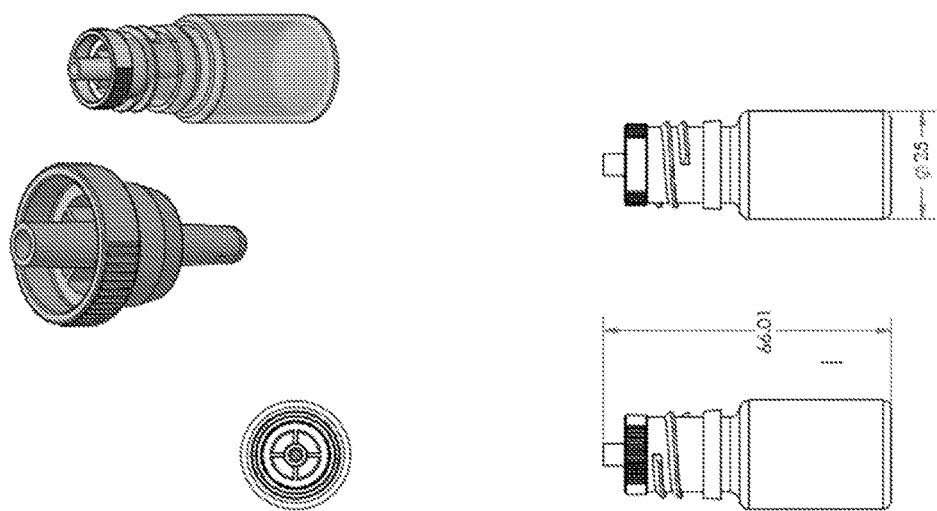
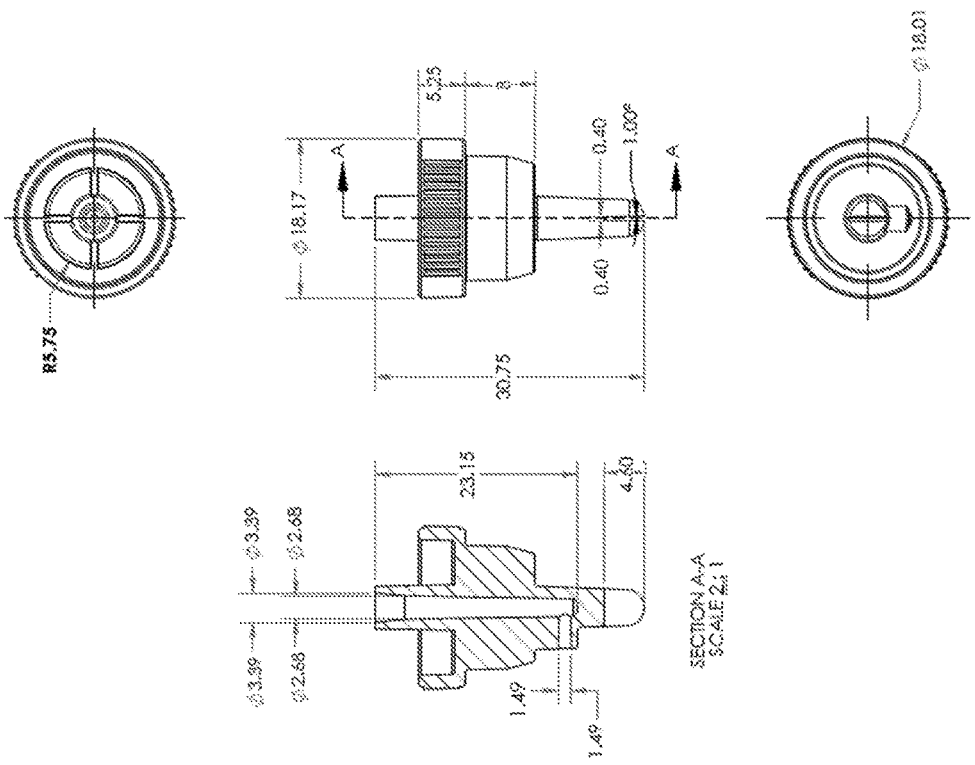
Figure 14b

Figure 16C:
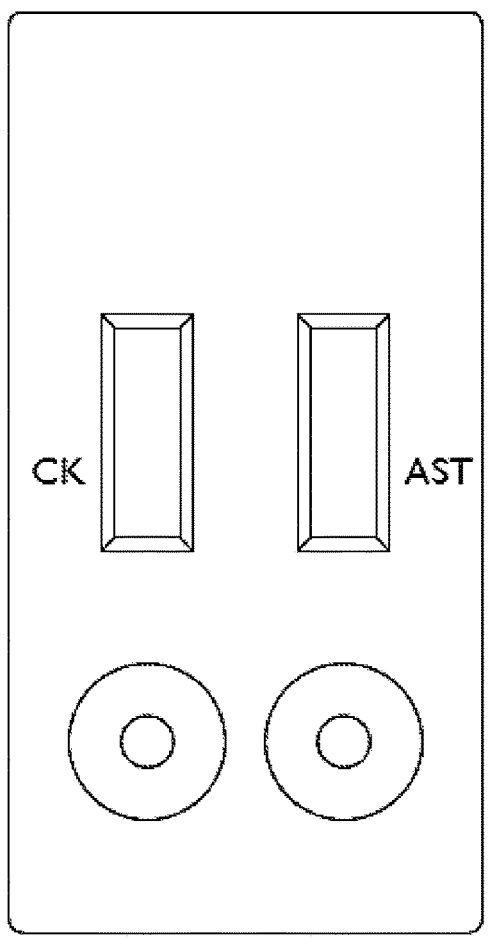

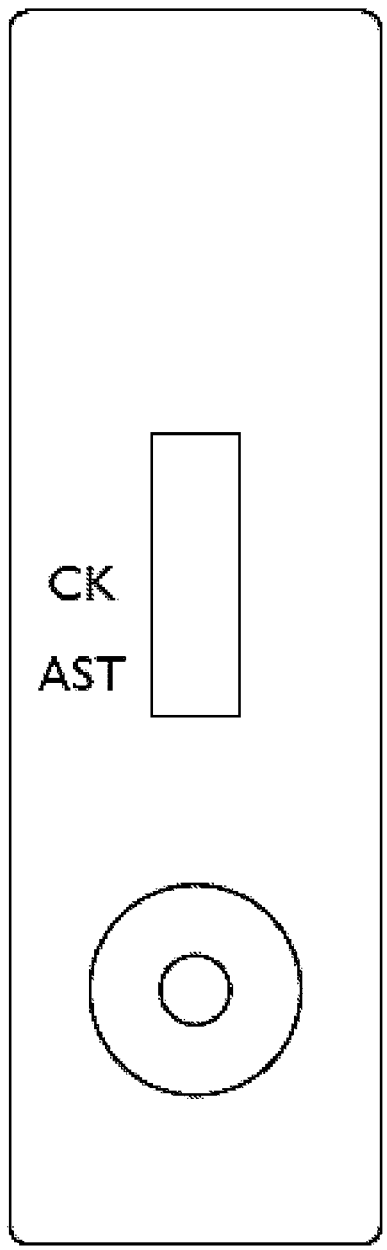
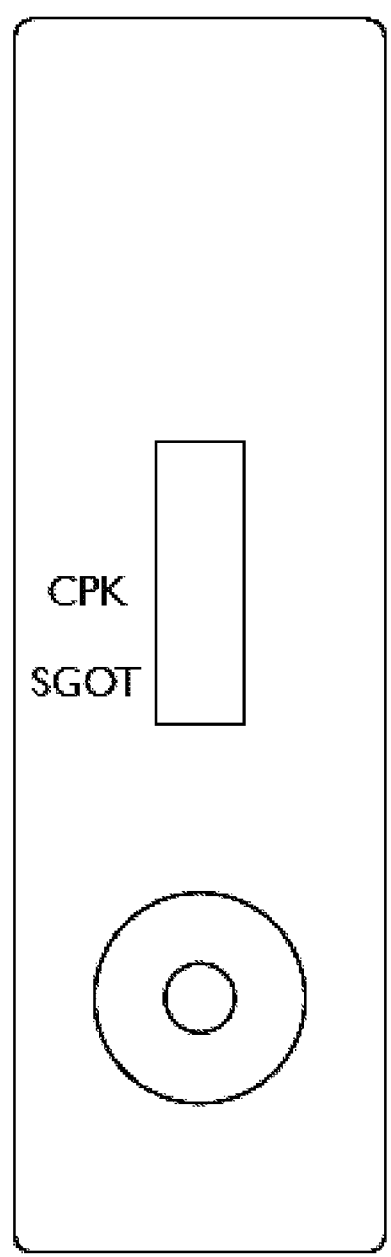
Figure 16a                    Figure 16b

TEST FLUID COLLECTION SYSTEM

This application is the U.S. National Stage of International Application No. PCT/IB2014/058785, filed 4 Feb. 2014, which designates the U.S., published in English, and claims priority under 35 U.S.C. §§ 119 or 365(c) to GB Application No. 1314232.8 filed 8 Aug. 2013 and GB Application No. 1301951.8 filed 4 Feb. 2013. The entire teachings of the above applications are incorporated herein by reference.

TECHNICAL FIELD

The present invention relates generally to methods and materials pertaining to assays, for example immunoassays, for biomarkers in body fluids. The invention also relates to diagnostic or screening methods for infections, and methods of differentiating between infectious and non-infectious conditions in mammals, such as equines, for monitoring response to anti-infective/antibiotic therapy. The invention further relates to a body fluid collection system adapted to permit dilution and analysis of the collected body fluid. The invention further relates to monitoring exertional rhabdomyolysis in equines, and assay devices for all these things.

BACKGROUND ART

Within the animal kingdom, horses are considered to be elite athletes due to their unique physiology. Since sport horses are required to perform at an extremely high level, even small changes in health can be detrimental to their performance and may have the potential to negate months of a costly training program. Further training of horses in which a decline in performance is noted may lead to rapid degeneration in certain circumstances and therefore an indication of the cause of ill health should be rapidly investigated. The detection of such changes is often challenging and requires the utilization of equipment and skill which are typically only provided in a laboratory setting.

Common causes of poor performance that may be managed at the horse's side by the veterinarian and the trainer include effects of the musculoskeletal system, the respiratory system, inflammation (such as general inflammation or infectious inflammation) and other illness. Conditions affecting the musculoskeletal and respiratory systems are of particular interest as breakdown in the physiology of these systems has been identified as the main cause of disruption and interruption of thoroughbred racing competitions (Wisher et al. 1996).

In many cases, the lack of clearly visible symptoms means that the specific body system affected cannot be determined, while in others the point at which the onset of symptoms becomes notable is already beyond the threshold where an intervention can be used to preserve the performance of the horse.

There is therefore a need for the rapid pre- or post-symptomatic detection and early stage diagnosis of clinical and sub-clinical infectious conditions such as those resulting in inflammation, and to distinguish such conditions from other inflammatory conditions so that appropriate treatment can be given. Early stage diagnosis in such situations may be enhanced by maintaining a careful and precise history supported by scientific evaluation of the affected body systems.

In addition, when a problem is known or suspected with the horse, there is a need for regular monitoring of the severity of the problem, and the response to intervention(s), such as response to antibiotic or anti-infective treatment, or monitoring severity of exertional rhabdomyolysis to avoid musculoskeletal damage and over-exertion.

Further, there is a need for pre-performance screening for competitions and for official veterinary inspections. Furthermore there would be a benefit in screening newborns for infection.

There are a number of devices which are available for point of care testing however these devices are tools solely for the use of the veterinarian and are not designed to facilitate use by other equine professionals such as the trainer. Nor are they designed for diagnosis of equine disease or ER specifically. Examples of such instruments include those disclosed in U.S. Pat. No. 5,096,669 and U.S. Pat. No. 5,122,284. U.S. Pat. No. 5,096,669, incorporated herein by reference, discloses a system comprising a disposable device and handheld reader which can perform a variety of electrochemical measurements on blood or other fluids. The system has found use in the human clinical setting and has subsequently been adapted for veterinary use. U.S. Pat. No. 5,122,284, incorporated herein by reference, describes a benchtop analyser which requires the insertion of disk based cartridges containing a predetermined panel of tests. The device is developed for use of veterinary professionals and its size makes it most useful as a benchtop unit rather than a complete point of care testing device.

WO2013/088429 relates to a method and assay for eliminating the hook effect in the detection of a target analyte such as an acute phase protein in a bodily fluid in which the target analyte comprises a member of a specific binding pair comprising applying the sample to a solid phase carrier material, generating a signal in accordance with downstream movement of the labelled first or second members and the target analyte to bind with the complimentary immobilised first or second members, and detecting the presence of the target analyte in accordance with the signal generated at the complimentary immobilised first or second members.

DISCLOSURE OF THE INVENTION

The inventors have carried out a number of large scale haematological and biochemical studies of racehorses which is unique in the field.

In one aspect of the invention, the inventors have identified specific levels of SAA which allow fast, accurate assessment of clinical and subclinical infection, which can be used as a screening tool and allows monitoring of disease progression and response to treatment.

WO2013/088429 discusses the use of a particular device for assessing increased levels of SAA in horses in relation to tissue injury, infection, trauma and arthritis. It further discusses the possible use of SAA to assess reconvalescence of horses recovering from infections or injury. However WO2013/088429 does not distinguish different possible causes of SAA, and nor does it identify particular concentrations or ranges which can be used by practitioners to assess infection and take appropriate action—for example pages 31-32 of WO2013/088429 discuss only the severity of "an active inflammatory condition" with the lowest SAA being indicative of the 'mild' condition being 32.9 µg/ml, and all concentrations below this being termed "normal".

However the present inventors have determined that, contrary to the prevailing view in the art, the presence of SAA can be used to actually distinguish infection from other types of inflammatory response. This means it can be used alone or in combination with other methods to screen for and confirm infection, as distinct from other inflammatory aetiologies, thereby permitting appropriate treatment measures to be taken. They have furthermore characterised the manner in which SAA levels reflect successful response to treatment of infection. These observations thus provide for improved methods for assessing these things.

The inventors further provide novel devices utilising these observations which can be used to simply and effectively:

Confirm with a high degree of confidence whether a subject exhibiting some abnormal symptom or behaviour is suffering from an infectious disease, as distinct from some other cause;

Rapidly and accurately assess whether a subject being treated for an infectious disease is responding or not to that treatment;

Screen for the presence of infection, particularly subclinical infection, in asymptomatic subjects, In preferred embodiment the device permits visual quantification or semi-quantification of critical individual concentrations in the range of about 15 to 1000 µg/ml (e.g. 15 µg/ml, 50 µg/ml, 200 µg/ml and 1000 µg/ml) in the sample, or up to 3000 µg/ml using an electronic reader. The device may include a reference card upon which representations of the critical concentrations intensity of are available for comparison.

This device thus allows, inter alia, trainers, breeders and veterinarians to look at their horse's health in a fundamentally different way, enabling them to manage health, not just react to clinical problems.

This research has also identified more generally a need for an inexpensive, portable device for testing levels of exertion indicators and other illness indicators in samples of a bodily fluid, particularly blood, from horses.

The inventors have therefore also developed a system that facilitates the collection and then analysis of a blood sample. The system permits the generation of an accurately diluted sample solution which can be readily applied to an assay device by the operator to give a consistent result rapidly, preferably at the site of sample collection, and is simple to use without specialist knowledge or training.

In a further aspect of the invention, the inventors have identified that the combination of CK and AST can be used to manage exertional rhabdomyolysis, e.g. optionally, but conveniently, these can be measured using a system or device described herein which measures both biomarkers at the same time within a suitable concentration range for each.

The device can be used for point of care testing which can be both performed and interpreted by the veterinarian and non-veterinarian at the horse's side.

These and other aspects of the invention will now be considered in more detail:

Specific Detection of Infection

In a one aspect of the invention, the inventors have identified that SAA levels allow fast, accurate assessment of clinical and sub-clinical infection. Optionally, but conveniently these can be measured using a system or device described hereinafter.

One of the many components of an inflammatory episode such as can arise from infection is an acute phase protein response, in which acute phase proteins are produced in the liver and released into the bloodstream in response to any stimulus causing tissue injury.

Serum Amyloid A is one of the acute phase proteins produced in the liver. Normal levels in healthy horses are very low but increase rapidly to peak 24 to 48 hours after infection and inflammation (Heegard 2000).

The inventors have determined unexpectedly that point of care determination of a critical level of SAA is a reliable marker of equine infectious inflammation and real time determination (e.g. assessing how quickly highly elevated drop following treatment) may assist greatly in management and monitoring of equine health.

Furthermore it may be useful in screening mammals, for example new-born mammals, for infection before the onset of symptoms.

Some particular embodiments of this aspect of the invention will now be described in more detail:

Serum Amyloid A (SAA)

SAA is a sensitive and rapid reacting inflammatory protein which can be useful in screening and monitoring early responses to infection and a subject's response to treatment. Equine SAA is present in three isoforms, SAA1 and SAA2 and SAA3. SAA1 and SAA2 are both involved in the acute phase response, and reference to "SAA" herein may refer to either SAA1 or SAA2, or both SAA1 and SAA2. Each isoform may be detected individually, or detected together (i.e. without distinguishing between the different isoforms).

The Equine SAA1 Fasta Sequence is:

LLSFLGEAARGTWDMIRAYNDMREANYIGADKYFHARGNYDAAKRG

PGGAWAAKVISDARENFQRFTDRFSFGGSGRGAEDSRADQAANEWG

RSGKDPNHFRPHGLPDKY

SAA1 FASTA Sequence: http://www.uniprot.org/uniprot/P19857.fasta
SAA1 Protein Information: http://www.uniprot.org/uniprot/P19857

The Equine SAA2 Fasta Sequence is:

MKLSIGIIFCSLVLGVSSREWFTFLKEAGQDAWDMWRAYSDMREAN

YKGADKYFHARGNYDAARRGPGGAWAAKVISDARENAQRVTDLFKF

GDSGHGAADSRADQAANEWGRSGKDPNHFRPRGLPDKY

SAA2 FASTA Sequence: http://www.uniprot.org/uniprot/F6ZL17.fasta
SAA2 Protein Information: http://www.uniprot.org/uniprot/F6ZL17

A Tool for Differentiating Between Infectious and Non-Infectious Conditions.

When a horse is presented with clinical/physical symptoms of illness and it is suspected that the cause of the condition is either infectious or indeed non-infectious, testing with SAA may be used to aid in diagnosis. The assessment can be performed based on the likelihood of the potential aetiology bearing in mind the horse and the environments. In general, this embodiment has particular utility for practicing veterinarians both in hospitals and ambulatory situations.

As explained in Example 4 the level of SAA was determined in horses diagnosed with infectious and non-infectious diseases and was observed to respond most rapidly and dramatically to bacterial and viral infections, while allergies, EIPH and other non-infectious inflammatory conditions showed little or no response. SAA levels were also observed to elevate during colic and post-colic surgery, which are both factors that can be readily assessed and if need be discounted by those skilled in the art. The case studies compiled in Example 4 demonstrate that SAA is a potent marker of infection and not a marker of general inflammation, and can thus be used for differentiating between infectious and non-infectious conditions.

SAA was confirmed to elevate in response to some of the most common infectious conditions (see Example 4). SAA levels elevate rapidly within 24 hours to over 4000 µg/ml in many cases and typically stay elevated until the acute phase response is overcome via antibiotic or anti-bacterial treatment or via the body's own immune system.

The benefits of such a method extend to diagnostic procedures where an infection can be confirmed before further investigation, as well as allowing for the prompt initiation of a suitable treatment regime for sick horses based on whether they are being treated for an infectious disease such as those associated with micro-organisms or non-infectious illness such as those associated with the environment or lifestyle or genetic factors.

Furthermore SAA has been seen to elevate to a larger extend when the horse is challenged with a bacterial infection compared to a viral infection which creates scope for SAA to be used not only as a marker of differentiation between infectious and non-infectious disease but also as a method of assisting in differentiating between the organism responsible which has implications for the type of therapy administered e.g. viral infections will not respond to antibiotic therapy.

In cases where a clinical condition is expected to be non-infectious, SAA may be used to confirm, via negative association, that that condition is indeed non-infectious. As shown in Example 4, it has been confirmed that SAA does not elevate in response to some of the most common kinds of non-infectious inflammation.

Common Examples in Ambulatory Practice

In racing stables SAA may be used to confirm bacterial lung infections after clinical symptoms such as coughing, snorting or mucus in the airways are observed. Bacterial lung infections in racehorses in training usually elevate SAA up to 1000 µg/ml. Bacterial lung infections secondary to exercise induced pulmonary hemorrhage can be observed 2-3 days post strenuous exercise and levels are observed to raise to a lesser extent; 30-50 µg/ml.

In sport horse stables such as show-jumping for example, SAA is usually used to confirm if a swollen leg or joint is due to bacterial infection or is a non-septic flare due to some other inflammatory response. For example in infected cases SAA is observed to elevate from 1000-5000 µg/ml depending on the severity of the infection, while non-septic joint flares do not show any detectable level of SAA. Septic osteoarthritis can also elevate SAA as high as 1000 µg/ml or above.

Colics both pre- and post-surgery as well as non-surgical cases have been shown to cause the elevation of SAA to 1000 µg/ml or higher, even when the horse undergoes surgery and does not receive antibiotics as part of their post-surgery treatment SAA levels can be observed to return to normal within 3-4 days. This is an example of potentially non-infectious inflammation where SAA is elevated. Colic however, is very common and the physical symptoms are readily identified by those skilled in the art.

A Tool for Monitoring Progress of Infectious Disease and Response to Anti-Infective/Antibiotic Therapy As explained in Examples 2 and 3, SAA can be used to efficiently monitor the recovery of a mammal such as an equine mammal from infection.

In some embodiments a concentration of SAA above about 10, 15, 30, 50, 100 or 200 µg/ml indicates the horse should be monitored regularly. An increasing concentration of SAA indicates the horse may require medical treatment. A decreasing concentration of SAA indicates the horse is improving, e.g. naturally or in response to medical treatment.

The studies shown in the Examples particularly demonstrate the use of SAA to determine the biochemical efficiency of the course of treatment and SAA elevations and decreases were in agreement with clinical examination. In particular the data indicated that SAA levels can resolve before the traditional WBC profile returns to normal. In addition SAA can be used to determine the efficacy of a treatment by monitoring the response of the protein post administration.

More specifically, SAA is normally not present (or present only at trace levels) in equine blood but gets produced in abundance in response to infectious disease.

The inventors have shown that SAA can elevate from trace levels to 5000 µg/ml within 18-24 hours, making it a rapid response diagnostic or prognostic. They have further shown that serum concentration of SAA can drop in response to effective antibiotic or anti-bacterial treatments. The typical pattern in SAA drop-off displays a slight tail on the slope (see FIGS. 17a-c). In particular the inventors show that the rate of SAA reduction is an indicator of the effectiveness of the treatment with a fully effective treatment expected to show a half-life reduction of approx. 12-24 e.g. 13, 14, 15, 16, 17, 18, 19, 20, 21, 22, 23, or 24 hours—more preferably about 16-20 hours, most preferably 17, 18 or 19 hours in vivo.

Accordingly, provided herein is a method of diagnosing or monitoring a condition in a horse, comprising
(i) determining the level of SAA in a blood sample from the horse,
(ii) repeating step (i) after a defined period; and
(iii) optionally repeating step (ii),
wherein an increase in the level of SAA indicates the condition is deteriorating, and a decrease in the level of SAA indicates the condition is improving.

In some embodiments, the defined period may be about 6, 12, 18, 24, 48 or 72 hours.

In some embodiments, the condition is infection, e.g. bacterial infection or viral infection.

In some embodiments a concentration of SAA above about 10, 15, 30, 50, 100, 200 or 1,000 µg/ml indicates the horse should be monitored carefully, and/or a treatment step as described herein should be carried out. Preferably, the treatment step comprises a period of rest for the horse.

A concentration of SAA below about 10-15 µg/ml, e.g. below about 7.5 µg/ml, indicates the horse may be healthy, i.e. have normal performance. However, other markers, e.g. tracheal wash or white blood cell count, may indicate the horse is not yet fully recovered.

A Tool for Screening for Infection in Mammals

In another embodiment of this aspect of the invention, the present invention provides novel methods and devices for screening.

In preferred embodiments, a concentration of SAA above about 7.5, 10, 15, 20, 25, 30 or 50 µg/ml (micrograms/ml), e.g. above about 10 to 15 µg/ml, indicates the potential for infection and impaired horse performance.

As shown herein, it has been found that horses with an SAA concentration between about 10-15 µg/ml and 200 µg/ml, e.g. between about 15 µg/ml and 100 µg/ml, between about 30 and 200 µg/ml or between about 50 and 200 µg/ml are unlikely to have visible symptoms. However, their performance, e.g. speed and/or endurance performance, for example in horse racing or other intense exercise, is significantly impaired.

Horses with an SAA concentration greater than about 100 or 200 µg/ml are clinically unwell, e.g. showing clinically significant symptoms or inflammation. Horses with an SAA concentration lower than about 10-15 µg/ml, e.g. lower than about 7.5 µg/ml, are considered free from subclinical infection, e.g. are expected to perform normally.

Concentrations of SAA above about 10-15 µg/ml indicate increasingly impaired performance. In some embodiments, a concentration of SAA above about 30, 50 or 100-µg/ml indicates increasingly impaired performance.

Screening is a process which can conducted "blind" on individuals or groups of subjects (e.g. horses). There are 3 main utilities for screening according to the present invention;
- I. Detecting infectious disease
  - a. For disease control
  - b. To identify disease early (sub-clinical)
- II. Pre-performance testing
- III. Post-transportation These will now be discussed in more detail:

I.a. Screening to Detect Infectious Disease for Disease Control

This is a protocol that can be practiced at veterinary inspections, such as quarantine, ports or borders or prior to inter-state transport in the US. It may also be conducted to manage disease outbreaks, screen feral populations or geographic locations for disease control and/or statistics.

Assessing SAA according to the present invention has utility as a rapid and simple to use screen or pre-screen to identify potential infection in the subject.

Common examples of infectious diseases that may be screened or pre-screened in this context are Equine infectious anemia (virus) and Piroplasmosis (protozoa), other equine diseases of lesser interest in this type of screening are Equine Viral Arteritis and in some cases Equine Herpes Virus types 1 and 4.

In this case the intervention upon a positive result could be to refuse entry of horses into certain event, geographic area or border e.g. a state border.

Methods of the invention may or may not be followed by further diagnostics to confirm the kind of infection. Such confirmatory diagnostics are well known to those skilled in the art. For example with EIV the commonly used diagnostic is the "coggins test" which is an immunodiffusion test. For Piroplasmosis the confirmatory diagnostic test is typically a PCR.

I.b. Screening to Detect Infectious Disease for Early Identification

This may be conducted as a cost-reduction and/or risk-reduction exercise at equine facilities such as breeding farms, or competitive training facilities.

Breeding and Rearing Facilities

Common infectious diseases amongst young horses in breeding and raring facilities are *Rhodococcus equi* (bacterial infection) and Rotavirus. A protocol for effective management of these conditions in neonates would be to screen within 8-10 hours of birth and repeat every 14 days for the first 12 weeks of life. *R. equi* cases were observed to raise SAA as high as 5000 µg/ml within 24 hours while Rotavirus can typically elevate SAA to 1000-2000 µg/ml or higher. Monthly screening would be adequate for older horses and may be seasonal, e.g. horses could be less susceptible to these infections in winter.

While there are other markers such as white blood cells and fibrinogen that elevate in *R. equi*, Chafflin et. al. (2013) have shown that they are not reliable for predicting subsequent onset of clinically apparent *R. equi* (see "Evaluation of Hematologic Screening Methods for Predicting Subsequent Onset of Clinically Apparent *Rhodococcus Equi* Pneumonia in Foals". Chafflin M, Coen N, Blodgett G and Syndergaard M. AAEP Proceedings. Vol. 59. 2013. p 267; "Evaluation of Ultrasonographic Screening Parameters for Predicting Subsequent Onset of Clinically Apparent *Rhodococcus Equi* Pneumonia in Foals." Chafflin M, Coen N, Blodgett G and Syndergaard M. AAEP Proceedings. Vol. 59. 2013. p 268. The present inventors have shown in their unique studies that in *R. equi* SAA elevates in all tested cases and is a reliable marker when screening for *R. equi*. Furthermore SAA elevates earlier than both WBC and fibrinogen in both *R. equi* and Rotavirus cases.

If a foal is suspected of *R. equi* the confirmatory diagnostic is ultrasonographic scanning of the lungs. According to Chafflin et. al. (2013) however, 79% of *R. equi* cases confirmed by ultrasonographic scanning naturally resolve without treatment and therefore it is a poor predictor of the onset of clinically apparent *R. equi*.

If *R. equi* infects a foal it can develop into pneumonia and can cause scar tissue formation in the lungs which is detrimental to a racing career for example. In circumstances where *R. equi* has been confirmed, SAA can be monitored to see if the condition is naturally subsiding or not, whereby SAA is observed to reduce from levels of about 700 µg/ml or higher to trace levels.

Rotavirus is either confirmed by PCR, or more commonly, the foal is closely monitored by physical exam for diarrhea (symptom of Rotavirus) and will have its fluids and electrolytes closely managed as well as SAA levels. Rotavirus can elevate SAA to 1500-2000 µg/ml or greater prior to the onset of symptoms.

As shown in Example 5, SAA can be used to distinguish between healthy newborns and those who may be seen to develop health problems immediately or be susceptible to the development of problems in the weeks and months after birth.

The inventors showed no background SAA count in most subjects. The invention can be used to provide an early indicator of future health problems, and for the identification of sub-clinical early stage infection.

Utilities for screening older horses in breeding facilities includes screening mares for common infections that would cause economic and emotional loss, i.e. losing a pregnancy or newborn. The common infections in breeding mares are placentitis (placental infection), bacterial endometritis (uterine infection) and Equine Herpes Virus.

Confirming sub-clinical placentitis is conducted via ultrasound scanning of the uterus and placenta to look for signs of placental thickening, placental/uterine edema, cervical opening, excessive folds or placental separation, all of which can be vague. Clinical placentitis would be confirmed by physical examination for vulvar discharge. Mares with placentitis may abort or have foals born with complications (which foals could be screened with SAA upon birth).

Bacterial endometritis would be confirmed via ultrasonographic scanning of the uterus and/or a vaginal swab. The presence of fluid in the uterus and/or bacteria in the swab would indicate the presence of bacterial endometritis, which if present at the time of conception, significantly increases the risk of early fetal death.

EHV is confirmed via PCR. EHV causes early abortion and it is routine in larger breeding facilities to vaccinate against it.

II. Competitive Training Facilities

Common infectious disease in racehorse, trotting horse and endurance horse training facilities would be unidentified viral infections and bacterial lung infections.

Pre-performance screening is with the aim making a decision to enter into competition or not, and/or to gamble on the horse winning in competition. A decision to withdraw from competition may be drawn from SAA levels greater than 7.5 µg/ml-15 µg/ml, or higher levels (e.g. above 100 µg/ml) if it was accepted that a loss of performance might result.

The inventors have showed that 98% of racehorses under 7.5 µg/ml prior to racing performed as expected, while horses with SAA of 15 µg/ml or higher did not perform as expected.

In these examples, the device is used to make decisions to compete or not, and/or to estimate the likelihood of winning. Thus in this context, further diagnostics may not be required or conducted. Nevertheless a typical confirmatory diagnostic may be nasopharyngeal endoscopy and/or bronchoalveolar lavage (BAL) to look for traces of bacteria and viruses. Further blood diagnostics may also be conducted such as fibrinogen and/or white blood cells.

Common infections in sport horses, including showjumpers, eventers, endurance horses, dressage horses, quarter horses and others vary depending on geography. In the US the most common infectious diseases of concern in these horses are Equine Protozoal Myeloencephalitis (EPM) and Lyme disease (bacterial). EPM is usually confirmed via physical examination and ELISA based on multiple immunogenic proteins located on the surface of the parasite. Diagnosis is enabled by determining serum:CSF titers however testing cerebrospinal fluid is not commonly practiced due to the collection risk. Lyme disease is also difficult to confirm and is done so via multiplexed immunoassay which is based on the detection of antibodies to three *B. burgdorferi* (causative parasite) antigens in equine serum. The inventors have identified a method of retrospective diagnosis of EPM and Lyme disease by treating with the relevant treatments and monitoring response to treatment by determining SAA levels.

III. Post-Transportation Screening

The most common kind of infection post-transportation is pleuropneumonia a bacterial infection of the lungs. Pleuropneumonia is confirmed by identifying fluid in the pleura via ultrasound scanning. SAA levels can raise as high as 3500 µg/ml within 24 hours in cases of pleuropneumonia and stay elevated until the bacterial infection clears, the inventors have observed that even when fluid resolves in the lungs the acute phase response can stay elevated, therefore SAA provides valuable insight over ultra sound scanning alone.

A Broad Range Portable Device for Assessing SAA

The assessment of SAA for the practice of the invention described herein can be done by any appropriate means known in the art. Preferred body fluid collection systems and analytical devices are described by way of non-limiting examples hereinafter. Such systems and devices can be used to measure SAA at both very low and very high levels in the same assay.

In one aspect the invention provides a diagnostic device with an SAA detection range of 0-3000 ug/ml wherein a result of less than or equal to a specified level (here: about 15 µg/ml e.g. about 7, 8, 9, 10, 11, 12, 13, 14 or 15 µg/ml) indicates that there is no infection present.

Preferred devices give a simple indication which is specific to whether the concentration of SAA in the body fluid is above or below a specified level that which has been demonstrated by the present inventors to suggest that intervention is appropriate.

This can be used in combination with the diagnostically relevant ranges which have been identified through haematological and biochemical studies and which are described in more detail below e.g. where 7.5-200 ug/ml SAA may indicate the presence of subclinical infection and over 200 indicates clinical infection which is can be observed on examination.

Preferred devices are portable and handheld, and can be readily used and understood. A preferred device is a portable colour indicator device for the detection of infectious diseases, which can be used for field-testing for SAA with immediate results.

In some embodiments, the lateral flow device produces a marker, e.g. a coloured line or stripe which is detectable (e.g. to the naked eye) at an SAA concentration of at or above about 10-15 µg/ml, e.g. about 7.5, 10, 12.5 or 15 µg/ml in the body fluid sample. Preferably, the marker increases in intensity with increased SAA concentration. Preferably, the concentration of SAA can be reliably determined between a range of about 0 and 3,000 µg/ml, e.g. between about 0 and 1,000

Such devices are discussed in more detail hereinafter.

Test Fluid Collection System

Provided herein is a novel test fluid collection system, for collecting and preferably diluting of test fluids.

In preferred embodiments the system is used for body fluids, such as blood, and may be abbreviated herein to "BCS". However the disclosure applies mutatis mutandis to the collection of other test fluids—for example from environmental or industrial sources, or any other source.

As explained in Example 6, the body fluid collection system (preferably blood collection system) of the present invention simplifies sample collection and preparation for use preferably with a point-of-care diagnostic test. A typical point-of-care sample handling procedure involves collecting the sample (including but not limited to blood, urine or saliva), pipetting a metered volume of sample, adding it to a diluent solution and transferring a measured volume of sample/diluent mixture to the point-of-care device. The system allows for relatively contactless mixing and distribution of the solution.

The BCS has five main features;
1. A housing, which includes a fitting portion to engage a container
2. The multi-purpose sample collection tip
3. The metered volume sample collection port
4. The dispensing inlet
5. The dispensing nozzle The BCS circumvents the use of two different pipettes and reduces variation introduced by human error. It incorporates a "capillary" action in conjunction with a dispensing nozzle which can be a convenient dropper. When used with the liquid container which provides the diluent, there is formed a 'mechanical flow path' whereby reducing the volume of the container (e.g. by squeezing) expels the diluted sample through the nozzle.

By combining a sample collection tip, metered volume collection port and mechanical dispensing system, the BCS allows for the collection and preparation of a sample of blood, for example, without the requirement of blood bottles, blood tubes, pipettes droppers or capillary materials.

While the preferred device is exemplified for blood dilution, the volume of component to be diluted can be adjusted by the size of the spacing in the collection port (depth and width) as appropriate to the surface tension of the liquid to be sampled.

Capillary blood provides a reliable source of biological and/or physiological information that can be obtained from blood sampling, including but not limited to; blood cell number and morphology, biomarkers, lipids, enzymes, electrolytes, pH as well as other relevant diagnostic and/or veterinary medical related information.

The body fluid collector may be used in conjunction with a needle, lancet or other suitable blood letting device. It may also be used with a syringe, bottle, tube, blood bottle or blood tube. In one embodiment, the BCS (and in particular the sample collection tip) can be attached to a needle.

Equine capillary blood may be collected from a number of different sites on the equine anatomy, most notably the soft tissue around the gums and mouth as well as the nose and muzzle. Other suitable sites may include the under-side of the tail, the heels, the sheath or other highly vascular areas of the anatomy.

Blood or other bodily fluids may be collected by any conventional means for use as described herein. Conventional methods for obtaining equine blood samples use the venepuncture method, in which blood is drawn directly from the equine jugular vein using a syringe or similar apparatus. However, the inventors have determined that a small blood sample may also easily be obtained for use e.g. with an LFD or other point of care device by puncturing the lip or gum of an equine, for example using a lancet or similar apparatus.

Thus the body fluid collector enables a body fluid sample (e.g. blood) to be analysed by simply contacting a drop of (e.g.) blood on the body (e.g. gum, lip or skin) of the horse with the body fluid collector. It can also collect fluid from the tip of a syringe, bottle or tube or be connected to a needle to withdraw blood directly from the vein/artery.

In one embodiment the port is optimized for the collection of whole blood.

In another embodiment the BCS is optimized for the uptake of saliva.

In another embodiment the BCS is optimized for the uptake of serum.

In a further embodiment the BCS is optimized for the uptake of plasma.

In a yet further embodiment the BCS is optimized but not limited to the uptake of any of urine, milk, synovial fluid, peritoneal fluid, cerebrospinal fluid, plant extract, food extract, water or wastewater samples.

Some particular elements of the system will now be discussed in more detail:

In one aspect of the invention there is provided a test fluid collection system, for collection of a metered quantity of a test fluid to be diluted for analysis the system comprising a housing comprising a
(i) collection tip
(ii) a collection port
(iii) a dispensing inlet and a
(iv) dispensing nozzle;
wherein the collection tip is at a first end of the housing, and is for contacting a sample of the test fluid;
wherein the collection port is proximal to and in fluid communication with the collection tip and comprises two spaced members having opposing hydrophilic surfaces,
  wherein said surfaces define a volume between them which corresponds to the metered quantity of test fluid to be collected;
  wherein the distance between the spaced members is such that the test fluid from the sample tip can be drawn into the volume by capillary action;
wherein the collection tip and dispensing nozzle are at opposite ends of said housing;
wherein the dispensing inlet is proximal to the collection tip, and in fluid communication via a dispensing channel to the dispensing nozzle which runs through said housing;
wherein the housing is adapted to be fitted into the opening of a liquid container containing liquid for diluting the metered quantity of the test fluid, with said collection port and said dispensing inlet within said container, and with a seal fit between said opening and said housing;
wherein the dispensing nozzle is adapted to dispense diluted test fluid from the container when the volume of said container is reduced.

Dimensions

In one embodiment the total longitudinal length of the BCS between 25 and 30 mm

In one embodiment the BCS has a circular cross section of circumference between 15 and 20 mm at the widest point.

Collection Tip

The collection tip may be positioned on a collection stem which is connected to the dispensing inlet and incorporates the collection port.

The collection stem may be elongate to allow for easier sample collection into the port from (for example) a blood tube—thus is may be for example greater than 20, 25, 30, 40, 45, 50 mm from the collection tip to the fitting portion of the BCS (described in more detail below). An elongated collection stem may also allow for easier extraction of a sample from a tube or bottle.

In a preferred embodiment the BCS allows for pipette-free sample metering

In another embodiment the BCS allows for venous or arterial blood sample collection without the requirement of blood tubes or syringes.

Collection Port

As noted above the collection port is composed of two closely aligned flat surfaces These may be parallel but preferably are not parallel to each other but are slightly angled (e.g. about 1°, 2°, 3°, 4°, 5°, flaring outwards towards the tip) to encourage greater capillary flow.

In one aspect of the device the surfaces of the collection port are coated with a hydrophilic coating such as Triton (or any known hydrophilic material or hydrophilic surface treatment—e.g. a hydrophilic polymer and/or a polymer coated with a hydrophilic coating.

In one aspect of the device the surfaces of the collection port are coated with an anticoagulant (e.g. EDTA, Lithium heparin, Sodium citrate, or the like).

The corners of the walls or members or the collection port may be bevelled or shaped to increase surface tension in the volume holding the fluid.

The length and width of the space contained within the collection port (between the closely aligned walls) defines the volume that can be collected.

In a preferred embodiment the collection port is composed of two open sided closely aligned walls which form an open channel. In a related embodiment the open side walls of the collection port allow the rinsing of blood out of the collection port.

The spacing between the members may be less than 1 mm e.g. less than 0.2, 0.3, 0.4, 0.5 mm at its narrowest point spacing.

The width of the members at their widest point may be less than 10 mm e.g. about 1, 2, 3, 4, 5, 6, 7, 8, or 9 mm.

The area each opposed surface may e.g. be between 2 and 100 mm².

The distance between the spaced members, and the area of the members, will be selected to enable the desired volume of body fluid sample to be drawn into to the LFD. Preferably, the collector transfers samples between about 1 and 100 µl, more preferably about 5, 6, 7, 8 8.5, 9, 10, 15, 20, 25, 30, 35, 40, 45, 50, 60 70, 80, 90 or 100 µl. Most preferably the collector collects between about 5 and 30 µl.

Interface with Container

In a preferred embodiment the housing includes a fitting portion which is adapted to be a push fit into the opening of a container. For example this portion may have a cylindrical waist to fit the neck of a bottle via a push fit where it can be retained by friction or compression. The fitting portion size is adapted to fit and create a seal with any standard commercially available bottle.

It may include a frusto-conical portion which is tapered (inwardly towards the collection tip). This permits easy insertion of the fitting portion into e.g. a bottle neck.

In one embodiment of the BCS the fitting portion is cylinder (optionally tapered) of at least 5, 6, 7, 8, 9 or 10 mm in longitudinal length. It may be less than 20, 19, 18, 17, 16, 15 mm in length.

In one embodiment the diameter of the fitting portion is adapted to fit within a bottle or container with an inner neck diameter of 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm 25 mm, 26 mm, 27 mm, 28 mm, 29 mm, 30 mm, 31 mm, 32 mm, 33 mm, 34 mm, 35 mm.

Thus in one embodiment the diameter of the fitting portion is 1 mm, 2 mm, 3 mm, 4 mm OR 5 mm wider than the inner dimension of the neck of the accompanying bottle in order to create an appropriate seal, as appropriate to the resilience of the material of the container neck and fitting portion.

A preferred diameter of the fitting portion is between 15 and 20 mm e.g. 16, 17, 18, 19 mm.

A most preferred embodiment has a circumference of 18.7 mm which fits conveniently into a bottle with an internal bottle neck diameter of 14 mm.

In a preferred embodiment the BCS system is used in conjunction with a plastic (compressible) bottle made from a low-density polyethylene (LDPE).

In another embodiment the BCS allows for pipette-free sample preparation

Dispensing Diluted Fluid

Generally inversion of the container (e.g. bottle) to which the BCS can be attached can result in the entry of diluted sample into the dispense port and along the channel where it travels to the dispense nozzle.

Preferably pressure to the container forces diluted sample through the dispense nozzle where it is formed into measured droplets according to the inner dimensions and slope (as mentioned below) of the dispenser nozzle.

Preferably the dispense nozzle is dimensioned to determine and control drop size (e.g. 10-300 µl)

The dispense channel may be flared at the dispense nozzle exit which aids in the creation of a uniform drop.

An elongated dispense nozzle may also allow for easier mixing as it is immediately immersed in the diluent on attachment of the BCS to the bottle In a preferred aspect of the device the sample collection and dispense actions of the BCS are separate functions which can be performed independently of each other.

In another embodiment the BCS allows for metering and dispensing in the single device without mechanical or moving parts.

Construction

The BCS may be made of transparent materials thereby giving feedback to the user when the collection port is filled and\or dispensing is occurring.

Preferably, the surface of the mold used to make the channel walls will have a high polish finish (SPI A1 finish), and may optionally have additional hard chrome plating.

A preferred BCS device is described in the Examples and Figures hereinafter.

Analytes for Indicating Equine Exertional Rhabdomyolysis (EER)

Equine exertional rhabdomyolysis (ER) is a debilitating condition that occurs mainly as a response to exertion, resulting in varying degrees of stiffness and pain due to muscle damage (Landau et al. 2012). Sporadic cases can occur when a horse exercises at a level above its fitness while chronic cases are often attributable to an underlying heritable condition. Equine creatine kinase (CK) levels spike within 4-6 hours of ER and return to normal within 3 days to 7 days (EL-Deeb, 2012). Aspartate aminotransferase (AST) activity peaks approximately 24 hours after an episode of ER and may require several days to weeks to return to basal levels (Cardinet, 1997).

If a horse experiences an episode of ER during exercise it will set the horse back in its training program causing significant economic loss. Conversely if a horse unnecessarily foregoes exercise as a precaution for ER, its training schedule will also be compromised. The inventors have determined that having a real-time diagnosis of CK and AST levels can aid in the predicting the onset of ER and can be used to determine if a horse has tied up, the severity of the episode and when the horse is recovering. In the study described in the Examples below, 26% of the horses in the study tied up over a 6 month period and of those 14 recurrent episodes were recorded, illustrating the severity of the problem. The present invention can assist greatly in managing ER and the response to treatment, which for example may involve careful nutritional management.

Aspartate Aminotransferase (AST) and Creatine Kinase (CK)

AST is present in two isoforms in equines, encoded by GOT1 and GOT2 respectively. Elevations of AST are seen in the presence of myopathy or hepatopathy. After muscle damage, AST levels peak at 24-48 hours and generally return to baseline concentrations within 10-21 days assuming that no further damage occurs. An elevation in the muscle isoform of CK is specifically seen in acute phase myopathy. CK levels peak at 6-12 hours and return to baseline levels within 3-4 days.

Equine AST FASTA Sequence

```
MTSPSIFVEVPQAQPVLVFKLTADFREDPDPRKVNLGVGAYRTDDC

QPWVLPVVRKVEQKIANNSSLNHEYLPILGLAEFRSCASRLALGDD

SPALQEKRVGGVQSLGGTGALRIGAEFLSRWYNGTNNKNTPVYVSS

PTWENHNGVFSGAGFKDIRSYHYWDATKRGLDLQGFLNDLENAPEF

SIFVLHACAHNPTGTDPTPEQWKQIASVMKRRFLFPFFDSAYQGFA
```

-continued

```
SGNLDRDAWAVRYFVSEGFELFCAQSFSKNFGLYNERVGNLTVVAK

EPDSILRVLSQMQKIVRITWSNPPAQGARIVAFTLSDPGLFKEWTG

NVKTMADRILSMRSELRARLEALKTPGTWNHITEQIGMFSFTGLNP

KQVEYLVNQKHIYLLPSGRINMCGLTTKNLDYVATSIHEAVTKFQ
```

GOT 1 FASTA Sequence: http://www.uniprot.org/uniprot/P08906.fas
Protein Information: http://www.uniprot.org/uniprot/P08906
Equine Creatine Kinase FASTA Sequence, CKM

```
MPFGNTHNKFKLNYKPEEEYPDLSKHNNHMAKALTFDIYKKLRDKE

TPSGFTLDDVIQTGVDNPGHPFIMTVGCVAGDEESYVVFKELFDPI

IQDRHGGYKPTDKHKTDLNHENLKGGDDLDPHYVLSSRVRTGRSIK

GYTLPPHCSRGERRAVEKLSVEALNSLTGEFKGKYYPLKSMTEQEQ

QQLIDDHFLFDKPVSPLLLASGMARDWPDARGIWHNDNKSFLVWVN

EEDHLRVISMEKGGNMKEVFRRFCVGLQKIEEIFKKAGHPFMWNEH

LGYVLTCPSNLGTGLRGGVHVKLAHLSKHPKFEEILKRLRLQKRGT

GGVDTAAVGSVFDVSNADRLGSSEVEQVQLVVDGVKLMVEMEKKLE

KGQSIDDMIPAQK
``` http://www.uniprot.org/uniprot/F7BR99.fasta
http://www.uniprot.org/uniprot/F7BR99

When both CK and AST (which takes longer to rise, peak and return to normal) are measured, the inventors the inventors have determined that EER can be accurately diagnosed. Further, the response to treatment can be usefully monitored.

Levels of AST and CK for Use in Management of Lying Up'

Normal concentrations of CK differ from horse to horse and between different veterinary clinics, but blood levels below 200 units/l are generally considered normal.

The large study carried out by the inventors has shown that AST can be used as a late marker of ER at an activity level of 1000 units/l.

Further, the inventors have determined that a concentration of CK of 500 units/l in sport horses is acceptable and tying up is indicated at concentrations of 700 or 800 units/l and above. Horses should therefore be carefully monitored if levels rise above 500 units/l.

As such provided herein is a method of monitoring the presence of, severity of, progression of, or recovery from, equine exertional rhabdomyolysis in a horse, the method comprising
(i) determining the level of CK and AST activity in a blood sample over a period of time;
(ii) determining whether:
the activity level of CK is above or below 200, e.g. about 300, 400, 500, 600, 700, or 800 units/ml and/or
the activity of AST is above or below about 1000 units/ml, wherein
an activity level of CK:
of about 700-900 units/ml indicates risk of onset of equine exertional rhabdomyolysis, and of about 900-1100 units/ml indicates onset of equine exertional rhabdomyolysis, accompanied by an activity level of AST above or below 1000 units/ml indicates equine exertional rhabdomyolysis.

In one aspect the method comprises repeating the determination at intervals, whereby a reduction of the CK to below 500 from above 500, or a reduction of AST below 1000, indicates recovery from equine exertional rhabdomyolysis.

In one embodiment, an indication of equine exertional rhabdomyolysis, or the onset or risk of equine exertional rhabdomyolysis is followed by a treatment step. For example, the treatment step may comprising a period of rest for the horse.

In one embodiment, a determination of exertional rhabdomyolysis, or the onset or risk of equine exertional rhabdomyolysis is followed by examination of the training regime and/or nutritional plan of the horse to determine if any changes have been made which may have added to the onset of the episode.

In another embodiment the device is used to determine baseline CK and/or AST levels before a change in a training regime is implemented. CK and/or AST levels are then monitored after the change has been implemented to determine the effect on CK and/or AST levels and to assess the risk of the onset of an episode of exertional rhabdomyolysis e.g. in the event that CK rising to about 500-600 units/ml was determined.

In a further embodiment the device is used to determine baseline CK and/or AST levels before a change in the nutritional plan of a horse is implemented. CK and/or AST levels are then monitored after the nutritional change has been implemented to determine the effect on CK and/or AST levels and to assess the risk of the onset of an episode of exertional rhabdomyolysis e.g. in the event that CK rising to about 500-600 units/ml was determined.

In another embodiment CK/AST levels are monitored along with a training regime and/or nutritional plan to develop an exertional rhabdomyolysis management system whereby baseline levels of CK and/or AST are reduced.

In a preferred aspect of the invention the analysis of the two biomarkers is combined in a single device e.g. which is portable and held-held and indicates the concentration bands described above. Example devices for measuring two biomarkers such as CK and AST are described in more detail below.

Lateral Flow Devices and Other Preferred Embodiments

The analysis of any one of SAA, fibrinogen, CK and\or AST (or other analyte of interest provided through the use of the blood collection system) may be performed using any analytical device known in the art.

Described herein by way of non-limiting example is a lateral flow device (LFD) that can be applied to the measurement of levels of any or all the above indicators in bodily fluids, in particular to levels in blood.

In one embodiment the LFD provided herein incorporates a blood collection device which draws a blood sample into the LFD for subsequent analysis.

In other embodiments an LFD which does not incorporate a blood collection device can be used in conjunction with the BCS to assay other indicators in blood, for example IgG and other immune markers.

The LFD and the reader provided herein are, in preferred embodiments, inexpensive to produce and costs to the user are also reduced by the fact that there is no need for the samples to be sent to a laboratory. This, combined with the ease of use of the system, means that samples can be analysed much more frequently and quickly than is currently possible, which may be of great value.

A lateral flow assay device for the analysis of body fluid may thus comprise:
(i) a housing, and
(ii) a flow path, and (iii) optionally, a body fluid collector, which forms an integral part of the flow path.

As used anywhere herein, unless context demands otherwise, the term 'body fluid' may be taken to mean any fluid found in the body of which a sample can be taken for analysis. Examples of body fluids suitable for use in the present invention include, but are not limited to blood, urine, sweat and saliva. Preferably, the body fluid is blood. As described herein, the fluid may be diluted by a pre-determined amount prior to assay, and any quantification indicator on the LFD may reflect that pre-determined dilution.

Preferably, the devices, systems and methods described herein are for measuring analyte levels in equines such as horses (*Equus ferus caballus*), and find particular use with racehorses for monitoring health and anticipating performance, for sport horses, racehorses and foals for monitoring disease progression and response to treatment, and for newborn foals—as an infectious disease screening method. However, the skilled reader will appreciate that the embodiments described herein can equally be adapted for other animals, especially mammals including humans.

An integrated body fluid collector, where present on the LFD, may be continuous or contiguous with the flow path, allowing body fluid (e.g. blood) to be wicked directly from the subject (e.g.) horse into the lateral flow device by capillary action. In other words, the body fluid collector enables a body fluid sample (e.g. blood) to be analysed by simply contacting a drop of (e.g.) blood on the body (e.g. gum, lip or skin) of the horse with the body fluid collector. By contrast, many lateral flow devices are designed to receive a sample by pipetting it onto a sample port.

Further, the lateral flow devices described herein may be are capable of operating in any orientation. By contrast, most commercial assays require a flat surface for test operation.

Some aspects of the device will now be discussed in more detail:

Flow Path of LFD

The flow path (e.g. a chromatographic strip) is preferably provided by a carrier, through which the test substance or body fluid can flow by capillary action. In one embodiment, the carrier is a porous carrier, for example a nitrocellulose or nylon membrane. In a further embodiment, sections or all of the carrier may be non-porous. For example, the non-porous carrier may comprise areas of perpendicular projections (micropillars) around which lateral capillary flow is achieved, as described in for example WO2003/103835, WO2005/089082 and WO2006/137785, incorporated herein by reference.

The flow path will typically have an analyte-detection zone comprising a conjugate release zone and a detection zone where a visible signal reveals the presence (or absence) of the analyte of interest. The test substance can be introduced into the LFD by direct contact with the mouth of the body fluid collector, and flows through to the detection zone.

Preferably the carrier material is in the form of a strip, sheet or similar to the material described in WO2006/137785 to which the reagents are applied in spatially distinct zones. The body fluid sample is allowed to permeate through the sheet, strip or other material from one side or end to another.

Analyte Detection Methods

Analyte detection may be based on competitive or sandwich (non-competitive) assays. Such assays may be used to detect, SAA, or CK and AST, as described herein.

The conjugate release zone contains freely mobile specific binding partners to the analyte of interest. For example, if the analyte is an antigen, its binding partner may be an antibody. For example, the antibody may bind any one of SAA, fibrinogen, CK or AST. Alternatively, the conjugate release zone may comprise reagents for carrying out a particular assay to enable detection of the analyte, as described herein.

The binding partners may be attached to a mobile and visible label. A "label" is a composition detectable by spectroscopic, photochemical, biochemical, immunochemical, electrical, optical or chemical means. Useful labels in the present invention include magnetic beads (e.g., Dynabeads™), fluorescent dyes, radiolabels, enzymes, and colorimetric labels such as colloidal gold, silver, selenium, or other metals, or coloured glass or plastic (e.g., polystyrene, polypropylene, latex, etc.) beads. Preferred is a gold colloid or latex bead.

If the analyte is present in the sample, it will bind to the labelled binding partners. In preferred embodiments the intensity of the colour may be directly proportional to the amount of analyte. Here the detection zone comprises permanently immobilised unlabelled specific binding reagent for the same analyte. The relative positioning of the labelled binding partner and detection zone being such that a body fluid sample applied to the device can pick up labelled binding partner and thereafter permeate into the detection zone. The amount of bound label can be detected as a visible signal in the detection zone.

The label in the LFD will be quantifiable by conventional means or as described herein.

In one competitive format embodiment, the detection zone contains regions of immobile analyte-protein derivatives. These bind and immobilise any of the labelled binding partners not already bound by the analyte in the sample, producing a coloured line or stripe. In this case the amount of label bound in the detection zone (and hence the intensity of the coloured stripe) will be inversely proportional to the amount of analyte in the sample.

In another competitive format, a labelled analyte or analyte analogue may alternatively be provided and this is detected using immobilized specific binding partner (e. g. immobilized antibody specific for the analyte) in the detection zone.

In another competitive format, a labelled analyte or analyte analogue is provided along with a specific binding partner (e.g. an antibody specific for the analyte). The resulting mixture is conveyed to the detection zone presenting immobilized binding partner of the analyte or analyte analogue. The higher the amount of analyte in the sample, the higher the amount of free labelled analyte which leaves the conjugate release zone to be detected in the detection zone.

In one LFD which may be used, the flow path has:
(a) optionally, a body fluid collector for transferring a sample of the body fluid into the flow path by capillary action;
(b) optionally, a blood filter, integrated into the body fluid collector or positioned in the flow path downstream of the body fluid collector;
(c) a carrier along which the body fluid is capable of flowing by capillary action, wherein the carrier is positioned in the flow path downstream of the body fluid collector, the carrier comprising:

(i) an analyte-detecting means, capable of providing an assay result indicative of the presence of the analyte; and (ii) optionally a control zone, positioned on the carrier upstream or downstream of the analyte-detecting means, capable of indicating the assay has been successfully run;

Control Zone

Preferably the LFD for use with the present invention contains a control zone, which may be located after the detection zone in the direction of sample flow, in which excess labelled binding partner binds to produce a visible signal showing that the test has been successfully run.

Alternatively or additionally, a control zone may be located before the detection zone in the direction of sample flow, indicating that enough sample has been collected to allow operation of the test.

In one embodiment, the control zone is used as a reference point for a reader (see below).

In an example of another control zone, control reagents could be chosen which display similar characteristics to the analyte (e.g. SAA) test line in terms of time to appear.

Integral Body Fluid Collector

Where the LFD integrates its own body fluid collector, this may have a housing made of any material, and the capillary channel is located within this housing. Preferably, the housing is transparent or partially transparent. This enables user feedback during sample collection, enabling the user to determine if body fluid has been drawn into the LFD. In one embodiment, the body fluid collector housing is integrated with the housing of the LFD.

In one embodiment, the body fluid collector may have a mouth is positioned in a flat wall in the housing of the LFD and a channel to enable the desired volume of fluid to be drawn into the LFD.

Preferably, the mouth of the channel is between about 2 and 30 mm wide and between about 1 and 10 mm high. Preferably the mouth is substantially rectangular. In one embodiment, the mouth is about 2, 3, 4, 5, 6, 7, 8, 9, 10, 11, 12, 13, 14, 15, 16, 17, 18, 19, 20, 21, 22, 23, 24, 25, 26, 27, 28, 29 or 30 mm wide. The mouth may be about 1, 2, 3, 3.5, 4, 5, 6, 7, 8, 9 or 10 mm high. The capillary mouth thereby allows rapid collection in case the horse moves during sample collection. In one preferred embodiment, the mouth is between about 5 and 15 mm wide and 2 and 8 mm high. In one embodiment the mouth is 8 mm wide and 0.5 mm high.

Further, the broad opening allows the device to come into contact with a larger area of tissue. The broad opening also transports the sample across a large surface area allowing for a faster wicking rate from the tissue surface. The broad opening tapering to narrow exit further enhance capillary force, altogether reducing sample exposure time and improving reliability and consistency. These points combined increase capillary flow, reduce sample exposure time and improve reliability and consistency.

The body fluid collector may collect a metered or unmetered volume of blood.

An integral collector may have any of the structural characteristics of the BCS described above, in terms of channel and wall alignment, and dimensions and structures.

Two or More Analytes

In various aspects of the invention, the LFD may be capable of detecting two (or more) different analytes e.g. CK and AST.

In one embodiment, the two analytes are analysed using two distinct flow paths. Preferably, each flow path will have a distinct body fluid collectors. Preferably, the housing of the LFD houses the two flow paths.

For example, the flow path may comprise two or more carriers. The carriers may be positioned along the flow path consecutively. In use, body fluid would flow along each carrier sequentially.

In a further embodiment, two or more carriers may be positioned in the flow path in parallel. In use, body fluid would flow along each carrier simultaneously. Each carrier may still be in fluid connection with a single body fluid collector.

In a further embodiment, the lateral flow device may comprise two flow paths.

In one embodiment, the analyte-detecting means may comprise a first binding reagent that specifically binds the analyte and a second binding reagent that specifically binds the analyte, wherein the first binding reagent is labelled and is movable through a carrier under the influence of a liquid by capillary flow and the second binding reagent is immobilised at a detection site in the flow path. The analyte-detecting means comprises a labelled, mobile antibody, specific for the analyte and an immobilised unlabelled antibody, specific for the analyte.

In one embodiment, the analyte-detecting means for each analyte may be positioned together on the carrier, but the specific analyte-binding reagent for each different analyte may comprise a different label. The different labels will be capable of being distinguished as described herein or by conventional means.

Alternatively, the analyte-detecting means for each analyte may be spatially distinct. The flow path in the 'multiplexed' LFD may incorporate two or more discrete carriers of porous or non-porous solid phase material, e.g. each carrying mobile and immobilised reagents. These discrete bodies can be arranged in parallel, for example, such that a single application of body fluid sample to the device initiates sample flow in the discrete bodies simultaneously. The separate analytical results that can be determined in this way can be used as control results, or if different reagents are used on the different carriers, the simultaneous determination of a plurality of analytes in a single sample can be made. Alternatively, multiple samples can be applied individually to an array of carriers and analysed simultaneously.

Preferably, multiple analyte detection zones may be applied as lines spanning or substantially spanning the width of a test strip or sheet, preferably followed or preceded by one or more control zones in the direction of body fluid travel. However, multiple analyte detection zones may also, for example, be provided as spots, preferably as a series of discrete spots across the width of a test strip or sheet at the same height. In this case, a one or more control zones may again be provided after or before the analyte detection zones in the direction of body fluid travel.

Preferred Combined CK and AST Device

In one aspect of the invention there is provided an LFD device for monitoring the presence of, severity of, progression of, or recovery from, equine exertional rhabdomyolysis in a horse, which device comprises means for determining whether levels of CK are above or below 200 units/l or in excess of 300 units/l or 400 units/l or 500 units/l or 600 units/l or 700 units/l or 800 units/l, up to 3500 units/l and/or whether levels of AST are above or below about 1000-3500 units/l.

As explained in Example 7, a preferred LFD has
(i) a housing having a sample port, and
(ii) at least one flow path or channel which includes a carrier through which the test substance or body fluid can flow from the sample port by capillary action,
  wherein the flow path has:
  an analyte-detection zone comprising a conjugate release zone and a detection zone where a visible signal reveals the presence of each analyte of interest.
  optionally a control zone, positioned on the carrier upstream or downstream of the analyte-detecting means, capable of indicating the assay has been successfully run;

The flow path may comprise two or more carriers. The carriers may be positioned along the flow path consecutively. In use, body fluid would flow along each carrier sequentially.

In a further embodiment, two or more carriers may be positioned in the flow path in parallel. In use, body fluid would flow along each carrier simultaneously. Each carrier may still be in fluid connection with a single sample port.

In a further embodiment, the lateral flow device may comprise two flow paths.

In one embodiment CK and AST concentrations in particular are determined by colourimetric enzymatic means on a chromatographic strip.

In one embodiment, the result of the determination is indicated by the presence and intensity or absence of a coloured test line for CK and AST. The presence and intensity of the coloured test line can be used to monitor the increase or decrease of CK and AST and therefore the onset of and recovery from exertional rhabdomyoysis. The housing may comprise an indication of which test line corresponds to which analyte.

LFD Reader

When using LFDs in performance of the present invention, the intensity of the signal in the detection zone may be converted to a quantitative reading of the concentration of analyte in the sample. It is therefore preferred that the LFD can be used in conjunction with a screening device (reader). The reader is preferably a handheld electronic device into which the LFD cartridge can be inserted after the sample has been applied.

The reader comprises a light source such as an LED, light from which illuminates the LFD membrane. The reflected image of the membrane may be detected and digitised, then analysed by a CPU and converted to a result which can be displayed on an LCD screen or other display technology (or output via a conventional interface to further storage or analytical means). A light-dependent resistor, phototransistor, photodiode, CCD or other photo sensor may be used to measure the amount of reflected light. The result may be displayed as positive or negative for a particular analyte of interest or, preferably, the concentration of the particular analyte may be displayed. More specifically the conventional reader comprises: illuminating means for illuminating an immunoassay test; photosensitive detector means for detecting the intensity of light from the illuminating means which is reflected from the immunoassay test; means, coupled to the output of the photosensitive detector means, for representing the intensity of the detected light by a data array; memory means for storing preset data; first data processing means, coupled to the memory means and to the output of the means for representing the intensity of the detected light by a data array, for segmenting the data array according to the preset data into control data, background data and test data; second data processing means, coupled to the first data processing means, for determining whether the test data exhibits a statistically significant result; and output means, coupled to the output of the second data processing means, for outputting the results from the second data processing means.

In embodiments of the present invention where multiple analytes are assessed, the reader may analyse the results to detect a plurality of spatially distinct detection or test zones pertaining to different analytes. The photosensitive detector means (e.g. light dependent resistor, phototransistor, photodiode, CCD or other light sensor) will therefore detect reflected light from all of these (optionally scanning them) and generate a discrete or segmented data stream for each zone. Respective control zonal data and background zonal data may also be gathered for the different analytes.

The colour of the LED or other source may vary dependent on the label or method of detecting the analyte.

For gold-labelled analytes, a white LED may be preferable, and therefore a reader may comprise both a red and white LED.

Other Detection Systems

Figure 13:
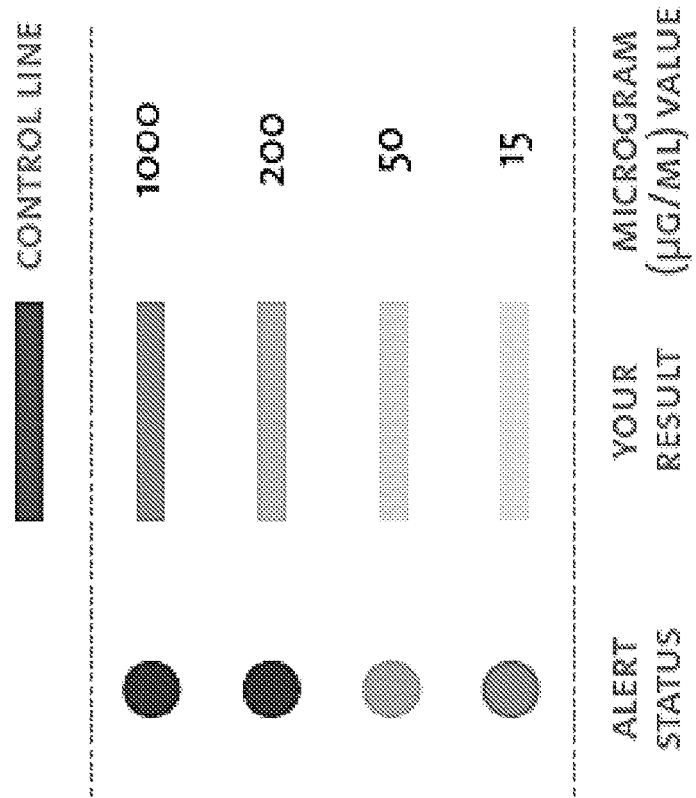

Alternatively, the intensity of the signal in the detection zone may be determined by eye, for example by comparison to a reference chart or card. Provided herein is a reference card which enables the concentration of the analyte or analytes, e.g. SAA, to be determined by comparison of the signal intensity in the detection to the reference card. Preferably, the reference card displays the signal intensity for the ranges of SAA described herein, e.g. 15, 50, 200 and 1000 μg/ml. Preferably, the reference card shows a control line signal intensity, i.e. the visible signal showing that the test has been successfully run. An example reference card is shown in FIG. 13.

One aspect of the invention provides a kit comprising an LFD of the invention as described herein and a reference card as described herein.

Other Components

In a further embodiment the LFD comprises a blister pack or pouch containing a buffer. The buffer may be released, for example by compressing an indicated area of the LFD, following sample application. The released buffer encourages sample flow through the flow path, as known in the art. Alternatively, a buffer may be added manually, for example by pipette.

In embodiments where a buffer is not used in a pouch/blister pack or added manually by pipette, then the flow path may contain reagents in a dried form which, when wetted, aid flow or generally improve the performance of the test. Such reagents may be positioned for example in or downstream of the body fluid collector, or in the carrier, for example in the conjugate release zone. Such reagents may comprise Tween 20, PEG, Polyvinylpyrrolidone (PVP), BSA, or a combination of these and/or other known detergents.

In some embodiments, a hydrophilic tape such as ARflow® 90128, described in WO 02/085185 A2 (incorporated by reference herein) is incorporated into the flow path to further encourage flow.

FIGURES

FIG. 1: Lateral flow assay device with integrated body fluid collector

Figure 2:
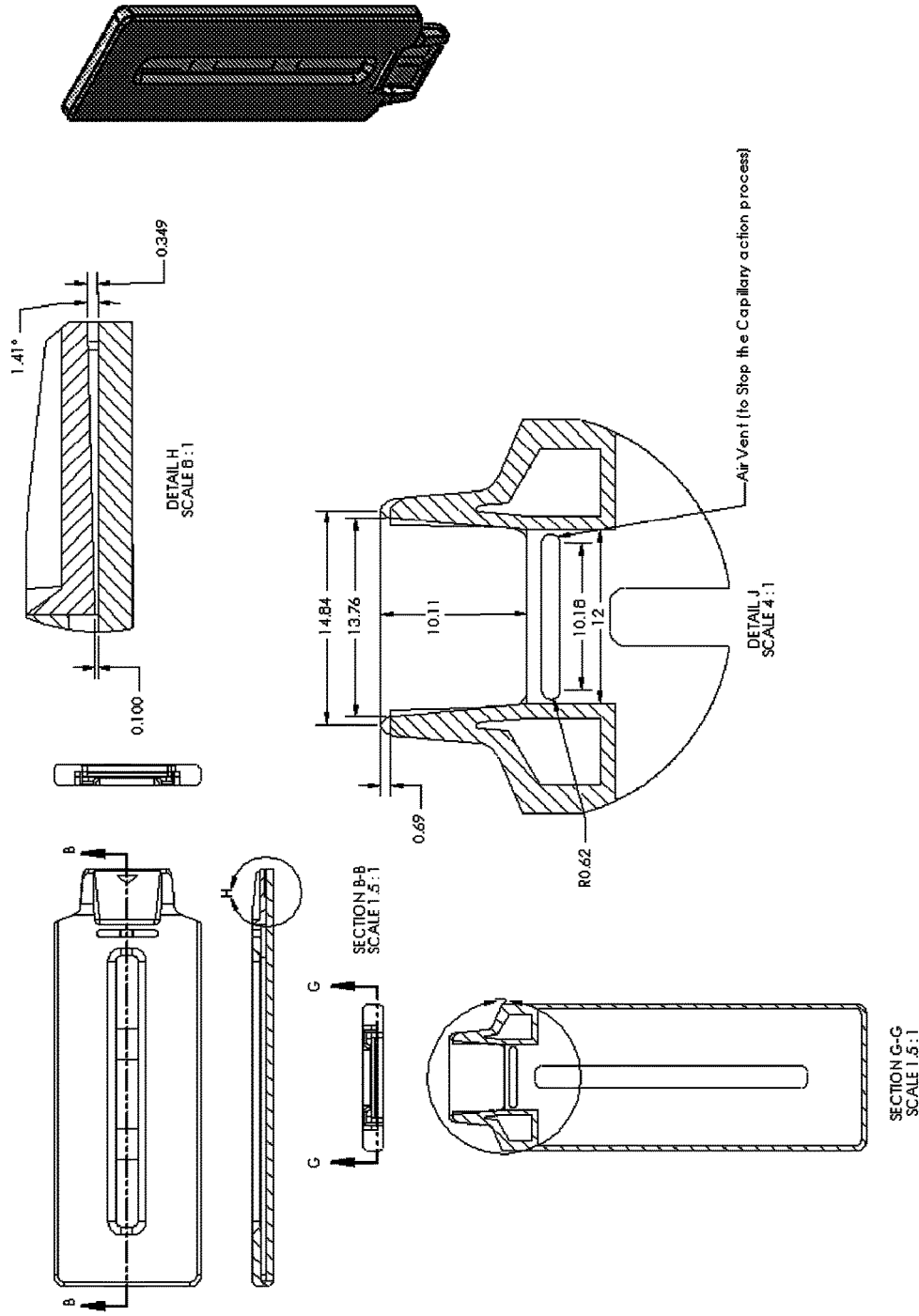

FIG. 2: Lateral flow assay device with integrated body fluid collector

Figure 3:
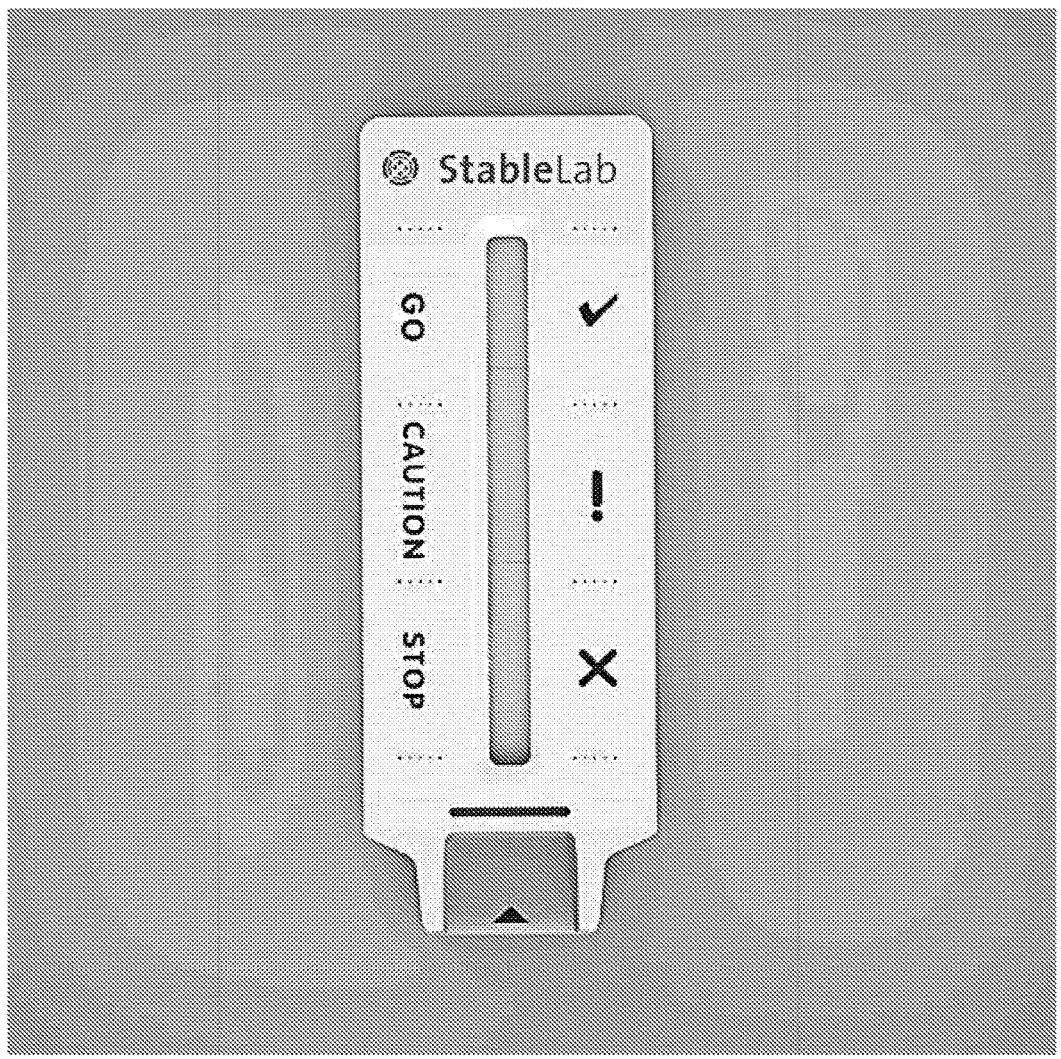
Figure 4:
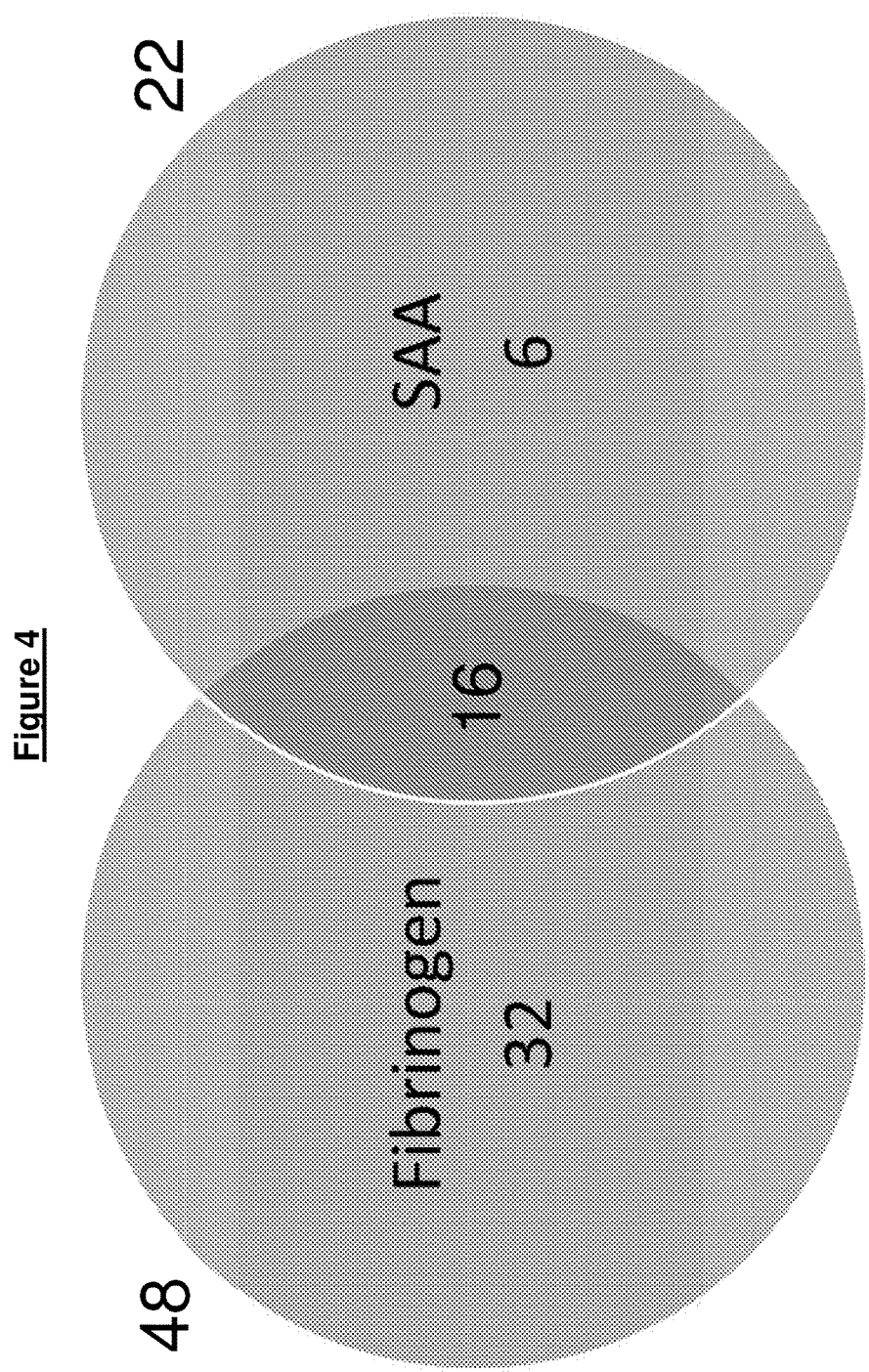
Figure 5:
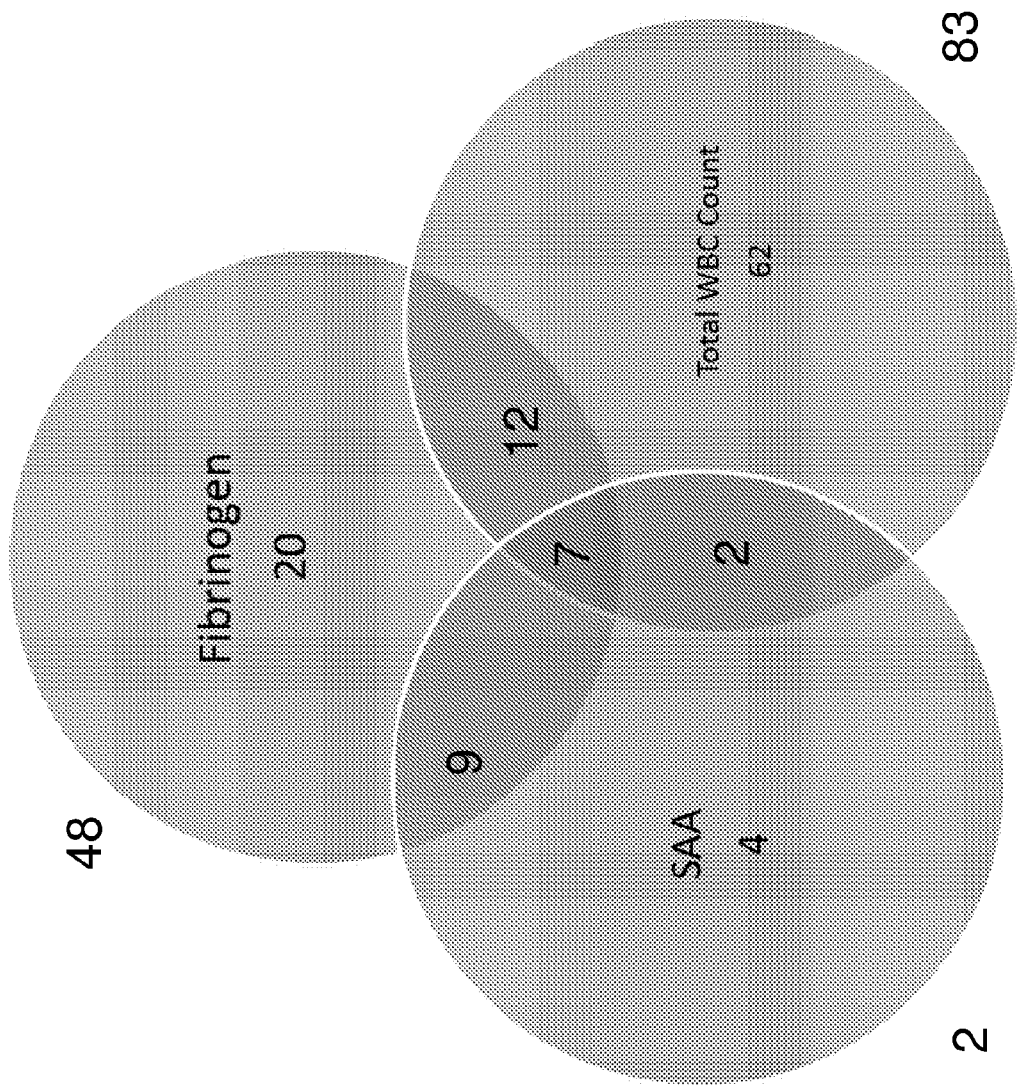
Figure 6:
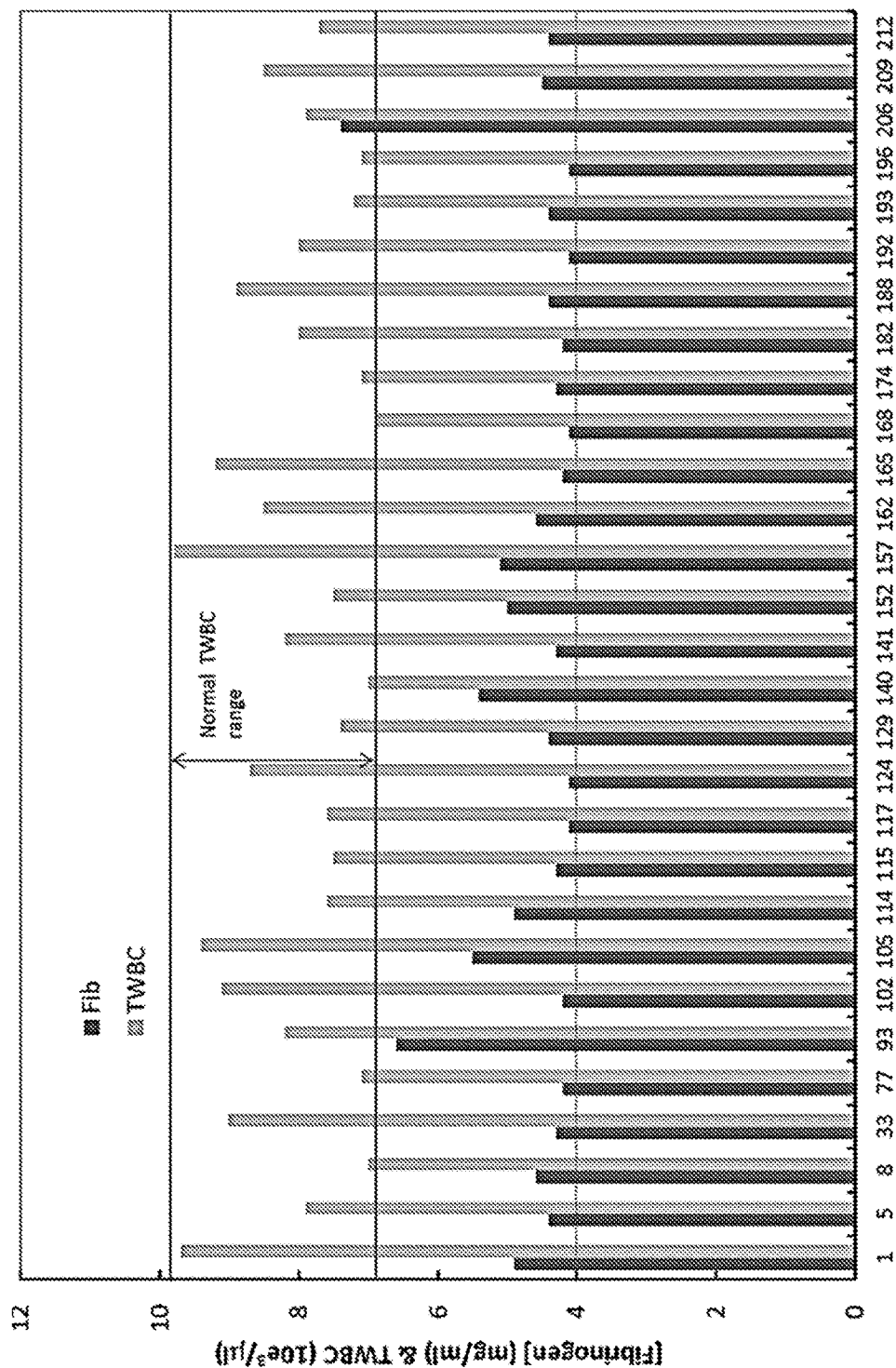
Figure 7:
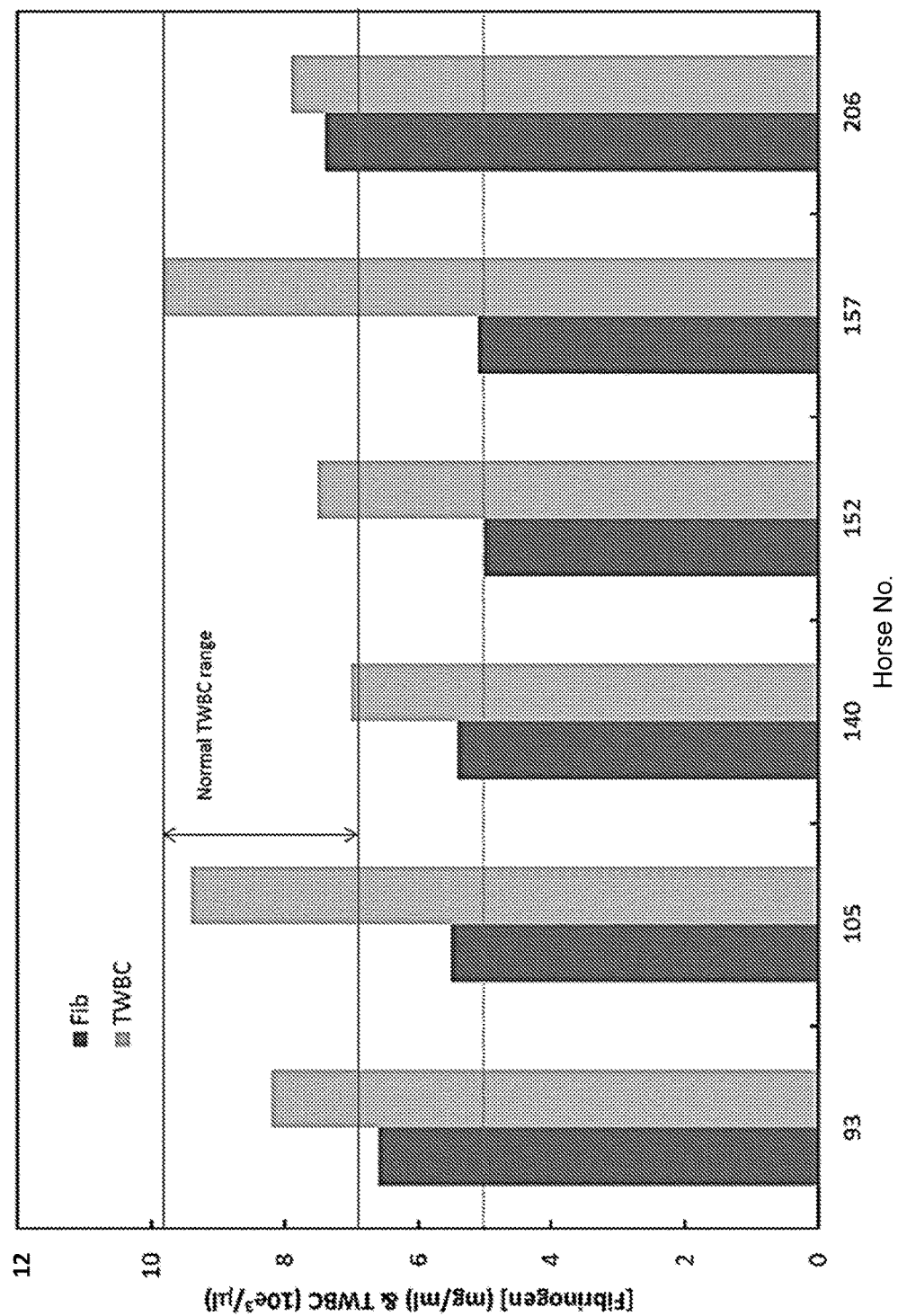
Figure 8:
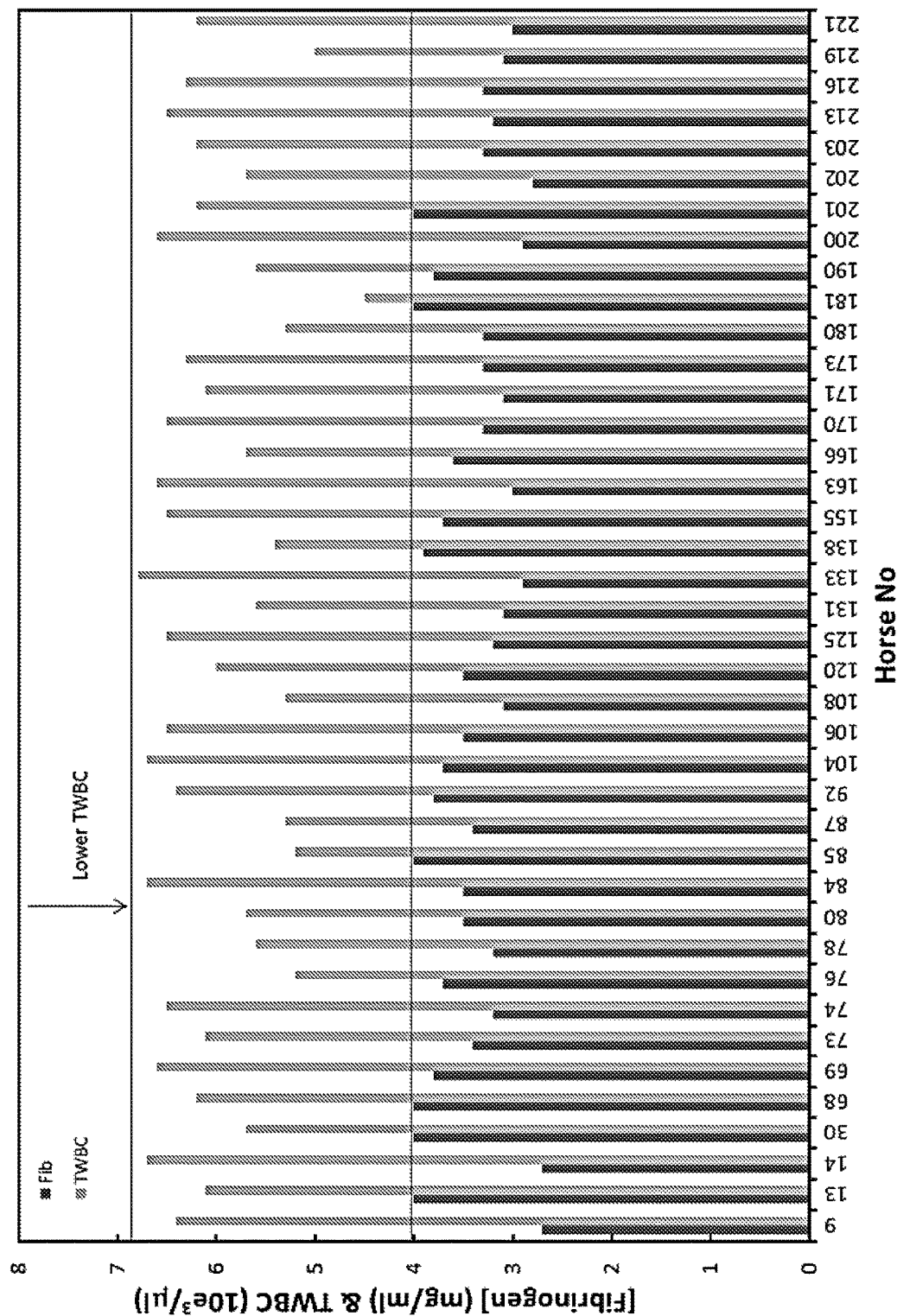
Figure 9:
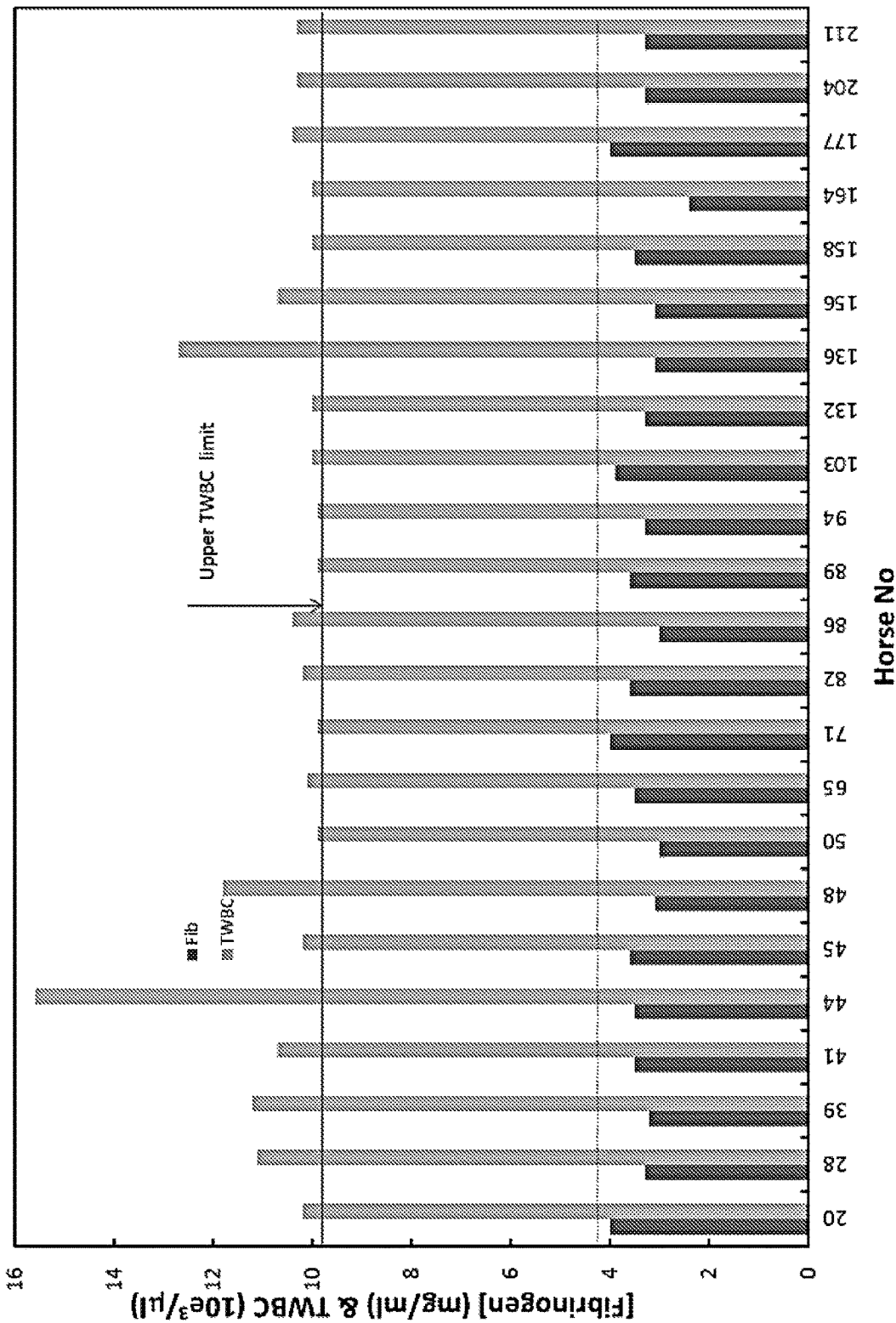
Figure 10:
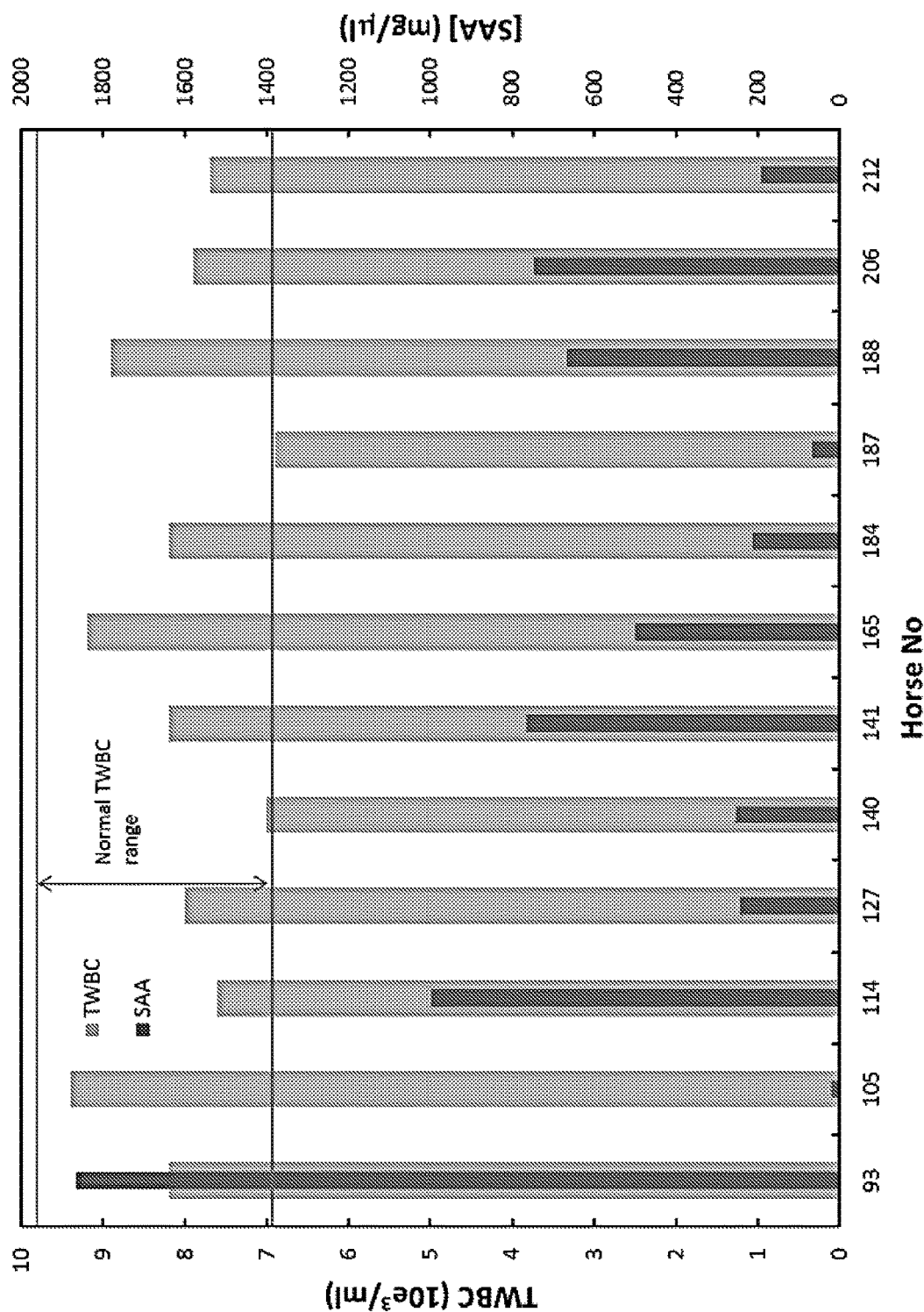

FIG. 3: Lateral flow assay device with a traffic light system of go, caution and stop FIG. 4: Correlation of elevated fibrinogen and elevated SAA to each other FIG. 5: Relationship between elevated Fibrinogen, elevated SAA and abnormal total white blood cell count FIG. 6: Elevated Fibrinogen and Total White Blood Cell Count Correlation FIG. 7: Highly Elevated Fibrinogen (>5 mg/ml) and Total White Blood Cell Count Correlation FIG. 8: Correlation between normal fibrinogen and low total white blood cells FIG. 9: Correlation between normal fibrinogen and high total white blood cells FIG. 10: Relationship between elevated SAA and normal total white blood cells FIG. 11: Correlation between SAA levels and horses which performed as expected and those that did not. All but one horse performed as expected when SAA was measured at 7.5 μg/ml or below.

Figure 12:
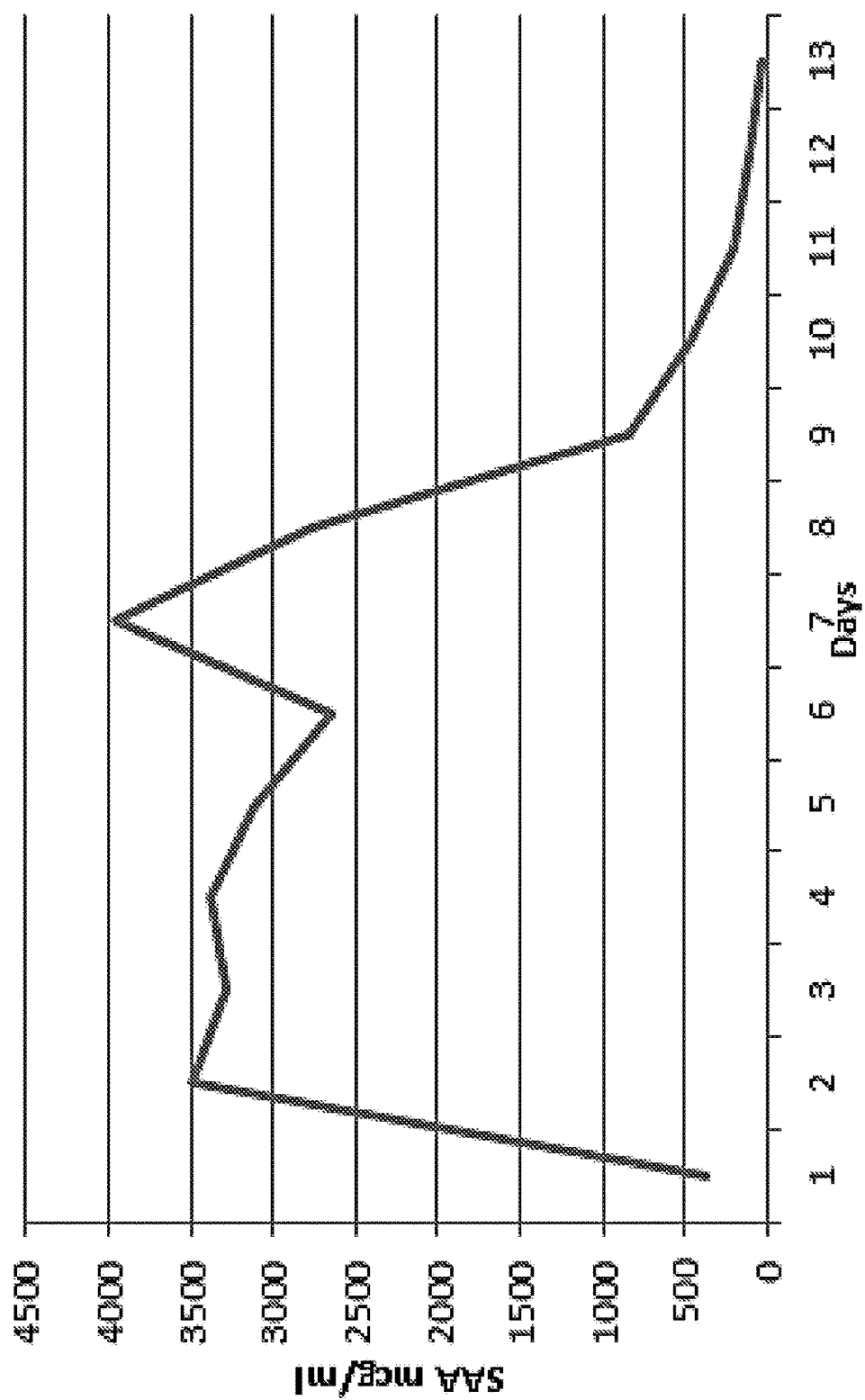

FIG. 12: SAA concentrations during the recovery of a horse diagnosed with travel sickness.

FIG. 13: Example reference card for determining SAA levels.

FIG. 14: Test fluid collection system according to the present invention.

Figure 15:
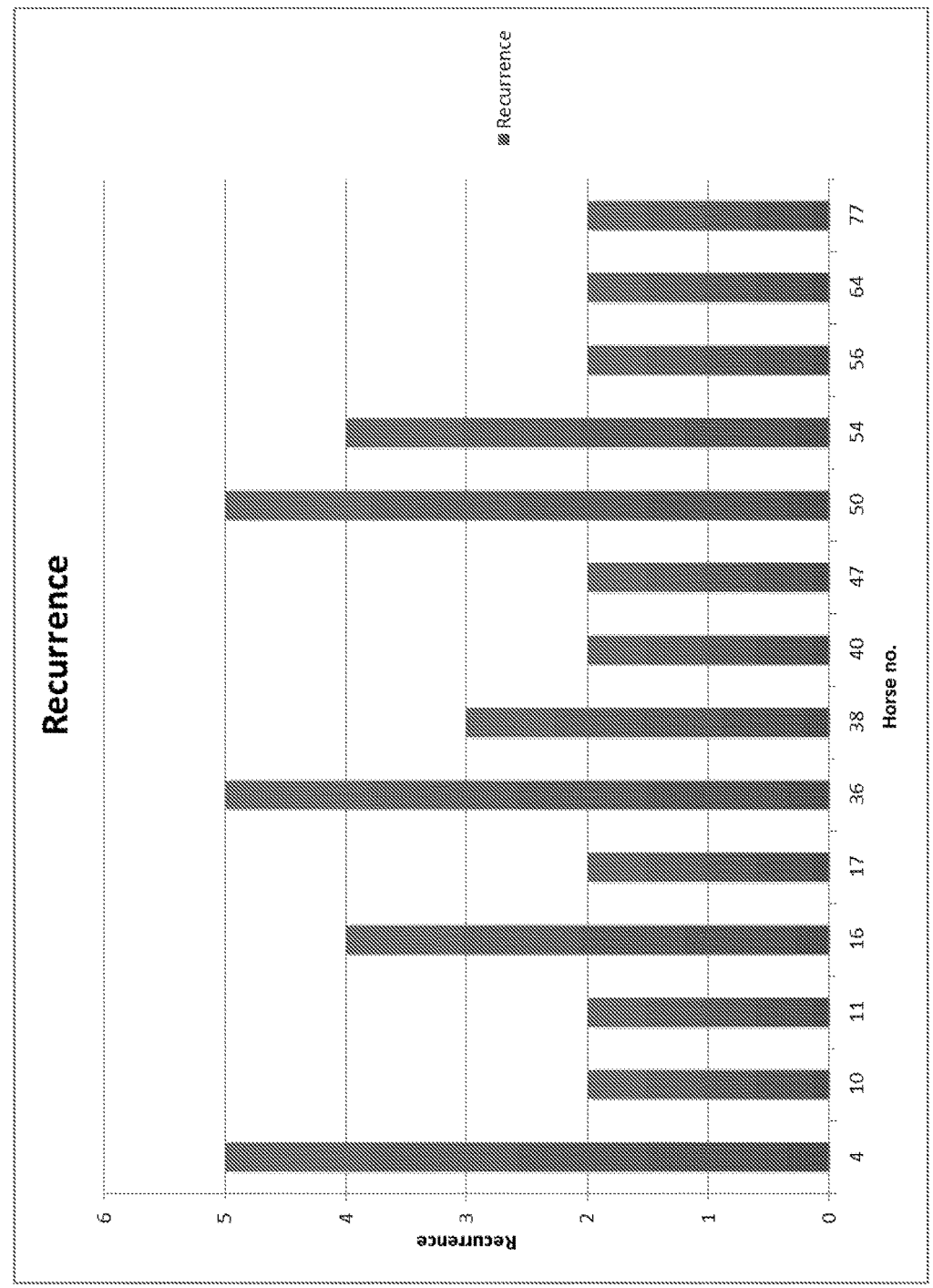

FIG. 15: Bar chart showing recurrence of "tying up" in a horse population tested in Example 7.

Figure 16D:
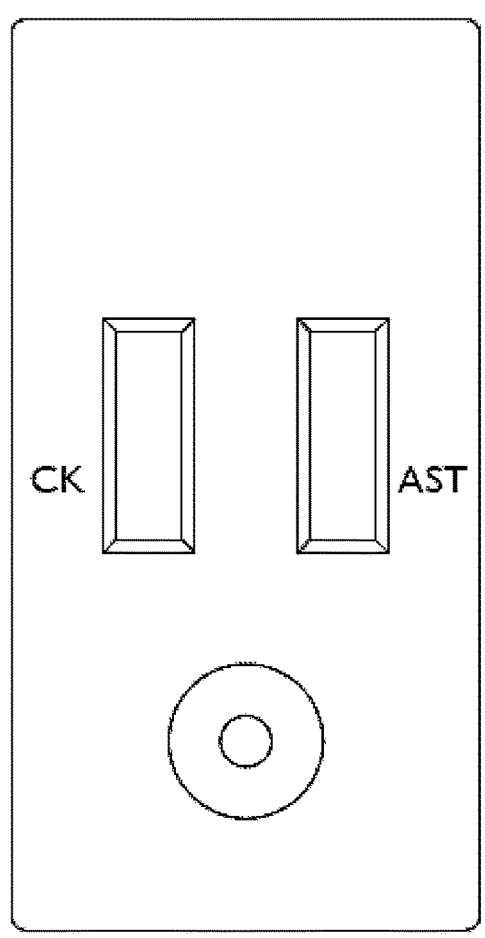

FIG. 16: Examples of devices for monitoring "tying up" by assay of CK and AST.

FIG. 17: SAA concentrations determined in horses during infection, compared with other indicators. This demonstrates the significant utility of SAA as a prognostic or diagnostic marker.

The invention is described herein by way of example and not limitation, by reference to the accompanying drawings. Many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. All documents cited herein are expressly incorporated by reference.

EXAMPLES

Example 1

1. Introduction

Racing thoroughbred horses have been selectively bred to produce optimal performances of speed and endurance on the race track. In order to achieve athletic excellence the horse must undergo a rigorous exercise programme. Just as human athletes strive to find the right balance between training hard enough to maximise performance but not so hard that stress induces either injury or a compromised immune system, so too with the horse trainers [1]. Since clinical symptoms in horses may only appear when over-stressing has already occurred, methods to determine imminent problems at sub-clinical stages are at a premium. Current methods of detecting when health is becoming compromised focus on blood biomarkers. Of three current measures, red blood cell counts, white blood cell counts and blood biochemistry, the most commonly used is total white cell count, usually coupled with estimates of the relative abundance of the five main types of white cell, the neutrophils, lymphocytes, monocytes, eosinophils and basophils. White cell counts can change rapidly in response to adverse health but the changes tend to be transient and to differ depending on the stimuli. For example the total white cell count may decrease to below normal in response to acute inflammation or virus attack but may increase in response to prolonged inflammation or bacterial infection [2]. Similarly, neutrophils, which normally make up 60% of the total white cells, may decrease quickly in response to acute stress but increase quickly when fighting acute infection [3]. Nonetheless, neutrophil and lymphocyte counts can be used to diagnose airway inflammation disease and recurrent airway obstruction [4] using bronchoalveolar lavage.

Although the various white cell counts have the potential to indicate a range of common conditions, there are a number of important issues. First, and most importantly, changes in white cell numbers can occur for reasons other than disease or injury, such as being agitated at the time of blood collection. Second, base levels are rather variable, with younger thoroughbreds in particular differing greatly in their white cell counts from one week to another without any evidence of infection or inflammation [5]. Third, the fact that cell number can go down as well as up may cloud the interpretation of tests where multiple opposing stimuli are present. For these reasons, trainers often treat white blood cells with skepticism as being too difficult to understand and too variable to provide a reliable indicator of a horse's overall health profile.

A more reliable tool should aim to reflect specifically the changes in blood biochemistry that occur at the onset of stress. When an animal suffers tissue injury, acute phase proteins are produced in the liver and released into the bloodstream and the result is localised inflammation. Similar responses are noted for a wide range of conditions including trauma, arthritis, surgery or bacterial, viral and parasitic infection [6,7,8] indicating that the acute phase response is generic and may be mounted to any form of tissue damage. Acute phase proteins thus appear a logical target for an improved test for stress-related injury during training. Two promising candidate proteins are fibrinogen, which has been the most commonly measured acute phase protein for some time, and serum amyloid A (SAA), which is becoming increasingly popular as a diagnostic of acute infection.

Fibrinogen is a plasma glycoprotein synthesised by the liver and is converted by thrombin into fibrin during blood coagulation. Fibrinogen is normally present at between 2-4 mg/ml but this rises following inflammation regardless of the cause. Indeed, fibrinogen may be the sole indicator of inflammation [9, 10, 11,]. Elevated levels of fibrinogen may indicate chronic inflammation or reflect the progression of an infection [12]. Novel inflammation causes the level of fibrinogen to increase above normal within 24-48 hours and in proportion to the degree of inflammation, and remain elevated for up to 10 days [13]. This relatively rapid response means that fibrinogen elevation may occur before clinical symptoms of illness [14, 15].

Serum Amyloid A (SAA) is a second acute phase protein that is also produced in the liver. Normal levels in healthy horses are very low but increase rapidly to peak 24-48 hours after infection [16]. Circulating SAA concentrations may increase up to 100 fold in response to an infection [13] but it disappears rapidly after the infection has abated [17], making it an excellent 'real time' diagnostic tool for tracking progression and recovery. Previous studies have shown that elevated SAA may also be used for detecting the presence of inflammatory disease of the airways [6], gut [18] and musculoskeletal system [7, 19]. As with fibrinogen, the severity of the inflammation is reflected in the degree of elevation of SAA.

The purpose of the current study is to investigate the relationship between classic white cell counts and the two indicators of an inflammatory response, fibrinogen and SAA across a large sample of thoroughbred horses in training. We find evidence that WBC, fibrinogen and SAA capture different aspects of a horse's physiology. WBC counts fluctuate across a rather narrow range and correlate well with parallel changes in many elements of blood chemistry, suggesting that they track normal homeostatic fluctuation. In contrast, fibrinogen and SAA tend to vary little except in a small subset of horses where both markers tend to show markedly elevated levels.

2. Materials and Methods

A population of thoroughbred horses bred for flat racing were screened at two random dates, once at the beginning of the racing season (1-2 May '12 n=105) and once at the end of the racing season (2-3 Sep. '12 n=118). The horses were a random mixture of males and females, a mixture of grades, ranging in age from 2 to 5 year old and had raced a maximum of 5 times each. All horses are managed in the same way with individual boxes, photoperiod of 4:30 am to 9 pm, a natural indoor temperature (18 to 20° C.) and the same feeding and training schedules. The horses underwent one workout of approximately 20-30 minutes per day between the hours of 6 am and 10 am. The horses were allowed to rest for a period of 4-7 hours post exercise before blood draw. Detailed veterinary analysis of each horse immediately post sampling would be desirable but was beyond the scope of the current study. The horses names, existing injuries, illnesses and medications were not recorded, however it was noted by the veterinarian that all horses were fit for work. A large degree of overlap between the 2 sets of horses tested is expected. The complete blood count consists of the red cell series (Red Blood Cell (RBC) Count, Hemoglobin (Hgb), Hematocrit (Hct), Mean Corpuscular Volume (MCV), Mean Corpuscular Hemoglobin (MCH), Mean Corpuscular Hemoglobin Concentration (MCHC), platelets (Plt) and the white cell series (Total White Blood Cells, Neutrophils (Neut), Lymphocytes (Lymph), Monocytes (Mono), Eosinophils (Eosin) and Basophils (Baso)). The red series and the white cells were assayed using a calibrated Advia 2120 (Abbott) analyser.

In addition to cell counts we also monitored a range of blood chemistry components: Fibrinogen, Serum Amyloid A, Creatine Kinase (CK), Aspartate Amino Transferase (AST), Urea, Creatine (Creat), Total Protein (TotP), Glutamate Dehydrogenase (GLDH), Gamma-Glutamyl Transaminase (GGT), Alkaline Phosphatase (ALP), Lactose Dehydrogenase (LDH), Globulin (Glob) and Albumin (ALB). The fibrinogen was measured using a calibrated ACL Elite analyser from Instrumentation Laboratory. SAA was measured using a calibrated Konelab 20 instrument from Thermo Scientific with the 'Eiken' Serum Amyloid A test reagents supplied by Mast Diagnostic. The Eiken assay is a human immunoturbido metric method which has been previously validated in horses [20]. According to the manufacturer the range of the test is 5-500 ug/ml with a coefficient of variation for less than 10% and an accuracy of 85-115% when a known concentration is measured. The measurement of 57 samples reported a correlation coefficient (r) as r=0.981 and the regression line as y=0.971x+2 [21].

All tests were performed by the suitably qualified in-house lab technician. To minimise the impact of circadian fluctuations and to allow for horses to return to the resting state, blood was drawn between 2 pm and 3 pm according to in-house procedures and veterinary recommendation by the in-house vet. The blood was drawn into blood tubes appropriate for the parameters to be tested. The results for each of the parameters under analysis in this study for each of the 223 horses were compiled and analysed using Microsoft excel.

3. Results

The three primary measures obtainable from blood that we were most interested in were the classical total white cell count and two proteins associated with the inflammatory response, fibrinogen and SAA. We began by asking whether, across the entire range of observed values, there was a general tendency for high and low values in one measure to be associated with high and low values in another. Since several of the trait value distributions were strongly non-normal we used non-parametric rank correlation tests rather than a standard Pearson correlation.

Rank correlations between our three primary measures and all other traits are presented in Table 1. Among the three primary measures, the two indicators of inflammation correlate positively and highly significantly with each other, but there is no association between either of these and WBC. As might be expected, WBC counts are positively correlated with many of the other sub-classes of blood cell counts, particularly neutrophils, lymphocytes and red blood cells. Among the blood chemistry measures, WBC is associated with GLDH and ALP, while the inflammation proteins both correlate with total protein and globulin, but also exhibit weak correlations with several others. Red blood cells are interesting, since they correlate positively with WBC and SAA but negatively with fibrinogen.

From the point of view of diagnosing imminent health issues, weak correlations between two or more measures across all horses may or may not be biologically relevant. For example, mild dehydration might result in transiently higher protein concentrations across many/most molecules, and this could drive correlations even across a sample of equally healthy animals. More clinically relevant, therefore is the tendency for measures to show concordance when levels have risen outside what might be considered the 'normal' range of values. We first explored published tables giving the 'normal ranges' for different classes of horse (e.g. 'thoroughbreds' or '2 year olds in training') but several traits in these systems were in contradiction with one another and routinely yielded values outside the expected ranges depending on which reference method was applied. Consequently, we turned to a more unbiased approach. We arbitrarily assumed that the highest 15% of observed values for each parameter were 'elevated' and used simple chi-squared tests to ask whether these elevated values at our three focal variables tended to be associated with elevated values in each of the other traits. 15% was chosen as a balance between a lower fraction that would have too little statistical power and a higher fraction that might be deemed unrealistic. This method therefore bypasses the need to predefine 'normal' and 'abnormal'.

The chi-squared tests for concordance of high values are summarised in Table 2. With (overly) stringent full Bonferroni correction for conducting 63 tests, four tests are significant experiment-wide: Fib v SAA ($X^2$=43.7, 1df, P=1.4×$10^{-11}$), WBC v Neutrophils ($X^2$=27.9, 1df, P=1.3×$10^{-7}$), WBC v Lymph ($X^2$=13, 1df, P=3.2×$10^{-4}$) and WBC v ALP ($X^2$=11.4, 1df, P=7.5×$10^{-4}$). In addition, a number of other combinations yield significance at P=0.05 uncorrected, noticeably Total Protein, Neutrophils and Globulin, which all show associations with all three of our primary measures. It is reassuring that the strongest association, using both statistical models, by some way is the one between fibrinogen and SAA, the two measures of the inflammatory response. In all cases the associations are positive, in that the highest values for one trait occur disproportionately frequently with high values at another trait.

TABLE 1

Correlation between values in diverse blood assays in 224 thoroughbred racehorses. Two proteins associated with the inflammatory response, Serum Amyloid A and Fibrinogen, and total White Cell Count are compared against each other and against 20 other cell count/protein assays. In each case a non-parametric Spearman rank correlation is performed. Values presented are the resulting P-values. Values significant at P < 0.05 are indicated with one asterisk, those significant experiment-wide are indicated with two asterisks. Assay abbreviations are found in methods.

|  | Fibrinogen | SAA | WBC |
|---|---|---|---|
| SAA | $1.1 \times 10^{-09}$** | | |
| WBC | 0.95 | 0.21 | |
| Neut | 0.92 | 0.41 | $3.8 \times 10^{-28}$** |
| Lymph | 0.005* | 0.01* | $3.0 \times 10^{-08}$** |
| Mono | 0.08 | 0.09 | $1.3 \times 10^{-04}$** |
| Eosin | 0.76 | 0.49 | 0.28 |
| Plt | 0.03* | 0.39 | 0.01* |
| Baso | 0.02* | 0.03* | 0.41 |
| RBC | 0.02* | $2.69 \times 10^{-03}$* | $7.8 \times 10^{-07}$** |
| Hgb | 0.45 | 0.03* | $3.1 \times 10^{-05}$** |
| Hct | 0.46 | 0.03* | $1.1 \times 10^{-04}$** |
| TotP | $3.9 \times 10^{-05}$** | 0.02* | 0.10 |
| Creat | 0.31 | 0.17 | 0.38 |
| Urea | 0.02* | 0.45 | 0.26 |
| GGT | 0.09 | 0.82 | 0.27 |
| AST | 0.33 | 0.02* | 0.03* |
| CK | 0.009* | 0.03* | 0.13 |
| LDH | 0.04* | 0.04* | 0.09 |
| GLDH | 0.06 | 0.42 | $7.5 \times 10^{-05}$** |
| ALP | 0.10 | 0.09 | $1.1 \times 10^{-12}$** |
| ALB | 0.50 | 0.18 | 0.41 |
| Glob | $2.2 \times 10^{-07}$** | $2.5 \times 10^{-03}$* | 0.18 |

TABLE 2

Concordance of occurrence of extreme values among diverse blood assays. Two proteins associated with the inflammatory response, Serum Amyloid A and Fibrinogen, and total White Cell Count are compared against each other and against 20 other cell count/protein assays. In each case a simple 2X2 test of homogeneity is conducted to test for an association between the top 15% of values observed. Values presented are interpreted with one degree of freedom. Values significant at P < 0.05 are indicated with one asterisk, those significant experiment-wide are indicated with two asterisks. Abbreviations of assays are found in methods.

|  | Fibrinogen | SAA | WBC |
|---|---|---|---|
| SAA | 45.7** | | |
| WBC | 1.1 | 4.2* | |
| Neut | 6.1* | 7.2* | 27.9** |
| Lymph | 2.9 | 1.8 | 13.0** |
| Mono | 2.1 | 1.4 | 6.2* |
| Eosin | 0.0 | 0.0 | 0.0 |
| Plat | 0.0 | 0.0 | 0.5 |
| Baso | 4.4* | 1.3 | 0.0 |
| RBC | 2.9 | 0.7 | 0.9 |
| Hgb | 3.4 | 1.0 | 0.5 |
| Hct | 1.7 | 1.0 | 0.0 |
| TotP | 3.9* | 5.6* | 8.7* |
| Creat | 0.4 | 0.9 | 0.8 |
| Urea | 5.0* | 0.0 | 0.0 |
| GGT | 0.4 | 0.1 | 0.1 |
| AST | 0.5 | 2.5 | 0.2 |
| CK | 0.0 | 0.1 | 0.0 |
| LDH | 2.3 | 2.1 | 0.5 |
| GLDH | 0.2 | 6.5* | 1.5 |
| ALP | 2.3 | 1.9 | 11.4** |
| ALB | 1.1 | 0.9 | 1.2 |
| Glob | 3.9* | 9.4* | 8.7* |

4. Discussion

We explored the relationship between a number of standard blood parameters in a sample of thoroughbred racehorses in training. Our data reveal that while the most commonly used indicator of health, total white cell count, correlates broadly with both individual cell sub-type counts and several elements of blood chemistry, there is relatively poor agreement between horses with the highest white cell counts and the highest values in other measures such as the inflammatory markers SAA and fibrinogen. In contrast, two components of the inflammatory response, SAA and fibrinogen, correlate relatively weakly with WBC and blood chemistry but show excellent agreement with one another when it comes to high values. Furthermore, by application of two separate statistical models of analysis, similar trends can be observed demonstrating that this study group was indeed a random sample population of thoroughbred racehorses and may not have been overly influenced by particularly 'extreme' individuals.

Blood chemistry and white cell counts are both used routinely as indicators of health however readings in healthy horses are far from constant and vary with levels of hydration and other factors. For this reason, measurements are generally conducted in as standardised a way as possible, at the same time of day and the same time relative to feeding and exercise. Nonetheless, variation still seems likely due to factors such as individual-specific patterns in urination, environmental temperature and anxiety, and this appears to be reflected in the way most of the white cell counts and blood chemistry measures exhibit some degree of cross-correlation.

To understand which part of the range of observed values of a given trait are associated with ill-health as opposed to natural daily and hourly variation in homeostasis would involve tracking the fate of horses that were trained at a constant level until clinical symptoms developed. However, such an experiment is largely precluded by the need to act pre-emptively so as to maximise horse welfare. Instead, therefore, we focused entirely on correlations between the various blood analytes in general (Table 1), comparing these with the level of concordance seen between high value readings for the same measurements (Table 2). In this way we can see the extent to which different measurements co-vary across their entire range, a pattern that would suggest correlation with some other factor such as diurnal variation in hydration, as opposed to a specific tendency for high values at one measure to be associated with high values at another, a pattern that tends to identify an unusual subset of horses. We presume that such subsets represent horses with, in this case, an on-going inflammatory response.

Our argument is that, from experience, a small but unknown subset of our number of horses in training are likely to have incipient health issues. If these horses can be detected, they should be contributing unusually high trait values. Moreover, if two or more traits are useful as indicators, these should show good agreement in their highest values. When we interrogate our data in this way we find a reversal, with WBC showing weaker correlations among the highest 15% of values compared with fibrinogen and SAA. By implication, fibrinogen and SAA show agreement in identifying a subset of horses with unusual readings, most parsimoniously explained by these horses currently suffering some level of injury or illness involving the inflammatory response. The apparent lack of specificity of WBC counts likely reflects the large diversity of factors that can affect them, many of which are not directly related to health.

Our results raise questions both about what WBC are detecting and what they are expected to detect as a pre-performance assay. Cell counts undoubtedly fluctuate in a biologically meaningful way, but there are two complications. First, the correlation between WBC and many of the blood chemistry measures suggests that the majority of the variation in our sample is due to normal variation in blood concentration rather than specific responses to a particular challenge. Second, the range of stimuli capable of impacting WBC is wide, diverse and some may even depress cell counts. Consequently, a single WBC is unlikely to tell us much about incipient problems. Better would be a monitoring programme based on repeated measures so that sudden changes could be better identified, but even here the meaning of such changes may be difficult.

In comparison with WBC, fibrinogen and SAA appear to have considerably better discriminatory power, both largely agreeing with each other about a subset of horses with clearly elevated readings. The implication is that these horses may have an otherwise undetected health problem. From a diagnostic perspective, this brings both positive and negative aspects. The negative aspect is that SAA and fibrinogen will not identify horses suffering from problems that are not currently causing an inflammatory response. The positive side is that these two blood proteins, in contrast to WBC, appear to identify a relatively specific state, that of horses exhibiting an inflammatory response.

5. Conclusions

We conclude that fibrinogen and SAA have excellent potential as biomarkers and are likely to be more informative about conditions relevant to horses in training compared with the widely used WBC.

REFERENCES FOR EXAMPLE 1

[1] Parry-Billings M, Budget R, Koutedakis Y, Blomstrand E, Brooks S, Williams C, et al. Plasma amino acid concentrations in the overtraining syndrome: possible effects on the immune system. Med Sci Sports Excer 1992; 24:1353-1358.
[2] Rickets S W. Hematologic and Biochemical abnormalities in athletic horses. In: Hinchcliff K W, Keneps A J, Geor R J, editors. Equine Sports Medicine and Surgery, Philadelphia: W. B Saunders; 2004, p. 952.
[3] Welles E G. Interpretation of Equine Leukocyte Responses. In: Weiss D J, Wardrop K J. Schalm's Veterinary Hematology, 6.ed, Iowa: Wiley-Blackwell; 2010, p. 317
[4] Couetil L L, Hoffman A M, Hodgson J, Buechner-Maxwell V, Viel L, Wood J L N, et al. Inflammatory Airway Disease of Horses. J Vet Intern 2007; 21:356-361.
[5] Grondin T M, Dewitt S F, Normal hematology of the horse and donkey. In: Weiss D K, Wardrop K J. Schalm's veterinary hematology, 6.ed, Iowa: Wiley-Blackwell, 2010; p. 821-828.
[6] Hultén C, Sandgren B, Skioldebrand E, Klingeborn B, Marhaug G, Forsberg M. The acute phase protein serum amyloid A (SAA) as an inflammatory marker in equine influenza virus infection. Acta Vet Scand 1999; 40:323-333.
[7] Hulten C, Gronlund U, Hirvonen J, Tulamo R M, Suominen M M, Marhaug G, et al. Dynamics in serum of the inflammatory markers serum amyloid A (SAA), haptoglobin, fibrinogen and alpha2-globulins during induced non-infectious arthritis in the horse. Equine Vet J 2002; 34: 699-704.
[8] Pepys M B, Baltz M L, Tennent G A. Serum amyloid A (SAA) in horses: objective measurement of the acute phase response. Equine Vet J 1989; 21:106-109.
[9] Jacobsen S, Nielsen J V, Kjelgaard Hansen M, Toelboell T, Fjeldborg J, Halling Thomsen M, et al. Acute phase response to surgery of varying intensity in horses: a preliminary study. Vet Surg 2009; 38:762-769.
[10] Pusterla N J, Watson J L, Wilson W D. Diagnostic approach to infectious respiratory disorders. Clin Tech Eq Pract 2006; 5:174-186.
[11] Allen B V, Kold S E. Fibrinogen response to surgical tissue trauma in the horse, Equine Vet J 1988; 20: 441-443.
[12] Burrows G E. Dose-response of ponies to parenteral *Escherichia coli* endotoxin. Can J Comp Med 1981; 45:207-210.
[13] Crisman M V, Scarratt W K, Zimmerman K L. Blood Proteins and Inflammation in the horse. Vet Clin Equine Practice 2008; 24:285-297.
[14] Heidman P, Madigan J E, Watson J L. *Rhodococcus equi* Pneumonia: Clinical Findings, Diagnosis, Treatment and Prevention. Clin Tech Eq Pract 2006; 5:203-210.
[15] Takizawa Y, Hobo S J. Usefulness of plasma fibrinogen concentration measurement in diagnosis of respiratory disorders in thoroughbred horses. Equine Sci 2006; 2:22-37.
[16] Satue K, Calvo A, Gardon J. Factors Influencing Serum Amyloid Type A (Saa) Concentrations in Horses. Open Journal of Veterinary Medicine 2013 3:58-66.
[17] Tape C, Kisilevsky R. Apolipoprotein A-I and apolipoprotein SAA half-lives during acute inflammation and amyloidogenesis. Biochem Biophys Acta 1990; 1043: 295-300.
[18] Vandenplas M L, Moore J N, Barton M H, Roussel A J, Cohen N D. Concentrations of serum amyloid A and lipopolysaccharide-binding protein in horses with colic. Am J Vet Res 2005; 66:1509-1516.
[19] Jacobsen S, Thomsen H, Nanni S. Concentrations of serum amyloid A in serum and synovial fluid from healthy horses and horses with joint disease, Am J Vet Research 2006; 67:1738-1742.
[20] Jacobsen S, Kjelgaard-Hansen M, Petersen H, Jensen A L. Evaluation of a commercially available human serum amyloid A (SAA) turbidometric immunoassay for determination of equine SAA concentrations. Vet J 2006; 172(2):315-319.
[21] Mast Group (No publication date) *Eiken Serum Amyloid A (SAA)*[Online] Merseyside, Mast Group LtdAvailable: http://www.mastgrp.com/Eiken/InfoSheet/SAA%20reagents.pdf [Accessed 18 Sep. 2013].

Example 2

Introduction and Methods

Clinical symptoms in horses may only appear when over-stressing has already occurred, and there is an unmet need to provide methods to determine imminent problems at sub-clinical stages.

The SAA levels of a group of thoroughbred horses bred for flat racing were recorded over a three month period (April to June and n=61) as part of a routine biochemical panel for pre-performance testing. Of the 61 horses tested 25 ran during the testing period. The horses were managed in the same way under the same training schedule. SAA levels were determined using a two-step lateral flow immunoassay and a lateral flow reader (LFR101) by the suitably qualified in-house laboratory technician. The names of the horses and the events in which they participated were recorded but not reported. The data was observed and three relevant ranges for horses in training became apparent. Horses with a SAA concentration below 7.5 ug/ml are clinically well, free from subclinical infection and with the exception of those conditions which do not invoke a SAA response, are fit and healthy horses. Horses that ran with SAA levels of 15 μg/ml and over performed below expectation, particularly those with SAA levels in excess of 30 μg/ml. Horses with a SAA of greater than 200 μg/ml are clinically unwell with visible symptoms. The SAA levels of 16 horses in the study group was tested more than once to monitor recovery and/or to further impaired performance.

Results and Discussion

In the group of horses that tested with a SAA concentration greater than 200 μg/ml (n=5) (Table 1), 3 of the group had infections confirmed by either clinical examination or further by diagnostic investigation. One record for a recent inoculation of the equine herpes virus is reported. One horse of the group ran during the study and did not perform to expectation. The horse was assumed to have virus and subsequent testing at a later date identified mucus and neutrophils in a tracheal wash (Table 2).

TABLE 1

Levels above 200 μg/ml - Elevated SAA post vaccination and clinical confirmation of infection in 3 of the 4 horses who were not vaccinated. Subsequent testing of the remaining horse confirmed the presence of bacterial or viral infection.

| SAA μg/ml | Infection | Comments on Performance | Trainers Comments |
|---|---|---|---|
| 641.7 | n/a | n/a | Equine herpes virus vaccination |
| 539.6 | Confirmed by presence of bacteria in lung wash | n/a | |
| 331.7 | Confirmed by clinical examination of wound | n/a | Infected leg wound |
| 243.4 | Confirmed by tracheal wash | n/a | Cracked heels |
| 234.72 | Not confirmed | Performed lower than expectations | Potential virus, visibly out of form |

TABLE 2

A horse with an elevated SAA >200 μg/ml was monitored post-race following a poor performance. Neutrophils were subsequently identified in a tracheal wash. SAA had returned to normal levels after antibiotic treatment.

| Date | SAA μg/ml | Trainer Comments |
|---|---|---|
| 18 Apr. 2013 | 234.72 | Performed below expectation - suspected virus |
| 25 Apr. 2013 | 63.46 | |
| 1 May 2013 | 128.47 | Mucus and neutrophils in tracheal wash |
| 7 May 2013 | 1.38 | Post antibiotic treatment |

SAA concentrations between 30 μg/ml and 200 μg/ml were recorded for 15 (Table 3) horses in the study group. 6 of the 16 ran with an elevated SAA and all performed lower than the expected standard according to comments recorded at the time of testing. Post-race testing revealed mucus and blood in the tracheal wash of one of the 6 runners while another with a known elevated SAA concentration had been diagnosed with a bacterial lung infection 10 days prior to the race. In this instance SAA was monitored and levels had decreased but remained elevated on the day of racing and performance was recorded as below expectations.

SAA levels were monitored over the course of 9 days for one horse in the group of 6 under-performing horses (Table 4). 0μg/ml was recorded on the day of racing however SAA had increased to 32.46 μg/ml and 34.01 μg/ml on day 2 and 3 respectively with no clinical symptoms were detected. SAA levels had returned to 0μg/ml by day 9 of testing. A knee injury was sustained by one of the runners during the race and in addition a suspected viral infection was recorded for the same horse. SAA levels, post-performance were measured at 175 μg/ml which supports the likelihood of a pre-existing of viral infection. SAA was the sole indicator of a subclinical challenge for 3 of the 6 underperformers.

Of the horses who did not run within this range no clinical symptoms were recorded at the time of testing for two of the group however the remaining 8 horses, 4 were being monitored, 1 had an abnormal tracheal wash without confirmation of infection and 2 had no clinical symptoms. Comments were not recorded for one horse with an elevated SAA.

TABLE 3

SAA concentrations above 30 μg/ml but below 200 μg/ml (where symptoms are visible) indicate the presence of an underlying issue.

| SAA μg/ml | Infection | Performance Comments | Trainer Comments |
|---|---|---|---|
| 196.92 | | | No clinical symptoms |
| 189.17 | | | No clinical symptoms |
| 175.39 | | Performed below expectation | Knee injury sustained during race. Suspected virus. |
| *128.47 | Confirmed by the presence of mucus and neutrophils in tracheal wash | | |
| *119.42 | | Performed below expectation | No clinical symptoms |
| *108.23 | Confirmed bacterial infection in lungs | | Post antibiotic treatment |
| *97.90 | Confirmed by bacteria in tracheal wash | | |
| 93.59 | Confirmed by bacteria in tracheal wash | | |
| 79.82 | | Performed below expectation | No clinical symptoms |
| 65.18 | Confirmed by white blood cells in tracheal wash | | |
| *65.18 | Confirmed by bacterial infection in lungs | Performed below expectation | |
| *63.46 | Confirmed by the presence of mucus and neutrophils in tracheal wash | | SAA is decreasing |
| 55.71 | | | |
| *52.26 | Confirmed by bacteria in tracheal wash | | Post antibiotic treatment |
| 52.26 | Confirmed by mucus in tracheal wash | Performed below expectation | Blood in tracheal wash |

TABLE 3-continued

SAA concentrations above 30 μg/ml but below 200 μg/ml (where symptoms are visible) indicate the presence of an underlying issue.

| SAA μg/ml | Infection | Performance Comments | Trainer Comments |
|---|---|---|---|
| 46.41 | | | |
| 46.24 | | Performed below expectation | No clinical symptoms A very consistent flat horse |
| *34.01 | | | |
| *32.46 | | | |
| 31.60 | Not confirmed | | Abnormal tracheal wash |

Horses which appear twice within the table are marked with as asterisk*.

TABLE 4

A horse was monitored was 9 days following a poor performance, SAA levels had returned to normal by day 9 of testing. There were no clinical symptoms.

| Date | SAA μg/ml | Trainers Comments |
|---|---|---|
| 21 May 2013 | 0 | Performed below expectation |
| 22 May 2013 | 32.46 | — |
| 23 May 2013 | 34.01 | — |
| 30 May 2013 | 0 | — |

Seven horses were recorded with an SAA concentration between 15 μg/ml and 30 μg/ml (Table 5). 3 of the 7 raced during the duration of the study and 2 performed below expectations. There were no visible symptoms of illness observed in the runners and further investigation revealed only an elevated AST concentration for one of the pair. Of the remaining horses that did not run, all were under investigation for previous poor performance and SAA levels were elevating or decreasing when recorded.

TABLE 5

SAA concentrations between 15 ug/ml and 30 ug/ml.

| SAA μg/ml | Infection | Performance Comments | Trainer Comments |
|---|---|---|---|
| *29.88 | | | Fibrinogen elevated AST elevated |
| 28.16 | Confirmed by presence of bacteria in tracheal wash | | |
| 28.16 | | Performed below expectation | No clinical symptoms |
| *25.92 | | Performed as expected | Blood in tracheal wash |
| 24.71 | Not confirmed | | Abnormal tracheal wash Antibiotic treatment |
| *19.55 | | | |
| 18.68 | | Performed below expectation | AST elevated |
| *17.82 | | | |
| 15.24 | | | |

3 SAA concentrations were recorded for horses between 7.5 μg/ml and 15 μg/ml. One horse of the group ran performing as expected. The two remaining horses did not run and were being monitored following an injury and an abnormal tracheal wash (Table 6). Horses within this range may be in the initial stages of an SAA elevation or they may be recovering from an infection where concentrations have dropped significantly. For this reason it is difficult to realise the potential of SAA when used within this range. A more reliable range begins at 15 μg/ml above which poor performance is likely when considering this set of data.

TABLE 6

SAA concentrations between 7.5 μg/ml and 15 μg/ml

| Date | SAA μg/ml | Infection | Performance Comments | Trainers Comments |
|---|---|---|---|---|
| 09.05 | 14.38 | Not confirmed | | Blood in tracheal wash |
| 18.05 | 11.80 | | | Knee injured |
| 19.04 | 7.75 | | Performed as expected | |

69 SAA levels were recorded below 7.5 ug/ml for 55 horses. SAA levels were being monitored for 14 of the group. 13 ran during the study period and with the exception of one horse that later measured with an elevated SAA, all performed as expected. Outside of those horses being monitored only one confirmed infection was reported.

TABLE 7

SAA concentrations below 7.5 μg/ml

| SAA μg/ml | Infection | Performance Comments | Trainer Comments |
|---|---|---|---|
| 7.49 | | Performed as expected | |
| 7.49 | | | |
| 4.05 | | Performed as expected | |
| 3.19 | | | Chronic lung problems |
| 3.19 | | Performed as expected | |
| 1.81 | | Performed as expected | |
| 1.38 | | | Post antibiotics treatment |
| 0.60 | Confirmed by presence of mucus and neutrophils in tracheal wash | | |
| 0.43 | | | |
| 0 | | | Abnormal profile |
| 0 | | Performed as expected | |
| 0 | | | Out of form |
| 0 | | Performed as expected | |
| 0 | | | |
| 0 | | Performed below expectation | |
| | | | Blood in tracheal wash |
| 0 | | | |
| 0 | | | Fibrinogen elevated |
| 0 | | | Fibrinogen elevated |
| 0 | | | Injured knee |
| 0 | | Performed as expected | |
| 0 | | | |
| 0 | | | |
| 0 | | | |
| 0 | | | |
| 0 | | | |
| 0 | | | Lung allergy |
| 0 | | | |
| 0 | | | |

TABLE 7-continued

SAA concentrations below 7.5 μg/ml

| SAA μg/ml | Infection | Performance Comments | Trainer Comments |
|---|---|---|---|
| 0 | | | Post antibiotic treatment |
| 0 | | | Blood in tracheal wash |
| 0 | | | Lung allergy |
| 0 | | | Lung allergy |
| 0 | | Performed as expected | |
| 0 | | Performed as expected | |
| 0 | | | Abnormal tracheal wash |
| 0 | | | Lung allergy |
| 0 | | | Blood in tracheal wash |
| 0 | | | |
| 0 | | | |
| 0 | | Performed as expected | |
| 0 | Infection confirmed by mucus in tracheal wash | expected | Blood and mucus in tracheal wash |
| 0 | | | |
| 0 | | Performed as expected | |
| | | Performed as expected | |
| 0 | | | |
| 0 | | | |
| 0 | | | Post antibiotic treatment |
| 0 | Confirmed by neutrophils in tracheal wash | | |
| 0 | | | Elevated AST |

The SAA levels of a number of horses were recorded on more than one occasion during the study in order to monitor recovery. Those horses for which four or more data points were recorded are reported here (Table 8). The data indicates that SAA levels resolve before the traditional WBC profile returns to normal. In addition SAA can be used to determine the efficacy of a treatment by monitoring the response of the protein post administration.

TABLE 8

14 horses were monitored to access SAA as a tool for monitoring recovery during the study.

| Date | Name | SAA μg/ml | Trainer Comments |
|---|---|---|---|
| 24.04 | | 28.16 | Mucus and bacteria in tracheal wash |
| 26.04 | | 0 | WBC blood profile is still abnormal |
| 30.04 | | 0 | |
| 02.05 | | 0 | |
| 21.05 | | 0 | Performed below expectation |
| 22.05 | | 32.46 | |
| 23.05 | | 34.01 | |
| 30.05 | | 0 | SAA normal |
| 26.04 | | 93.59 | Abnormal tracheal wash |
| 02.05 | | 24.71 | On antibiotics |
| 14.05 | | 0 | Post antibiotic treatment |
| 24.04 | | 343.29 | Bacteria in tracheal wash, cracked heels |
| 30.04 | | 0 | |
| 09.05 | | 0 | |
| 11.06 | | 501.72 | Bacterial infection in lungs |
| 11.06 | | 108.23 | Post antibiotic treatment |
| 21.06 | | 65.18 | Performed below expectation. |
| 09.05 | | 14.38 | Increased blood in tracheal wash |
| 14.05 | | 0 | SAA normal |
| 22.05 | | 52.26 | Performed below expectation |
| 30.05 | | 0 | SAA normal |
| 04.06 | | 394.95 | Infected leg wound |
| 11.06 | | 0 | SAA normal |

The vast majority of horses are physiologically healthy and this is reflected in the data. As SAA concentration exceeds 7.5 μg/ml the performance of the horses in the study decreased with few exceptions making SAA a very relevant biomarker for horses in training. The data for the performance of horses between 7.5 μg/ml and 15 μg/ml is rather inconclusive and performance is hard to predict. Above 15 μg/ml a decline in performance persists however other indicators of a reduced physiological health status do not always accompany the measurement. A particular decline in performance is noted above 30 μg/ml and elevated SAA is more often accompanied by other indications of infection most notably a tracheal wash elevated neutrophil count. As SAA concentrations further increase clinically visible symptoms of illness become apparent and above 200 μg/ml, all records were accompanied by visible illness and/or additional abnormal test results.

Three relevant ranges have emerged, <7.5 mg/ml, 15 ug/ml and >200 ug/ml. Since a decline in performance is most notable above 15 μg/ml, a useful tool for determining SAA does not indicate the presence of the protein until levels have reached or exceeded this value to facilitate ease of interpretation. An increase in the test signal should correspond to an increase in SAA levels and be present in the form of a single band. Such a testing format makes the user immediately aware that SAA in present in a concentration which may require attention when a signal appears. The absence of a signal indicates to the user that the horse is in a healthy state. The SAA concentration can then be semi-quantitatively determined with the use of a reference card demonstrating levels of intensity to which the test signal can be compared or a quantitative reading can be determined with the use of an electronic reader.

Example 3

A case study was conducted to assess the efficacy of SAA as a tool to monitor and manage the recovery of horses. A previous study had indicated that SAA concentrations above 200 ug/ml are accompanied by clinical symptoms and therefore SAA may be used monitor recovery and response to treatment; however the range above 200 μg/ml was not fully investigated due to the limitation of elevated samples.

For this reason an additional case study was performed to specifically evaluate SAA as a tool for monitoring recovery. Clinical comments were provided by a veterinarian at the time of testing. The name of the horse was recorded but is not reported.

Figure 11:
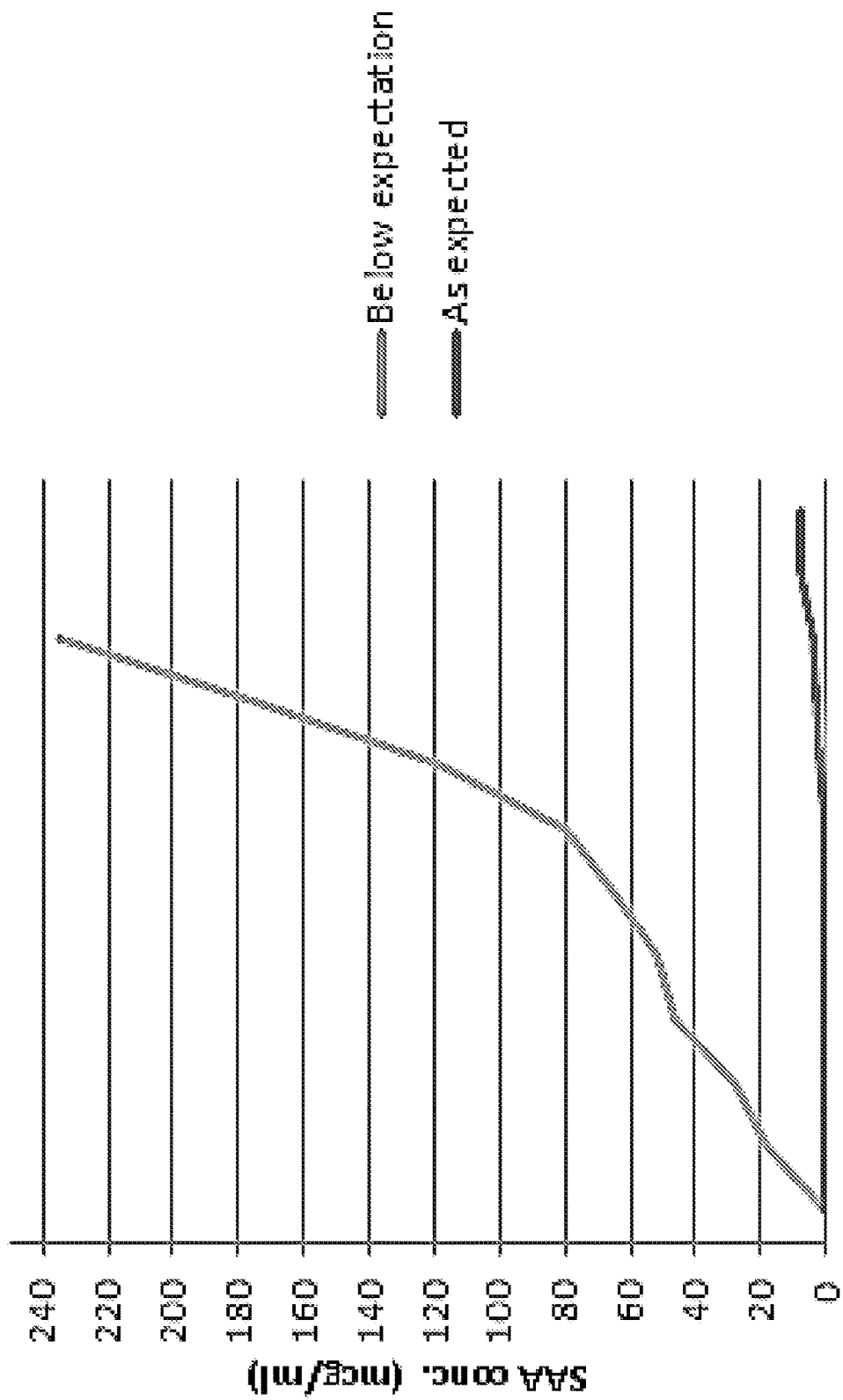

The SAA levels of a horse that presented with travel sickness (pleuropneumonia) were measured daily for 13 days following a 6689 kilometer transportation (Table 1, FIG. 11). Clinical examination, SAA testing and scanning were carried out by an ambulatory veterinarian. The horse was treated with Ceftiofur (antibiotic), Marbofloxacin (antibiotic), Flunixin (anti-inflammatory) Metronidazole (antibiotic) and Gastrogard (treatment/prevention of equine ulcers). The rapid increase on day 7 corresponds with a neck injury from treatment administration.

TABLE 1

SAA measurements and clinical assessment of a horse with travel sickness.

| Date | SAA µg/ml | Veterinarian Comments |
|---|---|---|
| 21.06 | 379.5 | Temp 102, thin, dull. Fluid on right hand side chest & consolidated lung. |
| 22.06 | 3493 | Improved condition, temp 101. Lung consolidation. |
| 23.06 | 3285 | Temp normal |
| 24.06 | 3384 | Temp normal, consolidation resolving |
| 25.06 | 3112 | Temp normal, consolidation resolving |
| 26.06 | 2640 | Temp normal, consolidation resolving, reduced flunixin |
| 27.06 | 3960 | Temp normal, consolidation resolving, reduced flunixin |
| 28.06 | 2755 | Gas pocket in neck, changed ceftiofur to cefquinome |
| 29.06 | 838 | Scan much improved |
| 30.06 | 475 | Temp consistent 99.8 |
| 01.07 | 199 | Temp consistent 99.8 |
| 02.07 | 101 | Temp consistent 99.4, stop flunixin |
| 03.07 | 39 | Scan improved, small comet tails, stop marbocyl |

Discussion

The data from the case study indicate that SAA can be used to efficiently monitor the recovery of the horse. The study particularly demonstrates the use of SAA to determine the biochemical efficiency of the course of treatment and SAA elevations and decreases were in agreement with clinical examination.

Assay Development

A two-step lateral flow immunoassay was developed for horses after the observation of data which supported the use of SAA as a pre-performance test and as a health management tool for monitoring recovery and/or response to treatment. During the course of the study it became apparent that fit and healthy horses were reported with SAA concentrations less than 7.5 µg/ml while impaired performance largely corresponded with levels above 15 µg/ml. Levels in excess of 200 ug/ml were accompanied by clinical symptoms, the resolution or exacerbation of which was reflected by the level of SAA.

The lateral flow assay was developed in the sandwich format and consists of a nitrocellulose membrane upon which an anti-SAA antibody and a control antibody have been immobilised. The membrane is assembled together on a backing material with a glass fibre conjugate pad, a cellulose sample pad and a cellulose absorbent pad. The conjugate pad contains the anti-SAA-colloidal gold complex which is required for the detection of SAA. The sample pad contains additional reagents which increase the stability and performance of the assay. The materials are assembled together into a plastic housing which consists of a sample well and a viewing window. Prior to sample application, the sample is diluted 1/800 in a running buffer (5 ul in 4 ml). The sample is applied to the sample pad via the sample well. The reagents within the sample and conjugate pad become mobile and move through the membrane to test line where a signal is raised if SAA is present at or above 15 µg/ml in the sample. The intensity of the test line visibly increases as the concentration of SAA increases up to a visible maximum 1000 µg/ml where the line becomes saturated to the eye. The range can be further extended up to 3000 µg/ml using an electronic reader. A semi-quantitative reading can be determined by use of a reference card upon which representations of the intensity of 15 µg/ml, 50 µg/ml, 200 µg/ml and 1000 µg/ml are available for comparison.

Example 4—SAA to Distinguish Infectious and Non-Infectious Disease or Syndromes

Introduction and Methods

A number of case studies were compiled from data generated through two Equine Veterinary Hospitals. SAA levels were determined by the in-house laboratory technicians and clinical comments were provided by Board Certified Internal Medicine Veterinarians The levels of SAA were determined in horses diagnosed with infectious and non-infectious diseases and was observed to respond most rapidly and dramatically to bacterial and viral infections, while allergies, EIPH and other non-infectious inflammatory conditions showed little or no response. SAA levels were also observed to elevate during colic and post-colic surgery indicating SAA as a potent marker of infection and not a marker general inflammation.

Results and Discussion

Infectious

| Diagnosis | SAA Peak Range Detected | Common Symptoms Observed | No. of Case Studies |
|---|---|---|---|
| Bacterial Lung Infection | 45-1028 | Bacteria in trach wash | 6 |
| Unidentified Viral Infection | 16-1109 | Fever, filled legs | 10 |
| Rhodococcus equi | 709-4936 | Mucus, Cough | 7 |
| Rotavirus | 1416-2763 | Diarrhea, loss of appetite | 2 |
| Post-Colic Surgery Infection | 100-1000+ | Discomfort, Swelling | 3 |
| Post-Gelding Infection | 709-4453 | Swelling | 7 |
| Abscess | 14-4868 | Swelling, Heat. | 5 |
| Cellulitis | 4931 | Heat, Pain. | 2 |
| Encephalitis | 2838 | Fever | 1 |
| Osteomyelitis | 329-905 | Swelling, Lameness | 3 |
| Pneumonia | 141-5000+ | Cough, Fever | 5 |
| Peritonitis | 5000+ | Abdominal pain | 1 |

Non-Infectious

| Diagnosis | SAA Peak Range Detected | Common Symptoms | No. of Case Studies |
|---|---|---|---|
| Exercise Induced Pulmonary Hemorrhage | 0-45 | Blood in trach wash | 3 |
| Allergy | 0 | Snorting, coughing. Blood in trach wash. | 1 |
| Colic | 100-1000+ | Abdominal pain | 3 |
| Inflammatory Bowel Disease | 10 | Abdominal pain | 1 |
| Airway Inflammation | 2.2 | Cough, Mucus | 1 |
| Edema | 0 | Swelling | 1 |
| Exertional Rhabdomyolysis | 0 | Lameness, Cramping. | 52 |
| Heaves | 0 | Cough, Mucus | 1 |

The case studies compiled in Table 1 demonstrates the potential for serum amyloid a to be used as a method for differentiating between infectious and non-infectious conditions.

Levels of SAA detected for EIPH are considered to be from early stages of a secondary bacterial infection.

The benefits of such a method extend to diagnostic procedures where an infection can be confirmed before further investigation as well as allowing for the prompt initiation of a suitable treatment regime for sick horses based on whether they are being treated for an infectious disease such as those associated with micro-organisms or non infectious illness such as those associated with the environment or lifestyle or genetic factors. Furthermore SAA has been seen to elevate to a larger extend when the horse is challenged with a bacterial infection compared to a viral infection which creates scope for SAA to be used not only as a marker of differentiation between infectious and non infectious disease but also as a method of differentiating between the organism responsible which has implications for the type of therapy administered e.g. viral infections will not respond to antibiotic therapy.

Example 5—SAA as a Screening Tool in Newborn Foals

Introduction

Screening for SAA in newborn foals, under 10 hours old, has been shown to be an excellent risk-reduction method and can clearly identify foals susceptible to liver failure, diarrhea and other infectious conditions.

SAA (Serum Amyloid A) was adapted as part of a health screening test for newborn foals. A white blood cell count (WBC) was also conducted as part of the screening process. As WBC naturally fluctuate and can go down and up when challenged, SAA as a point of care screening tool is a more reliable indicator of a newborns changing health status.

Methods

Testing was conducted by the suitably qualified in-house laboratory technician and clinical comments were provided by a licensed Veterinarian within 24 hours of birth. Data was collected from 22 newborns in total and analysed to determine the potential for SAA as a screening tool for compromised newborns.

Results and Discussion 22 newborn foals were screened of which 15 tested SAA negative and 7 tested SAA positive (Table 1). WBC data for the newborns ranged from 7.1-17.9×$10^3$/μl.

TABLE 1

Blood results and clinical notes from 22 newborns

| Case No. | SAA (μg/ml) | Clinical Notes |
| --- | --- | --- |
| 1 | 16.5 | Healthy newborn, developed R. Equi one month later. |
| 2 | 0 | Healthy newborn |
| 3 | 7.5 | Healthy newborn, went on to develop multiple joint and bone infections. |
| 4 | 0 | Healthy newborn |
| 5 | 0 | Healthy newborn |
| 6 | 0 | Healthy newborn |
| 7 | 0 | Healthy newborn |
| 9 | 0 | Healthy newborn |
| 10 | 0 | Healthy newborn |
| 11 | 81.5 | Healthy newborn |
| 12 | 0 | Healthy newborn |
| 13 | 0 | Healthy newborn |
| 14 | 1464.5 | Rotavirus diagnosed and sent to hospital |
| 15 | 0 | Healthy newborn |
| 16 | 0 | Healthy newborn |
| 17 | 265 | Elevated BUN and creatine |
| 18 | 0 | Healthy newborn |
| 19 | 0 | Healthy newborn |
| 20 | 0 | Healthy newborn |
| 21 | 35.5 | Healthy newborn, went on to develop diarrhea |
| 22 | 167.5 | Weak |

Of the 7 SAA positive newborns, 1 was diagnosed within 24 hours of birth with a viral infection and transferred to hospital. Another displayed elevated BUN and creatine levels in addition to elevated SAA.

A third newborn was described as weak. Two newborns went on to develop health problems a later date, one within the first month of birth and one within two weeks.

The newborn in Case 1 (Table 1) was diagnosed with *Rhodococcus equi* one month after the SAA determination. The newborn was determined to be healthy on examination and had a mildly elevated SAA level. *Rhodococcus equi* is a bacterial infection and one of the most common causes of pneumonia in foals. Infected foals may remain lively and asymptomatic until late in the course of the disease. Infection has been recognized as endemic on some farms and costs related to illness and mortality may be high at these locations *Rhodococcus equi* is nearly ubiquitous in soil and while the infection is unlikely to have been contracted immediately after birth, SAA can be used in as a screening test for early identification of those newborns who may be at risk of developing the infection.

The newborn in case 3 was assessed as a healthy newborn after birth and had a low level of SAA. Within two weeks of initial SAA testing the foal had developed multiple joint and bone infections during which SAA levels rose in excess of 3000 μg/ml.

In addition to be being used as a screening tool to identify potentially compromised newborns SAA was also used in this instance to determine the point at which antibiotic treatment should be withdrawn by monitoring the decrease in SAA levels.

SAA has been shown to detect the presence of viral infections including rotavirus. Rotavirus is a highly contagious virus that affects foals and if left untreated can become life threatening due to severe dehydration and malnutrition. Case 14 provides a second example of the potential for SAA to be used as an initial screening tool and then as a tool to monitor the response of a foal to treatment. The newborn was diagnosed with a rotavirus infection within 24 hours of birth and sent to hospital. SAA levels were then recorded until they fell within the normal range.

Unlike adult horses, newborns may display levels of SAA elevation in the very early hours of life due to liver activity unrelated to infection, its assumed that this may be related to the transfer of functionality from the placenta to the newborn liver as can been observed in case 17 below, where markers of poor liver function are elevated. Nevertheless it can be seen that SAA is a useful marker of foals that may develop health issues within the first 48 hours after birth, which is when foals are at highest risk of fatality.

Example 6—Test Fluid Collection System

Some key features of the system are shown in FIG. 14, and are explained in more detail below:

Multi-Purpose Sample Collection Tip

The sample collection tip has been designed such that different methods can be used to collect a sample. Firstly, the dimensions of the tip allow for the attachment of a luer end needle so that blood can be collected straight from the vein. Alternatively, a lancet can be used to produce a drop of blood from the patient and the BCS used to pick up a metered volume from the drop using capillary action. Similarly, the BCS can pick up blood from the end of a syringe or from a container.

Collection Port

The BCS collection port can be considered to be the most important part of the device. The collection port comprises of two closely aligned surfaces. The space between the two surfaces determines the volume of sample to be collected. Due to the design of the port and nature of the hydrophilic-treated surfaces, sample collection occurs by capillary action and is quick and accurate. This removes the requirement for aspirating sample with a pipette, which removes the risk of error by users who would not be familiar with using pipettes.

Dispensing Channel and Nozzle

The BCS is designed to fit into the neck of a bottle, with the collection port and the dispensing channel located inside the bottle. The BCS/bottle can then be inverted for mixing. Reduction in volume of the bottle then forces the diluted solution into the dispensing channel and through the dispensing nozzle.

Example 7—Monitoring of Exertional Rhabdomyolysis

Exertional Rhabdomyolysis, also known as Tying up, is a condition induced by exercise, characterized by stiffness, hardened muscles in the hind quarters and reluctance to move.

The detection of elevated CK and AST levels in horses can be used to diagnose tying up, but the condition can be easily identified by physical examination. The benefit of testing for CK and AST when a horse ties up is the ability to monitor disease progression. If interpreted correctly, CK and AST levels can tell you if the horse is just beginning to tie up, whether it is responding well to an intervention or if the horse is recovering.

Methods

A study conducted over a six-month period (May-November '13) tested approx. 200 Thoroughbred horses bred for flat racing. During monthly routine blood testing, each horse had a complete blood cell count and biochemistry panel conducted. Creatine kinase (CK) and aspartate aminotransferase (AST) were part of the biochemistry assessment. As well as scheduled blood testing, additional tests were conducted to monitor a horses CK and AST levels when tying up was observed.

Results

Over a period of 6 months, 52 out of 200 horses tied up, accounting for 26% of the population. Of the 52 horses, 14 experienced recurrent episodes of tying up, ranging from 2 to 5 cases in the six months. The data is tabulated below.

The incidence of recurrence is shown in FIG. 15.

The horses that experienced recurrent cases of tying up accounted for 52.5% of the total 80 cases, indicating a requirement to monitor horses prone to the condition.

Managing Exertional Rhabdomyolysis

Some horses are more prone to tying up than others, sometimes experiencing episodes of tying up back-to-back, which can be frustrating to trainer, costing money and time. Over the duration of this study, 14 horses were observed to have repeated episodes of tying up.

| CK | AST | Clinical notes |
|---|---|---|
| 6613 | 2279 | Set fast |
| 1236 | 1156 | Set fast |
| 1989 | 2380 | Set fast |
| 4217 | 1444 | Set fast |
| 314 | 2441 | Set fast |
| 5998 | 1505 | Tying up |
| 5700 | 4451 | Set fast |
| 1948 | 1173 | Set fast |
| 1061 | 1027 | Set fast |
| 3780 | 1345 | Set fast |
| 14291 | 1948 | Set fast |
| 4415 | 1042 | Set fast |
| 4781 | 1194 | Set fast |
| 2497 | 1590 | Set fast |
| 3875 | 3930 | Set fast |
| 12607 | 3457 | Set fast |
| 1198 | 2570 | Tying up |
| 1934 | 2740 | Tying up |
| 528 | 2539 | Set fast |
| 3034 | 1043 | Set fast |
| 823 | 1288 | Set fast |
| 12035 | 1196 | Set fast |
| 11563 | 993 | Set fast |
| 9128 | 3984 | Set fast |
| 1132 | 3984 | Set fast |
| 4191 | 3881 | Set fast |
| 577 | 3517 | Set fast |
| 1949 | 2386 | Tying up |
| 23166 | 2600 | Set fast |
| 8682 | 1720 | Set fast |
| 1133 | 2020 | Set fast |
| 6837 | 3090 | Set fast |
| 2329 | 1674 | Set fast |
| 743 | 1462 | Set fast |
| 1015 | 923 | Set fast |
| 5719 | 1286 | Set fast |
| 1013 | 802 | Set fast |
| 2806 | 1632 | Set fast |
| 6068 | 5190 | Set fast |
| 7947 | 5458 | Set fast |
| 8195 | 6940 | Set fast |
| 2086 | 2946 | Set fast |
| 5089 | 3743 | Set fast |
| 3010 | 3055 | Set fast |
| 2307 | 2796 | Tying up |
| 4451 | 3181 | Tying up |
| 3755 | 1040 | Set fast |
| 720 | 1430 | Set fast |
| 1751 | 1996 | Set fast |
| 2159 | 1885 | Set fast |
| 0 | 1482 | 1962 Set fast |
| 0 | 550 | 1280 Tying up |

| SAA | CK | AST | Clinical notes |
|---|---|---|---|
| 0 | 2638 | 688 | Set fast |
| 0 | 3692 | 920 | Set fast |
| 0 | 1948 | 1139 | Set fast |
| 0 | 13391 | 5191 | Set fast |
| 0 | 16667 | 8549 | Tying up |
| 0 | 6140 | 14479 | Tying up |
| 0 | 21541 | 20872 | Tying up |
| 0 | 1103 | 15327 | Set fast |
| 0 | 346 | 11674 | Set fast |
| 0 | 263 | 11046 | Set fast |
| 0 | 1769 | 1068 | Set fast |
| 0 | 1832 | 909 | Set fast |

Device for Managing Exertional Rhabdomyolysis

Figure 17A:
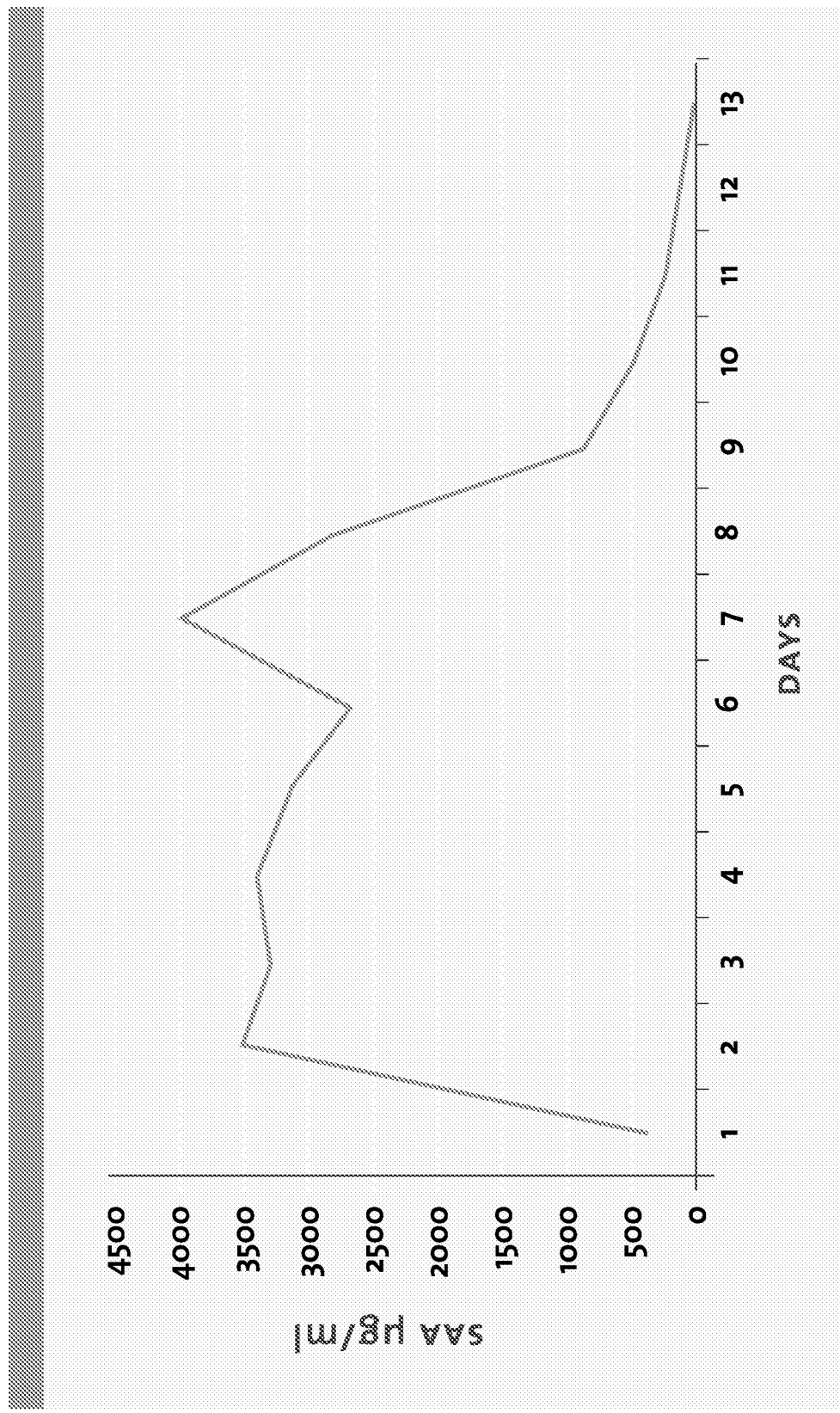

In one embodiment of the device (FIG. 17(a)) the device is a LFD and CK and AST are determined in sequence according to the positioning of the detection reagents on the LFD.

In such a device sample is added to a single sample port and moves along a channel where, for example, it first encounters the reagents required to detect and determine levels of AST and subsequently encounters the reagents necessary to detect and measure CK. In such a device CK and AST must both be measured, as the sample must come into contact with the reagents for the detection of each as it moves through the channel. CK and AST are clearly indicated (labelled) by markings on the device to differentiate between the two (i.e "CK" is printed on the device at the test line for CK and "AST" is printed on the device at the test line for AST).

Figure 17B:
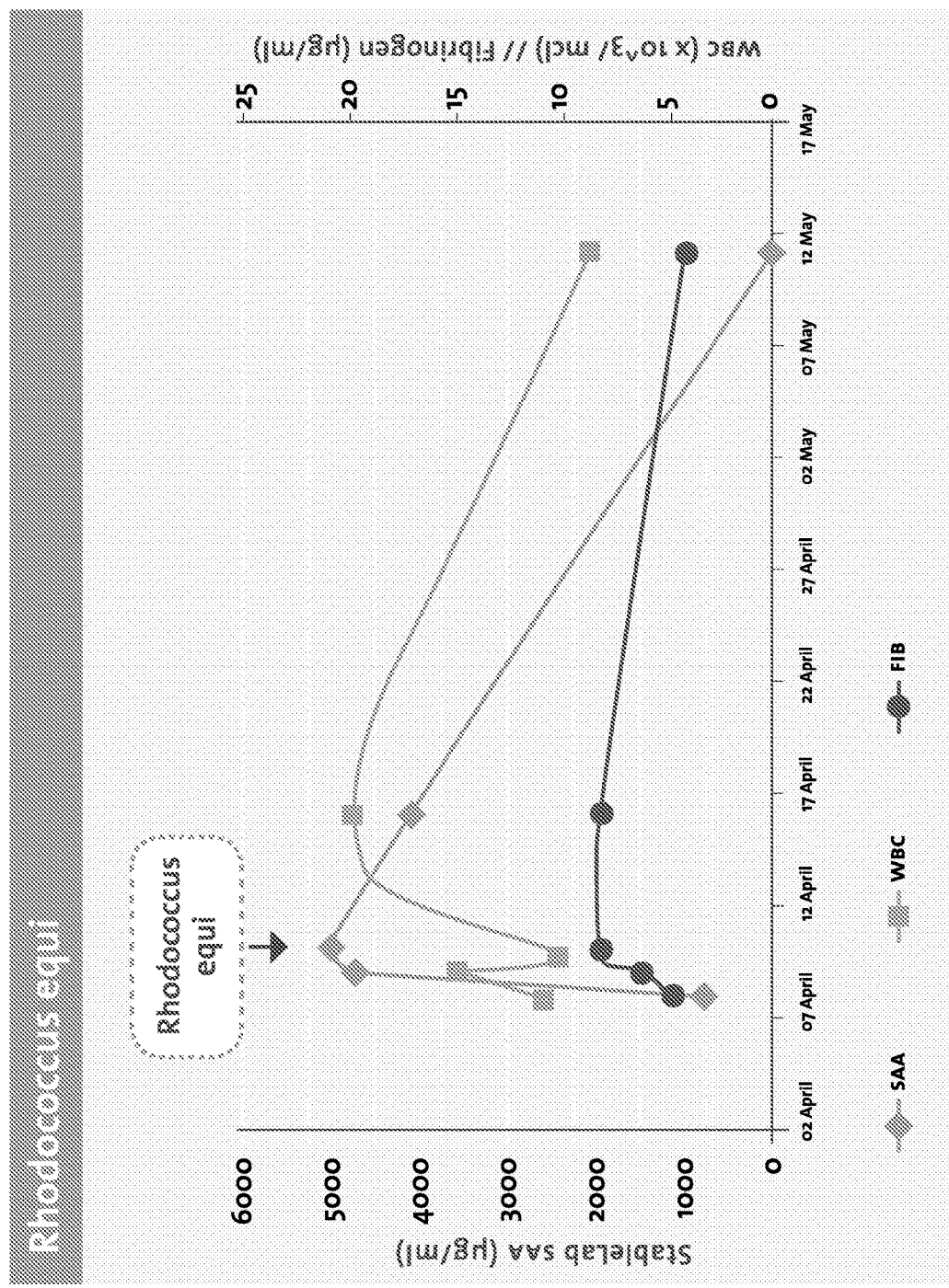

In one embodiment of the device (FIG. 17(b)) the markings beside the test line for CK appear as "CK" and the markings for AST appear as "SGOT" representing serum glutamic oxaloacetic transaminase by which AST is also known. In this embodiment the CK marking is above the SGOT marking.

Figure 17C:
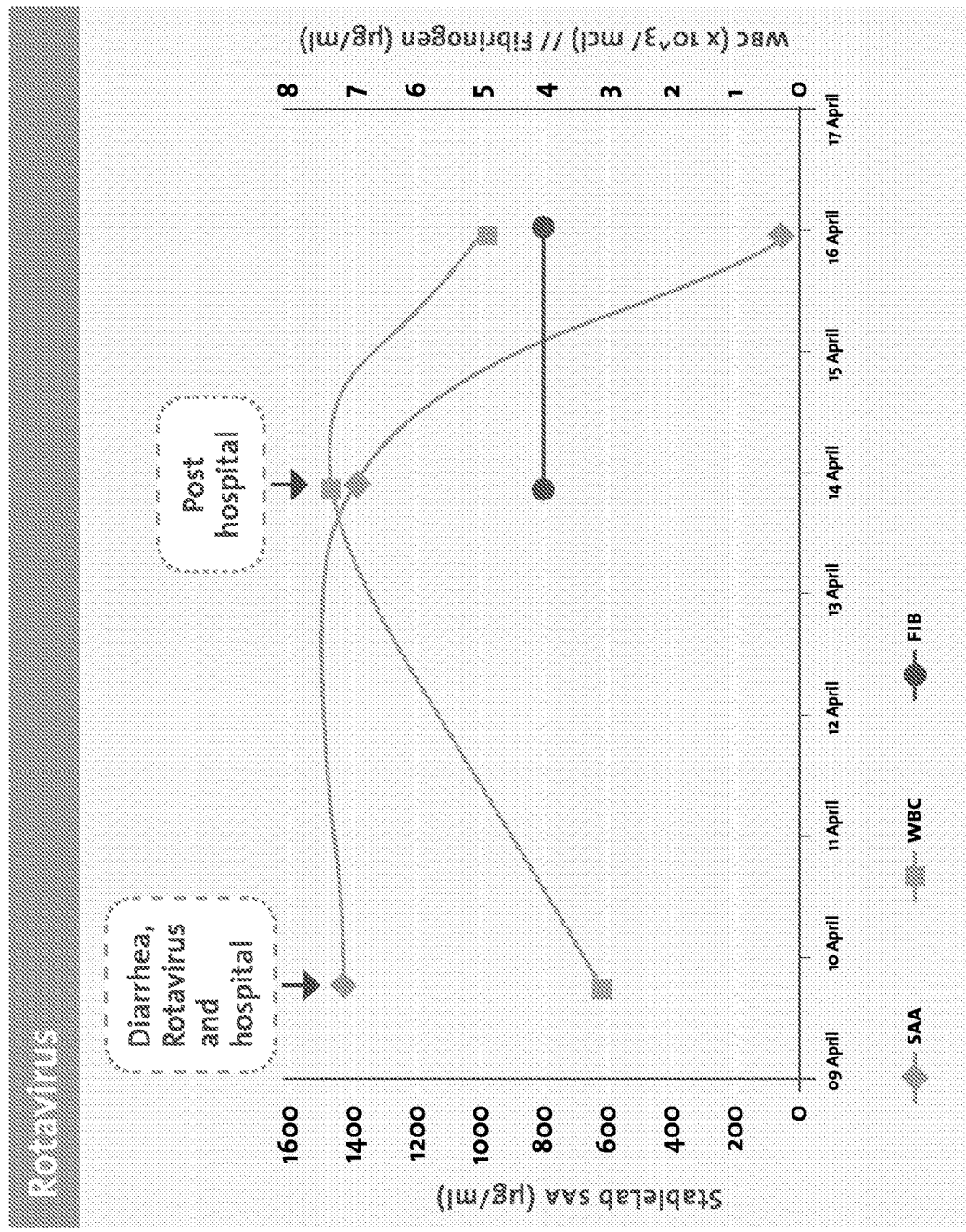

In one embodiment of the device (FIG. 17(c)) CK and AST are measured on a LFD in parallel to each other. Such a device contains two distinct sample ports, which run in parallel to each other and which are not in fluid communication with each other. Sample is added in separate steps to each sample port. The first of the two channels which make up this embodiment contains only the reagents necessary for the detection of CK. The second of the two channels contains only the reagents necessary for the detection of AST. Such a device allows for the analysis of CK/AST in parallel or individually. In the Figure the channel which detects and measures CK is visible on the left (front) side of the cartridge. The channel which detects and measures AST is visible on the right (front) side of the cartridge. The sample zones directly underneath the sample ports of the device may be treated with reagents which encourage the performance of the test.

In one embodiment of the device FIG. 17(d)) CK and AST are determined by the application of sample to a single sample port. The sample then separates and moves along two separate channels. The two channels are chemically treated in the same fashion as those described above whereby the antibody reagents for the detection and measurement of CK are present only in the channel visible to the front left of the cartridge and those for the detection of AST are present only in the channel is which is visible on the front right of the device. The sample application zone of the device may be chemically treated in such a way as to encourage the performance of the test.

It will be appreciated that the orientation (left\right) in the above embodiments is not essential.

Example 8—Presence of SAA in Healthy Horses

Introduction and Methods

A population study involving 105 thoroughbred horses was conducted in order to understand the normal level of serum amyloid A in healthy horses. The horses were a random mixture of males and females, a mixture of grades, ranging in age from 2- to 5-year-old and had raced a maximum of five times each. All horses were managed in the same way with individual boxes, photoperiod of 4:30 AM to 9 PM, a natural indoor temperature (18-C-20-C), and the same feeding and training schedules. Detailed veterinary analysis of each horse immediately after sampling was beyond the scope of the present study. However, it was noted by the veterinarian that all horses were fit for work.

All blood analysis was performed by a suitably qualified in-house laboratory technician. To minimize the impact of circadian fluctuations blood was drawn between 2 PM and 3 PM according to in-house procedures and veterinary recommendation by the in-house vet. The blood was drawn into blood tubes appropriate for the parameters to be tested.

SAA was measured using a calibrated Konelab 20 instrument from Thermo Scientific and the "Eiken" test reagents supplied by Mast Diagnostic. According to the manufacturer the range of the test is 5-500 ug/ml with a coefficient of variation <10% and an accuracy of 85-115%.

The results for each of the parameters under analysis in this study for each of the 105 horses were compiled and analyzed using Microsoft excel.

Results and Discussion

We considered the absolute presence or absence of serum amyloid A (SAA) in a population of 105 thoroughbred racehorses bred for racing. From 105 subjects only 9 subjects were found to have any detectable level of SAA.

The lowest detected level was 5.4 µg/ml with 4 out of the 9 positive SAA results under 25 µg/ml indicating that the sensitivity of the method was capable of consistently determining concentrations in this range, and it was considered that absolute negative results (zero) truly reflect the practical absence of the protein.

The use of total white blood cell (WBC) counts, plasma fibrinogen (Fb) and SAA have been well reported for the diagnosis of inflammation in horses. The normal ranges for WBC in thoroughbred racehorse has been well reported by Allen et. al. in 1984 who give various acceptable ranges for fillies, colts and of different ages and stages of training. For the purposes of this study the normal ranges for WBC's were considered to be $6.0-9.9 \times 10^9$/L. Fb is an acute phase protein which is now well established as a marker of inflammation in horses, initial reports for the use of fibrinogen as a marker of acute inflammation in horses include van Wuijckhuise-Sjouke (1984) and Patterson et. al. (1988). Again various normal ranges have been reported and for the purposes of this study 2.0-5.0 mg/ml is considered to be the normal range. Pepys et. al. reported the first immunoassay for SAA in 1989 and concluded that SAA was present only at "trace" levels in healthy horses but elevated rapidly following tissue injury (surgery) infection and inflammation. It is not clear whether the particular immunoassay used in that work had the required sensitivity to establish if SAA was actually absent.

Thus the present invention represents the first report that SAA is absent in normal healthy horses.

96 out of 105 (91.5%) subjects gave absolute negative results for SAA indicating that the normal level of SAA is in fact none or zero. For each of the 9 positive results, the levels of WBC and Fb were also considered to report if an inflammatory response may have been occurring. It was also considered reasonable that in any population of racehorses in training that up to 10% of the population may be suffering from some kind of inflammatory process, albeit at the sub-clinical or mildly clinical stages.

5 of the subjects had highly elevated SAA levels (between 969-1868 µg/ml) in each of these cases the Fb level was highly elevated (5.7 mg/ml or higher).

Possibly most interesting is that the 2 subjects with SAA levels within 5-20 µg/ml had corresponding WBC levels that were lower than the normal range while the fibrinogen was either normal or mildly elevated. As SAA is understood to respond earlier than Fb, these two examples may reflect very early stages of an inflammatory response, where WBC's become depleted in an immune response upstream of new WBC production, and, whereby Fb had not yet elevated. Subject 105 had an SAA level of 21 µg/ml and corresponding elevated Fb level of 5.5 mg/ml. None of the 96 SAA-negative horses had an elevated Fb measurement higher than 5.0 mg/ml.

In summary, this example demonstrates that from a population of 105 racehorses in training SAA is not at all present in normal healthy horses and in horses where SAA is detected its likely that an inflammatory process had been triggered.

TABLE 1

| Horse | WBC (10$^9$/L) | Fibrinogen (mg/ml) | SAA (µg/ml) |
|---|---|---|---|
| 1 | 9.7 | 4.9 | 0 |
| 2 | 8.7 | 3.8 | 0 |
| 3 | 8.7 | 3.7 | 0 |
| 4 | 9.3 | 3.5 | 0 |
| 5 | 7.9 | 4.4 | 0 |
| 6 | 11.6 | 3.8 | 0 |
| 7 | 7 | 3.4 | 0 |
| 8 | 7 | 4.6 | 0 |
| 9 | 6.4 | 2.7 | 0 |
| 10 | 9.3 | 3.5 | 0 |
| 11 | 7.1 | 3 | 0 |
| 12 | 7.9 | 2.9 | 0 |
| 13 | 6.1 | 4 | 0 |
| 14 | 6.7 | 2.7 | 0 |
| 15 | 9 | 3.6 | 0 |
| 16 | 8.3 | 2.4 | 0 |
| 17 | 7.8 | 3.8 | 0 |
| 18 | 7.3 | 3 | 0 |
| 19 | 8.8 | 2.6 | 0 |
| 20 | 10.2 | 4 | 0 |
| 21 | 9.4 | 3.6 | 0 |
| 22 | 7.4 | 3 | 0 |
| 23 | 7.5 | 3.6 | 0 |
| 24 | 8.6 | 3.3 | 0 |
| 25 | 7.8 | 3.3 | 0 |
| 26 | 8.9 | 3 | 0 |
| 27 | 8.1 | 3.3 | 0 |
| 28 | 11.1 | 3.3 | 0 |
| 29 | 8 | 3.9 | 0 |
| 30 | 5.7 | 4 | 0 |
| 31 | 9.1 | 3.5 | 0 |
| 32 | 8.1 | 4 | 0 |
| 33 | 9 | 4.3 | 0 |
| 34 | 8.1 | 3.3 | 5.4 |
| 35 | 8.5 | 2.9 | 0 |
| 36 | 7.7 | 3.4 | 0 |
| 37 | 8.3 | 2.6 | 0 |
| 38 | 8.3 | 3.6 | 0 |
| 39 | 11.2 | 3.2 | 0 |
| 40 | 9.1 | 3.1 | |
| 41 | 10.7 | 3.5 | 0 |
| 42 | 9.6 | 3.1 | 0 |
| 43 | 8 | 3.3 | 0 |
| 44 | 15.6 | 3.5 | 0 |
| 45 | 10.2 | 3.6 | 0 |
| 46 | 8.1 | 3.9 | 0 |
| 47 | 8.4 | 2.5 | 0 |
| 48 | 11.8 | 3.1 | 0 |
| 49 | 7.5 | 3 | 0 |
| 50 | 9.9 | 3 | 0 |
| 51 | 8.1 | 3.4 | 0 |
| 52 | 9.7 | 3.2 | 0 |
| 53 | 7.8 | 3.4 | 0 |
| 54 | 8.7 | 3.4 | 0 |
| 55 | 7.9 | 3.5 | 0 |
| 56 | 8.4 | 3 | 0 |
| 57 | 9.4 | 3.5 | 0 |
| 58 | 9.5 | 3.2 | 0 |
| 59 | 9.3 | 3.2 | 0 |
| 60 | 7.8 | 3.4 | 0 |
| 61 | 7.9 | 3.2 | 0 |
| 62 | 8.9 | 3.8 | 0 |
| 63 | 8 | 3.1 | 0 |
| 64 | 7.7 | 3.3 | 0 |
| 65 | 10.1 | 3.5 | 0 |
| 66 | 5 | 5.2 | 17.1 |
| 67 | 5.5 | 4.5 | 0 |
| 68 | 6.2 | 4 | 0 |
| 69 | 6.6 | 3.8 | 0 |
| 70 | 8.4 | 3.6 | 0 |
| 71 | 9.9 | 4 | 0 |
| 72 | 6.7 | 4.4 | 0 |
| 73 | 6.1 | 3.4 | 0 |
| 74 | 6.5 | 3.2 | 0 |
| 75 | 8.8 | 2.9 | 0 |
| 76 | 5.2 | 3.7 | 0 |
| 77 | 7.1 | 4.2 | 0 |
| 78 | 5.6 | 3.2 | 0 |
| 79 | 11.3 | 7.6 | 1225 |
| 80 | 5.7 | 3.5 | 0 |
| 81 | 7.1 | 3.3 | 0 |
| 82 | 10.2 | 3.6 | 0 |
| 83 | 8.8 | 3.8 | 0 |
| 84 | 6.7 | 3.5 | 0 |
| 85 | 5.2 | 4 | 0 |
| 86 | 10.4 | 3 | 0 |
| 87 | 5.3 | 3.4 | 8.6 |
| 88 | 7.9 | 4 | 0 |
| 89 | 9.9 | 3.6 | 0 |
| 90 | 8.2 | 3.8 | 0 |
| 91 | 8.9 | 4 | 0 |
| 92 | 6.4 | 3.8 | 0 |
| 93 | 8.2 | 6.6 | 1868 |
| 94 | 9.9 | 3.3 | 0 |
| 95 | 5.9 | 5.7 | 969 |
| 96 | 10.1 | 6.4 | 1010 |
| 97 | 6.8 | 4.1 | 0 |
| 98 | 6.3 | 4.5 | 0 |
| 99 | 6.5 | 4.7 | 0 |
| 100 | 10.3 | 7.5 | 1555 |
| 101 | 8.5 | 3.2 | 0 |
| 102 | 9.1 | 4.2 | 0 |
| 103 | 10 | 3.9 | 0 |
| 104 | 6.7 | 3.7 | 0 |
| 105 | 9.4 | 5.5 | 21.1 |

REFERENCES

Used in Example 8:
1. Leucocyte counts in the healthy English Thoroughbred in Training. Allen B V, Kane C E, Powell D G. Equine Veterinary Journal 1984; 16:207-209.
2. Serum amyloid A protein (SAA) in horses: objective measurement of the acute phase response. Pepys M B, Baltz M L, Tennent G A, Kent J, Ousey J, Rossdale P D. Equine Vet J. 1989 March; 21(2):106-9.
3. Plasma fibrinogen as a parameter of the presence and severity of inflammation in horses and cattle. van Wuijckhuise-Sjouke L A. Tijdschr Diergeneeskd. 1984 Nov. 1; 109(21):869-72.
4. Acute phase response in the horse: plasma protein changes associated with adjuvant induced inflammation. Patterson S D, Auer D, Bell K. Biochem Int. 1988 August; 17(2):257-64

The invention claimed is:

1. A test fluid collection system for a collection of metered quantity of a test fluid to be diluted for analysis, the system comprising:
   a housing comprising:
   i) a collection tip;
   ii) a collection port;
   iii) a dispensing inlet; and
   iv) a dispensing nozzle;
   wherein the collection tip is at a first end of the housing and is adapted to contact a sample of the test fluid;
   wherein the collection port is proximal to and in fluid communication with the collection tip and comprises two spaced members having opposing hydrophilic surfaces;
   wherein said surfaces define a volume between them which corresponds to the metered quantity of test fluid to be collected;

wherein the distance between the spaced members enables the test fluid from the sample tip to be drawn into the volume by capillary action;

wherein the collection tip and dispensing nozzle are at opposite ends of said housing;

wherein the dispensing inlet is proximal to the collection tip, and in fluid communication via a dispensing channel to the dispensing nozzle which runs through said housing;

wherein the housing is adapted to be fitted into the opening of a liquid container containing liquid for diluting the metered quantity of the test fluid, with said collection port and said dispensing inlet within said container, and with a seal fit between said opening and said housing; and wherein the dispensing channel decreases in diameter between 10-21% over the height of the dispensing nozzle and wherein the dispensing nozzle is flared at the dispensing nozzle exit to dispense drops of the diluted test fluid in a uniform manner from the container when the volume of said container is reduced and the diluted test fluid in said container is forced into said dispensing channel.

2. The system as claimed in claim 1, wherein the housing has a circular cross-section of circumference between 15 and 20 mm at the widest point.

3. The system as claimed in claim 1, wherein the collection tip is positioned on a collection stem, which stem incorporates the dispensing inlet and the collection port.

4. The system as claimed in claim 1, wherein the collection stem is greater than or equal to about 20, 25, 30, 40, 45, or 50 mm length.

5. The system as claimed in claim 1, wherein the surfaces are parallel or are angled away from each other by about 1°, 2°, 3°, 4°, or 5°.

6. The system as claimed in claim 1, wherein the surfaces are coated with a hydrophilic coating or an anti-coagulant.

7. The system as claimed in claim 1, wherein the members are bevelled or shaped to increase surface tension in the volume configured to hold the fluid.

8. The system as claimed in claim 1, wherein the members are two closely aligned walls which form an open channel.

9. The system as claimed in claim 1, wherein the housing includes a fitting portion which is adapted to be a push fit into the opening of the container and retained by friction or compression.

10. The system as claimed in claim 1, wherein the housing includes a fitting portion which is adapted to be a push fit into the opening of the container and retained by friction or compression, and wherein the fitting portion is a cylindrical waist which optionally includes a frusto conical portion which is tapered to facilitate insertion of the fitting portion into the opening of the container.

11. The system as claimed in claim 1, wherein the collection tip is profiled and dimensioned to allow attachment of a luer end needle, to wick a test fluid sample directly from the sample, or both.

12. The system as claimed in claim 1, further comprising a liquid container containing liquid for diluting the metered quantity of the test fluid.

13. The system as claimed in claim 1, wherein the dispensing channel within the dispensing nozzle decreases in diameter by between 20-21% over the height of the dispensing nozzle.

* * * * *